United States Patent
Seeberger et al.

(10) Patent No.: US 10,220,083 B2
(45) Date of Patent: Mar. 5, 2019

(54) **VACCINES AGAINST *STREPTOCOCCUS PNEUMONIAE* SEROTYPE 8**

(71) Applicant: MAX-PLANCK-GESELLSCHAFT ZUR FÖRDERUNG DER WISSENSCHAFTEN E.V., Munich (DE)

(72) Inventors: Peter H. Seeberger, Kleinmachnow (DE); Claney Lebev Pereira, Berlin (DE); Chakkumkal Anish, The Hague (NL); Benjamin Schumann, Berlin (DE); Sharavathi Guddehalli Parameswarappa, Berlin (DE); Heung Sik Hahm, Charlottesville, VA (US); Subramanian Govindan, Tamil Nadu (IN)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 15/513,868

(22) PCT Filed: Sep. 28, 2015

(86) PCT No.: PCT/EP2015/072294
§ 371 (c)(1),
(2) Date: Mar. 23, 2017

(87) PCT Pub. No.: WO2016/046420
PCT Pub. Date: Mar. 31, 2016

(65) Prior Publication Data
US 2017/0239341 A1    Aug. 24, 2017

(30) Foreign Application Priority Data

Sep. 26, 2014 (EP) .................................... 14186597
Apr. 10, 2015 (EP) .................................... 15163290

(51) Int. Cl.
| | | |
|---|---|---|
| *A61K 31/7028* | (2006.01) | |
| *A61K 39/09* | (2006.01) | |
| *C07H 15/18* | (2006.01) | |
| *C07H 15/04* | (2006.01) | |
| *A61K 39/085* | (2006.01) | |
| *C07K 16/12* | (2006.01) | |
| *G01N 33/569* | (2006.01) | |
| *A61K 47/64* | (2017.01) | |
| *A61K 39/00* | (2006.01) | |

(52) U.S. Cl.
CPC ........ *A61K 39/092* (2013.01); *A61K 31/7028* (2013.01); *A61K 39/085* (2013.01); *A61K 47/646* (2017.08); *A61K 47/6415* (2017.08); *C07H 15/04* (2013.01); *C07H 15/18* (2013.01); *C07K 16/1271* (2013.01); *G01N 33/56944* (2013.01); *A61K 2039/575* (2013.01); *A61K 2039/6037* (2013.01); *A61K 2039/627* (2013.01); *G01N 2333/3156* (2013.01)

(58) Field of Classification Search
None
See application file for complete search history.

(56) References Cited

FOREIGN PATENT DOCUMENTS

| WO | WO 96/40225 | 12/1996 |
|---|---|---|
| WO | WO 2009/000826 | 12/2008 |
| WO | WO 2013/078236 | 5/2013 |

OTHER PUBLICATIONS

Safari et al., "Identification of the Smallest Structure Capable of Evoking Opsonophagocytic Antibodies against *Streptococcus pneumoniae* Type 14" Infection and Immunity Oct. 2008, pp. 4615-4623 (Year: 2008).*
Malcom et al., "Surface Layers From Bacillus Alvei As a Carrier for a *Streptococcus pneumoniaB* Conjugate Vaccine" Advances in Bacterial Paracrystalline Surface Layers edited by Beveridge and Koyal, Plenum Press, Chapter 21, pp. 219-233 (Year: 1993).*
Alonsodevelasco et al., "*Streptococcus pneumoniae*: virulence factors, pathogenesis, and vaccines." Microbiological Reviews (1995) 59(4):591-603.
Chang et al., "Structure-Function Relationships for Human Antibodies to Pneumococcal Capsular Polysaccharide from Transgenic Mice with Human Immunoglobulin Loci" Infection and Immunity (2002) 70(9):4977-4986.
Fleuridor et al., "A Cryptococcal Capsular Polysaccharide Mimotope Prolongs the Survival of Mice with *Cryptococcus neoformans* Infection" The Journal of Immunology (2001) 166(2):1087-1096.
Jones et al., "The Structure of the Type VIII Pneumococcus Specific Polysaccharide" J. Am. Chem. Soc. (1957) 79(11):2787-2793.
Yano et al., "Characterization of Gene Use and Efficacy of Mouse Monoclonal Antibodies to *Streptococcus pneumoniae* Serotype 8" Clinical and Vaccine Immunology (2011):18(1):59-66.
International Search Report and Written Opinion dated Oct. 27, 2015 for PCT Application No. PCT/EP2015/072294, filed Sep. 28, 2015.
Pozsgay et al., "Protein conjugates of synthetic saccharides elicit higher levels of serum IgG lipopolysaccharide antibodies in mice than do those of the O-specific polysaccharide from *Shigella dysenteriae* type 1" PNAS (1999) 96:5194-5197.

(Continued)

*Primary Examiner* — Eric Olson
(74) *Attorney, Agent, or Firm* — Knobbe, Martens, Olson & Bear, LLP

(57) ABSTRACT

The present invention relates to synthetic saccharides of general formula (I) that are related to *Streptococcus pneumoniae* serotype 8 capsular polysaccharide, conjugates thereof and the use of said saccharides and conjugates for raising a protective immune response in a human and/or animal host. Furthermore, the synthetic saccharide structures of general formula (I) are useful as marker in immunological assays for detection of antibodies against *Streptococcus pneumoniae* bacteria.

25 Claims, 19 Drawing Sheets

(56) References Cited

OTHER PUBLICATIONS

Robbins et al., "Synthesis, characterization, and immunogenicity in mice of *Shigella sonnei* O-specific oligosaccharide-core-protein conjugates" PNAS (2009) 106:7974-7978.

Wu et al., "Synthesis of Monomeric and Dimeric Repeating Units of the Zwitterionic Type 1 Capsular Polysaccharide from *Streptococcus pneumoniae*" Chem. Eur. J. (2010) 16:3476-3488.

* cited by examiner

Figure 1

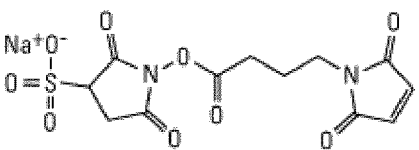

Sulfo-GMBS
N-(γ-Maleimidobutyryloxy) sulfosuccinimide ester
MW 382.28
Spacer Arm 7.3 Å

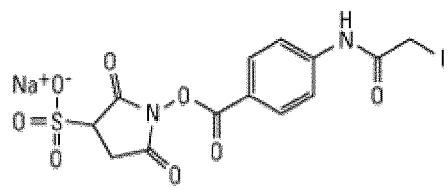

Sulfo-SIAB
Sulfosuccinimidyl (4-iodoacetyl) aminobenzoate
MW 504.19
Spacer Arm 10.6 Å

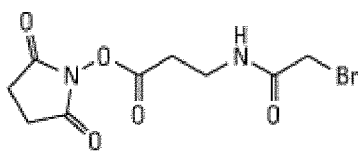

SBAP
Succinimidyl-3-(bromoacetamido)propionate
MW 307.10
Spacer Arm 6.2 Å

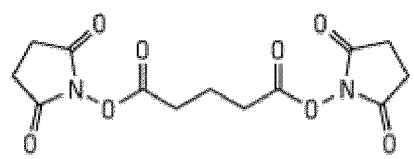

DSG
Disuccinimidyl glutarate
MW 326.26
Spacer Arm 7.7 Å

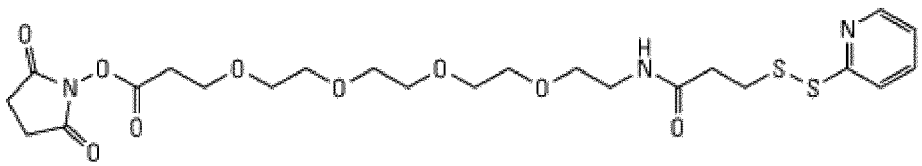

PEG4-SPDP
2-Pyridyldithiol-tetraoxatetradecane-N-hydroxysuccinimide
MW 559.17
Spacer Arm 25.7 Å

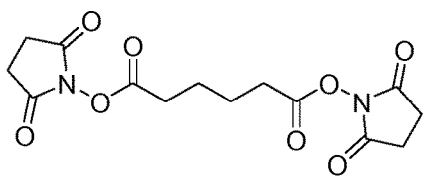

DSA
Disuccinimidyl adipate

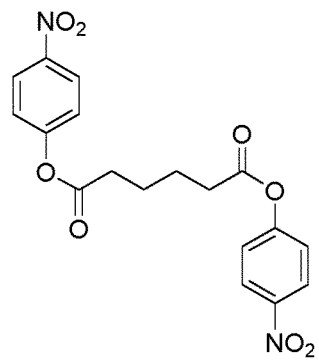

Bis-(4-nitrophenyl) adipate

Bis-(4-nitrophenyl)succinate

Ethylene glycol-bis(succinic acid N-hydroxysuccinimide ester)

A. tetrasaccharide conjugated with a carrier protein

B. tetrasaccharide conjugated with a glycosphingolipid

C. tetrasaccharide conjugated on a solid support

A. saccharides with symbols

Compound 19 (C1)

Compound 18 (C2)

Compound 20 (D1)

Compound 21 (A1)

Compound 10 (A2)

Compound 22 (B1)

Compound 49

B.

C.

D.

A.

A: *S. pneumoniae* ST8; mAb 1H8
B: *S. pneumoniae* ST8; mAb isotype control (anti-*Y. pestis* LPS core)
C: *S. pneumoniae* ST1; mAb 1H8

Cmpd 90

A

B

C

D

E

F

G

VACCINES AGAINST *STREPTOCOCCUS PNEUMONIAE* SEROTYPE 8

FIELD OF THE INVENTION

The present invention relates to synthetic saccharides of general formula (I) that are related to *Streptococcus pneumoniae* serotype 8 capsular polysaccharide, conjugates thereof and the use of said saccharides and conjugates for raising a protective immune response in a human and/or animal host. Furthermore, the synthetic saccharide structures of general formula (I) are useful as marker in immunological assays for detection of antibodies against *Streptococcus pneumoniae* bacteria.

BACKGROUND OF THE INVENTION

*Streptococcus pneumoniae* is a Gram-positive, encapsulated bacterium that is a main cause of infections of the respiratory tract and can lead to severe invasive pneumococcal disease (IPD). More than 90 different pneumococcal serotypes have been described to date. These are classified by the structure of their capsular polysaccharide (CPS), which is unique to each serotype. Consequently, the immune response generated against the CPS varies between different serotypes. This is used to generate specific antibodies in rabbits against the antigen of each serotype. Cross-reactivity between these specific antibodies and other serotypes than those they were raised against is often observed, due to structural similarities of the CPS of different serotypes. Due to its immunological properties, CPS is used as the main component of *S. pneumoniae* vaccines.

The first efficient vaccine that contained the CPS of four different serotypes was described in 1945. It then took over thirty years until a vaccine was introduced that covered 14 serotypes, shortly followed by a 23-valent vaccine. However, these polysaccharide vaccines had several shortcomings. They were not able to elicit a long-lasting protection and were not effective in the populations most vulnerable to infection, namely children under two years of age as well as immunodeficient and elderly patients. These shortcomings result from the immunology of carbohydrates and were overcome by the introduction of carbohydrate-protein conjugate vaccines. The first pneumococcal conjugate vaccines were the seven-valent (PCV-7) and 10-valent (PCV-10) vaccine. PCV-7 was later replaced with the most recent vaccine (PCV-13), which contains the CPS-glycoconjugates of 13 different serotypes.

The currently marketed vaccines are effective in North America and Europe for individuals of a particular age. The manufacturing process for these vaccines is complex and results in a higher price. Therefore, the vaccine is unaffordable in most developing countries. It is the object of the present invention to provide affordable synthetic saccharide vaccines that contain one of the most prevalent serotypes of the developing world.

*Streptococcus pneumoniae* serotype 8 has been associated with serotype replacement and cases of invasive pneumococcal disease increased steadily in the last decades.

*Streptococcus pneumoniae* type 8 is one of the prevalent *S. pneumoniae* serotypes. The structure of the native Sp8 capsular polysaccharide repeating unit is a tetrasaccharide with the sequence →4)-Glcα-(1→4)-Galα-(1→4)-GlcAβ-(1→4)-Glcβ(1→(*J. Am. Chem. Soc.* 1957, 79 (11), 2787):

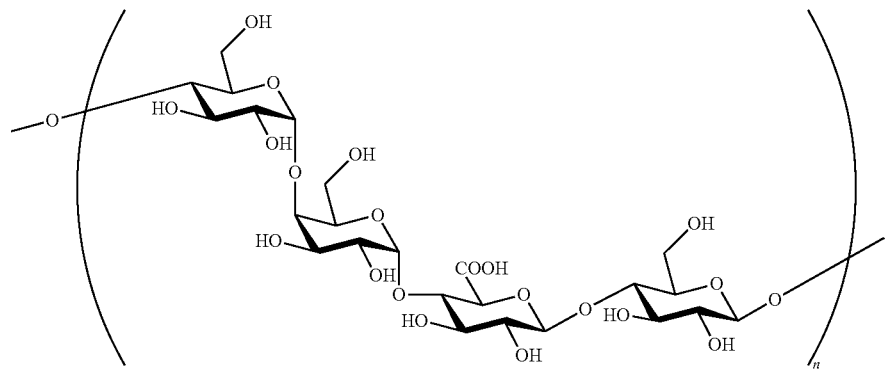

Interestingly, the native serotype 8 tetrasaccharide repeating unit harbors the disaccharide repeating unit of serotype 3. Consequently, cross-reactivity has been found between sera against serotypes 3 and 8, although precipitation of antibodies by the respective heterologous polysaccharide is incomplete. Insufficient epitope overlap may be the reason why capsular polysaccharides (CPS) from both serotypes were included in the 23-valent polysaccharide vaccine despite extensive considerations about cross-reactivity before manufacturing this vaccine.

WO 9640225 A1 provides a *Streptococcus pneumoniae* serotype 8 oligosaccharide protein conjugate consisting of mixtures of 2 to 4 repeating units coupled using EDC to tetanus toxoid. The mixtures of 2 to 4 repeating units are obtained by non-selective cleavage of the capsular polysaccharide followed by size exclusion chromatography. It is well known that oligosaccharides obtained by degradation of capsular polysaccharides present a high degree of heterogeneity due to co-isolated impurities and new epitopes that are introduced during degradation or as part of an immune evasion strategy by the pathogen. In the case of WO 9640225 A1, this heterogeneity is increased by the non-selective cleavage (TFA, 100° C.), which leads to a mixture of at least 4 saccharides for a fraction containing two repeating units. Thus, oligosaccharides isolated from capsular polysaccharides comprise a set of potentially immunogenic epitopes depending on structural determinants that are recognized as "non-self" by the host immune system. Therefore, a drawback of the immunization with vaccines based on conjugates of isolated oligosaccharides, such as the conjugates of WO 9640225 A1, is the generation of a polyclonal immune response that is directed towards multiple immunogenic epitopes, among which some are non-protective (i.e. the antibodies that are elicited do not protect from diseases associated with *S. pneumoniae* type 8) or are immunodominant. Such polyclonal immune response leads to toxicities that are not acceptable for a vaccine that is prophylactically administered to healthy (often infant) populations. This drawback is overcome by the pure saccharide of the present invention, which presents a well-defined structure, a degree of purity suitable for clinical applications and no batch-to-batch variability.

Moreover, WO 9640225 A1 discloses that a mixture of oligosaccharides containing 1 repeating unit i.e. a mixture of tetrasaccharides do not contain an immunogenic epitope and that at least mixtures of octasaccharides are required for preparing a conjugate against *S. pneumoniae* type 8. Surprisingly, the inventors have found that even short saccharides described herein contain a protective glycan epitope and are able to induce a protective immune response against *S. pneumoniae* serotype 8 bacteria in a human and/or animal host.

Thus, it is the objective of the present invention to provide a pure synthetic saccharide of general formula (I) that is related to the capsular polysaccharide of *Streptococcus pneumoniae* serotype 8 and contains a protective immunogenic glycan epitope i.e. a glycan epitope that is elicits and is recognized by antibodies which protect against diseases caused by *S. pneumoniae* type 8. Said saccharide is suitable to be conjugated to an immunogenic carrier to provide a conjugate and a pharmaceutical composition thereof that are useful for prevention and/or treatment of diseases associated with *Streptococcus pneumoniae*, and more specifically against diseases associated with *Streptococcus pneumoniae* serotype 8. Furthermore, the synthetic saccharide of general formula (I) is useful as marker in immunological assays for detection of antibodies against *Streptococcus pneumoniae* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 1 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i. e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from Smilax ornata (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS7, QS17, QS18, QS21, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly(α-hydroxy acid), polyhydroxybutyric acid, polyorthoester, polyanhydride, polycaprolactone;

CD1d ligands, such as an α-glycosylceramide, phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3″-sulfo-galactosyl-ceramide;

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and blocking the rapid dispersal of the antigen challenge.

Saccharides are known by the person skilled in the art as TI-2 (T cell independent-2) antigens and poor immunogens. Therefore, to produce a saccharide-based vaccine, said saccharides are conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunogenicity in comparison with the saccharide per se. Thus, the conjugation of the saccharides to the immunogenic carrier has as effect the stimulation of the immune response against said saccharide, without inducing an immune response against the said immunogenic carrier.

Surprisingly, it was found that a pure saccharide of general formula (I) according to the present invention contains a protective immunogenic glycan epitope and is able to induce a protective immune response against S. pneumoniae serotype 8 bacteria in a human and/or animal host. The saccharide of general formula (I) elicits antibodies that are cross-reacting with the S. pneumoniae serotype 8 capsular polysaccharide, recognize specifically S. pneumoniae serotype 8 bacteria and opsonize them for killing by phagocytes.

The present invention provides a saccharide of general formula (I)

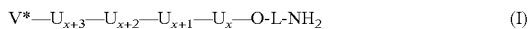

wherein x is an integer selected from 1, 2, 3 and 4;

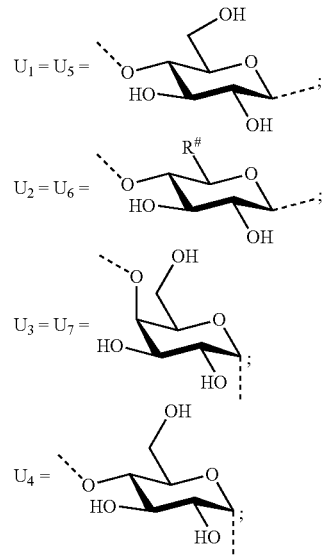

V*— represents H—, H—$U_x$— or H—$U_{x+1}$—$U_x$—;

$R^\#$ represents —COOH or —$CH_2OH$;

L represents a linker; or a pharmaceutically acceptable salt thereof.

-L- is defined as a linker and is part of the fragment —O-L-$NH_2$. Thus, the linker -L- is bound to an oxygen atom and to the nitrogen atom of the $NH_2$-group. It is preferred that at least two carbon atoms of the linker are between the oxygen atom and the $NH_2$-group, like —O—C—C—$NH_2$. The linker -L- can be an aliphatic chain, wherein the aliphatic chain can optionally include an aromatic chain inserted in it, or a number of heteroatoms oscillating from 0 to 10.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-$NH_2$) and the $NH_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the NH$_2$-group) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably two substituents, such as $R^{10}$ and $R^{11}$, or four substituents such as $R^{10}$, $R^{11}$, $R^{15}$ and $R^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OH$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$;

In case the linker -L- is fluorinated, more than two substituents —F are preferred.

Preferably the linker -L- is selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—, —CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$;

wherein

-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$—CH$_2$—, —(CR$^{10}$R$^{11}$)$_o$—,

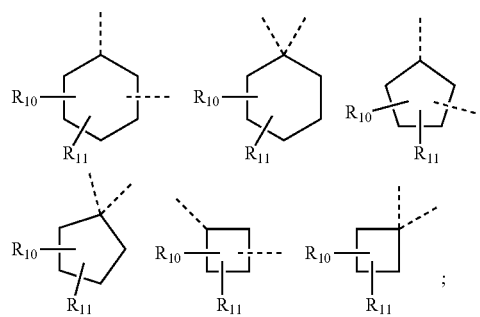

-L$^b$- and -L$^c$- are independently of each other selected from: —O—, —NH—C(O)—NH—, —NH—C(S)—NH—, —NH—C(O)—, —C(O)—NH—, —NH—C(O)—O—, —NR$^9$—, —NR$^{18}$—, —SO$_2$—,

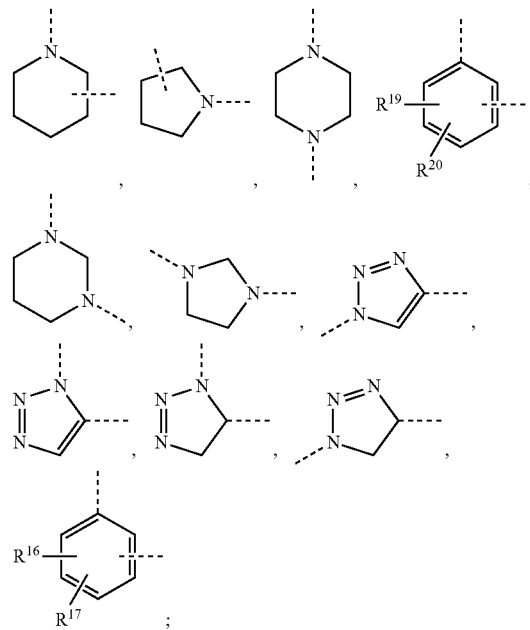

-L$^d$- represents —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —(CH$_2$—CH$_2$—O)$_q$—CH$_2$—,

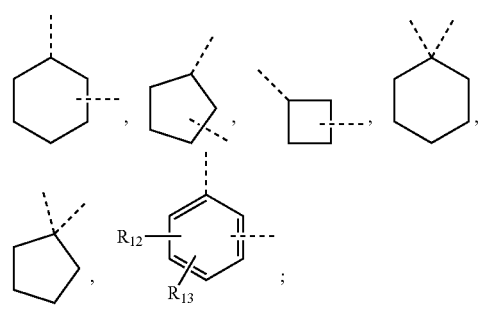

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$^2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

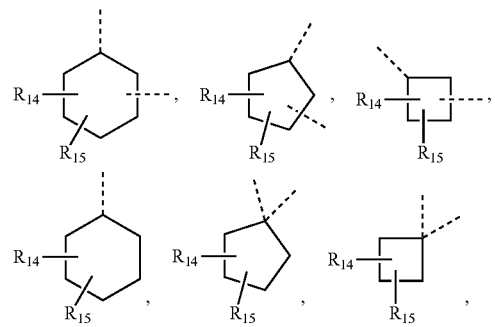

$R^9$ and $R^{18}$ are independently of each other selected from: —CH$_3$, —C$_2$H$_5$, —C$_3$H$_7$, and —C(O)CH$_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$;

o, q, p1 and p2 are independently of each other an integer selected from 1, 2, 3, 4, 5, 6, 7, 8, 9, and 10.

The saccharides of the present invention bear basic and/or acidic substituents and they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

It is clear for the skilled person in the art of carbohydrate chemistry that the saccharides of general (I) are not containing —O—O— bonds and or sugar fragments (U$_x$, U$_{x+1}$, U$_{x+2}$, U$_{x+3}$) connected or bound to each other via their anomeric or C-1 carbons. It is also clear for the person skilled in the art that the stereochemistry of the glycosidic bond is the stereochemistry indicated for the anomeric centre of the sugar fragment in the general formula. Hence, the stereochemistry of the anomeric centre for sugar fragment U$_1$ and U$_5$ is β, for sugar fragment U$_2$ and U$_6$ is β, for sugar fragment U$_3$ and U$_7$ is α and for sugar fragment U$_4$ is α.

The saccharide of general formula (I) contains a protective immunogenic epitope and is able to induce a protective immune response against S. pneumoniae serotype 8 bacteria in a human and/or animal host. The saccharide of general formula (I) elicits antibodies that are cross-reacting with the S. pneumoniae serotype 8 capsular polysaccharide, recognize specifically S. pneumoniae serotype 8 bacteria and opsonize them for killing by phagocytes.

The compounds of the invention according to general formula (I) have the advantage that these are pure synthesized compounds, which can be easily manufactured in accordance with GMP regulations, while isolated mixtures of saccharides as, for instance, disclosed in WO 9640225 A1, are always not fully characterized mixtures with varying composition of the oligosaccharides depending on the source of isolation so that it is problematic to comply with the GMP regulations.

Thus, the vaccine of the present invention contains most preferably only one single compound of the general formula (I) or any other general formula (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX) or (IX-a)-(IX-c) disclosed herein and most preferably only one of the compounds 10, 18-22, 55, 57, 60, and 62-89 bound to an immunogenic carrier, preferably a carrier protein and more preferably CRM$_{197}$. Thus, the compounds of the general formulae (I) or any other general formula (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX) or (IX-a)-(IX-c) are used for the preparation of well defined, well characterized and pure vaccines containing only one synthetically synthesized and well characterized trisaccharide, tetrasaccharide, pentasaccharide, or hexasaccharide preferably linked to an immunogenic carrier, preferably a carrier protein and more preferably CRM$_{197}$. Consequently, the vaccines of the present invention contain only one synthetically synthesized compound of general formulae (I) or any other general formula (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX) or (IX-a)-(IX-c) preferably linked to an immunogenic carrier, preferably a carrier protein and more preferably CRM$_{197}$.

Such vaccines cause fewer side effects and/or non-protective immune responses in comparison to vaccines containing isolated (and not synthesized) mixtures of saccharides obtained by non-selective cleavage of the capsular polysaccharide of Streptococcus pneumoniae serotype 8. Moreover the inventive vaccines can be easier manufactured in accordance with the GMP regulations than the vaccines containing isolated mixtures of non-selectively cleaved capsular polysaccharides and are easier characterized, which makes stability and purity control easier as well as detection of kind and amount of impurities.

It is preferred that the residue R$^\#$ represents —COOH.

An embodiment of the present invention is directed to a saccharide of general formula (I)

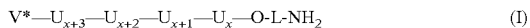

$$V^*—U_{x+3}—U_{x+2}—U_{x+1}—U_x—O\text{-L-}NH_2 \quad (I)$$

wherein V*— represents H—U$_{x+1}$—U$_x$— and x, L, U$_x$, U$_{x+1}$, U$_{x+2}$, U$_{x+3}$ and R$^\#$ have the meanings as defined herein.

Thus, an embodiment of the present invention is directed to a hexasaccharide of general formula (II)

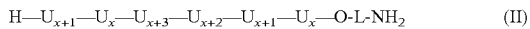

$$H—U_{x+1}—U_x—U_{x+3}—U_{x+2}—U_{x+1}—U_x—O\text{-L-}NH_2 \quad (II)$$

wherein x is an integer selected from 1, 2, 3 and 4;

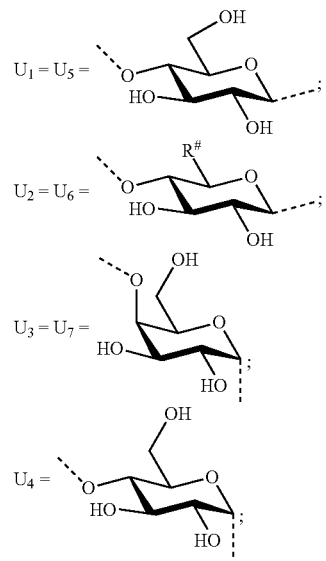

R$^\#$ represents —COOH or —CH$_2$OH;

L represents a linker; or a pharmaceutically acceptable salt thereof.

Even more preferred is a hexasaccharide of general formula (II), wherein $R^{\#}$ represents —COOH.
Thus, a hexasaccharide of general formula (II-a)
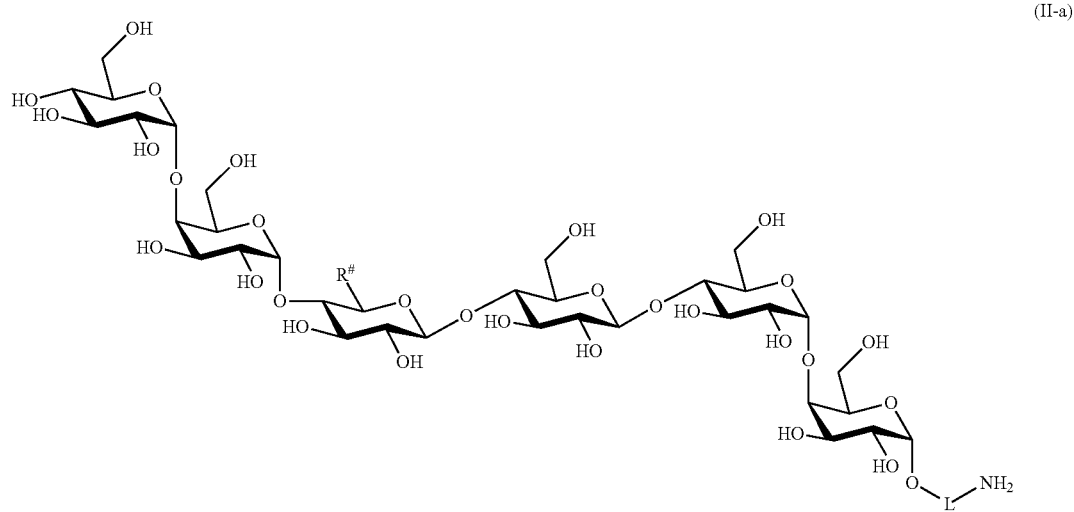
(II-a)
wherein $R^{\#}$ and L have the meanings defined herein;
and a saccharide of general formula (II-b)
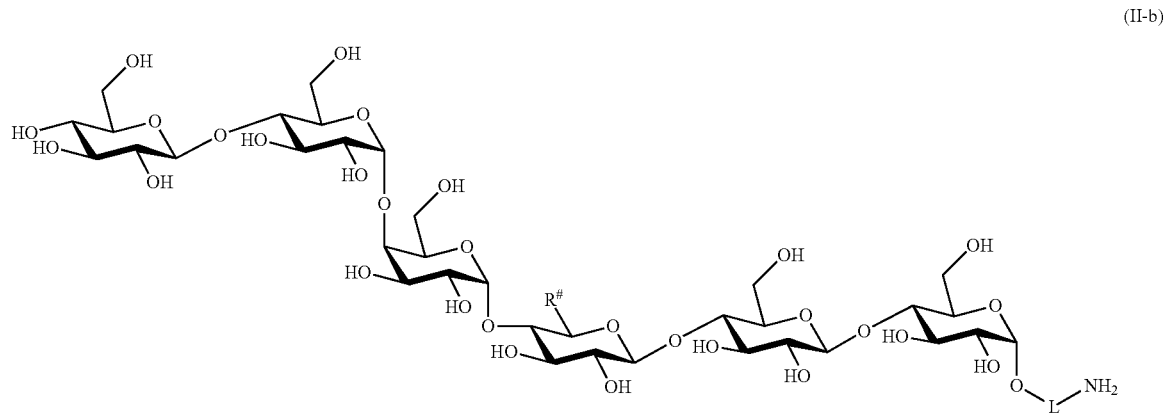
(II-b)
wherein $R^{\#}$ and L have the meanings defined herein;
and a saccharide of general formula (II-c)
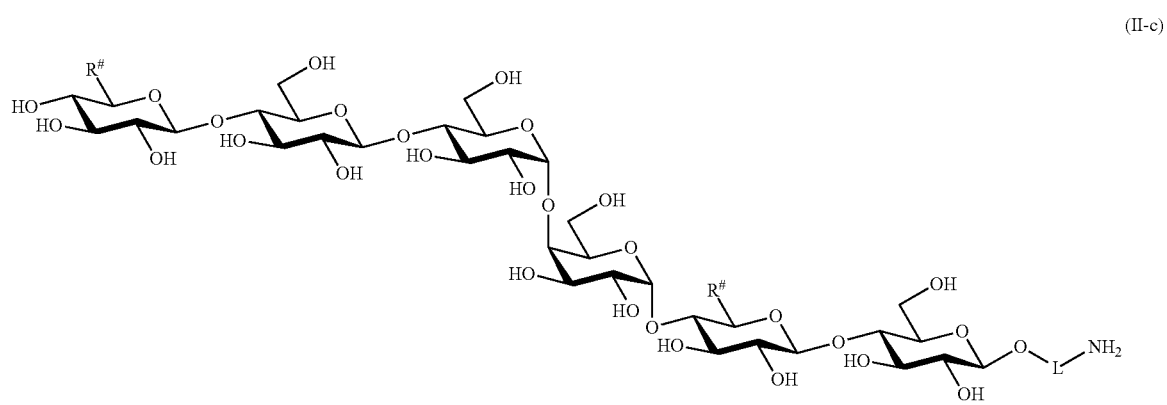
(II-c)

wherein R<sup>#</sup> and L have the meanings defined herein;
and a saccharide of general formula (II-d)

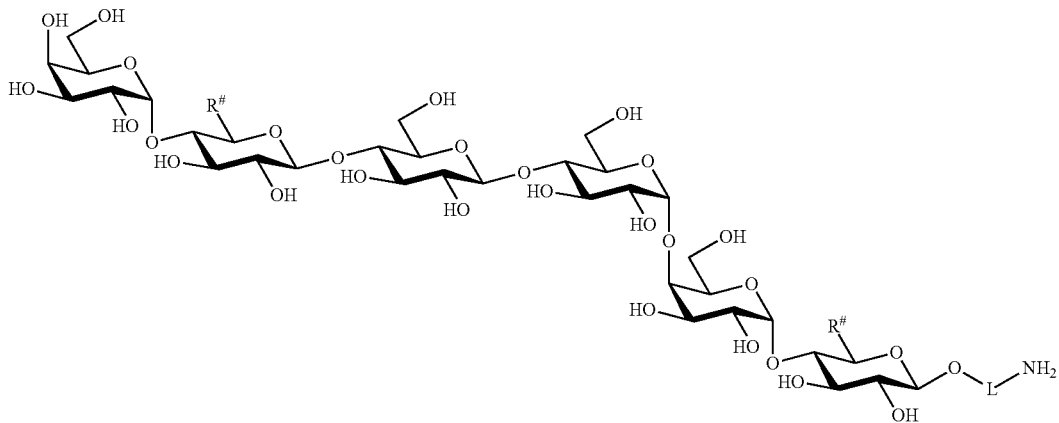
(II-d)

wherein R<sup>#</sup> and L have the meanings defined herein is also preferred.

Another preferred embodiment is directed to a saccharide of general formula (I)

$$V^*—U_{x+3}—U_{x+2}—U_{x+1}—U_x—O\text{-L-NH}_2 \qquad (I)$$

wherein V*— represents H—$U_x$— and x, L, $U_x$, $U_{x+1}$, $U_{x+2}$, $U_{x+3}$ and R<sup>#</sup> have the meanings as defined herein.

Thus, another preferred embodiment is directed to a pentasaccharide of general formula (III)

$$H—U_x—U_{x+3}—U_{x+2}—U_{x+1}—U_x—O\text{-L-NH}_2 \qquad (III)$$

wherein x is an integer selected from 1, 2, 3 and 4;

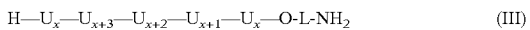

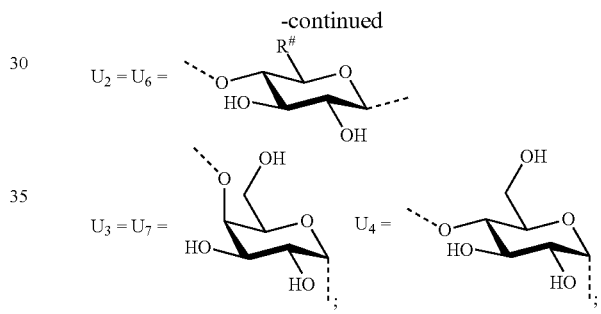

R<sup>#</sup> represents —COOH or —CH$_2$OH;

L represents a linker; or a pharmaceutically acceptable salt thereof.

Preferably, in general formula (III) the residue R<sup>#</sup> represents —COOH.

Thus, a pentasaccharide of general formula (III-a)

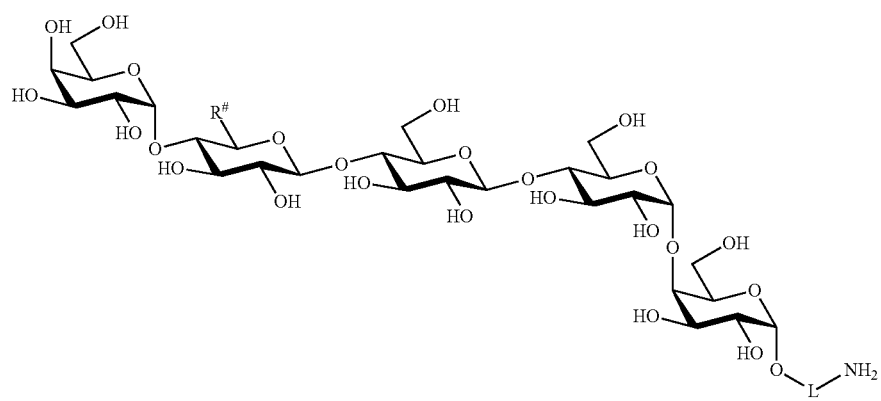
(III-a)

wherein $R^\#$ and L have the meanings defined herein;
and a saccharide of general formula (III-b)

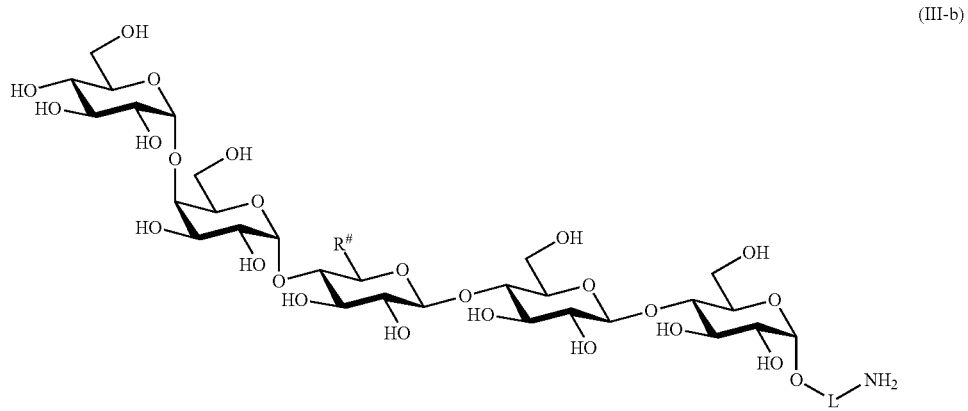

(III-b)

wherein $R^\#$ and L have the meanings defined herein;
and a saccharide of general formula (III-c)

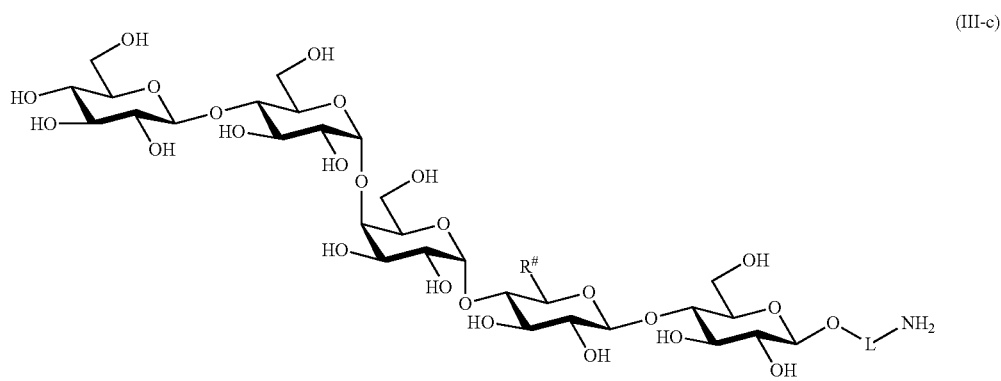

(III-c)

wherein $R^\#$ and L have the meanings defined herein;
and a saccharide of general formula (III-d)

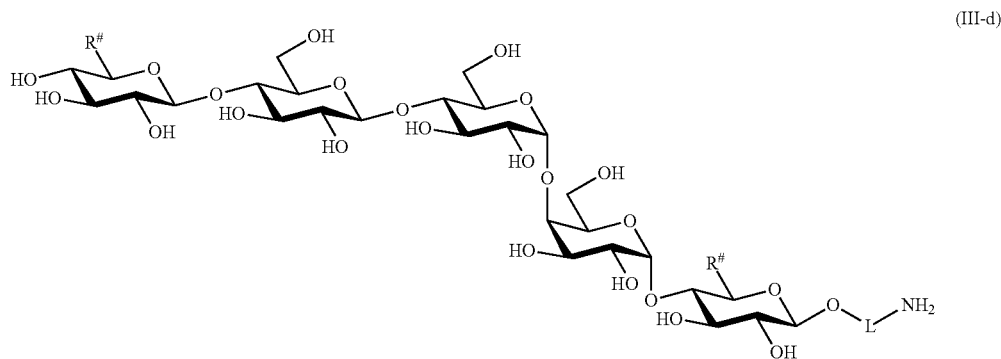

(III-d)

wherein $R^\#$ and L have the meanings defined herein is also preferred.

A further preferred embodiment according to the present invention is directed to a saccharide of general formula (I)

$$V^*-U_{x+3}-U_{x+2}-U_{x+1}-U_x-O-L-NH_2 \quad (I)$$

wherein V*— represents H— and x, L, $U_x$, $U_{x+1}$, $U_{x+2}$, $U_{x+3}$ and $R^\#$ have the meanings as defined herein.

Thus, a further preferred embodiment according to the present invention is directed to a tetrasaccharide of general formula (IV)

   (IV)

wherein x is an integer selected from 1, 2, 3 and 4;

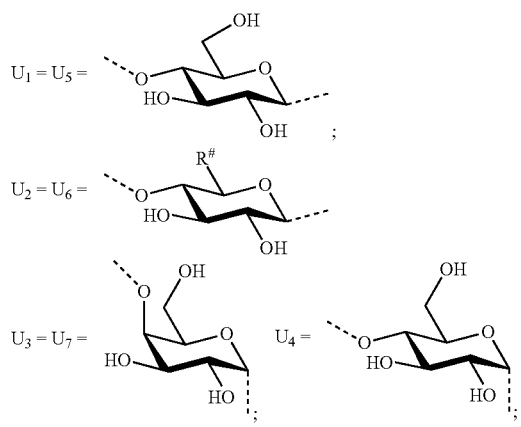

$R^\#$ represents —COOH or —CH$_2$OH;

L represents a linker; or a pharmaceutically acceptable salt thereof.

Preferably, in general formula (III) the residue $R^\#$ represents —COOH.

Thus, a tetrasaccharide of general formula (IV-a)

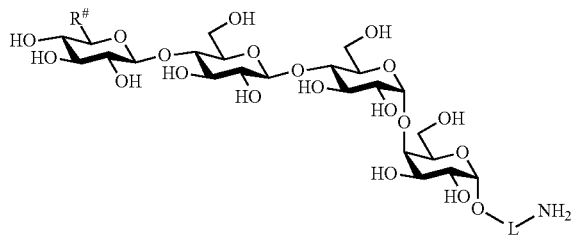   (IV-a)

wherein $R^\#$ and L have the meanings defined herein;
and a saccharide of general formula (IV-b)

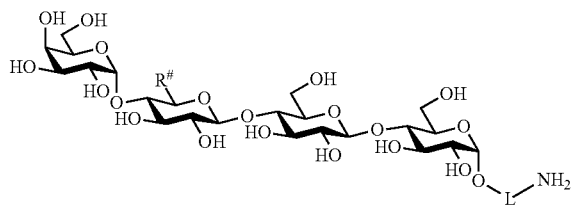   (IV-b)

wherein $R^\#$ and L have the meanings defined herein;
and a saccharide of general formula (IV-c)

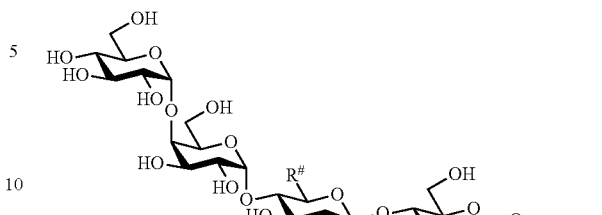   (IV-c)

wherein $R^\#$ and L have the meanings defined herein;
and a saccharide of general formula (IV-d)

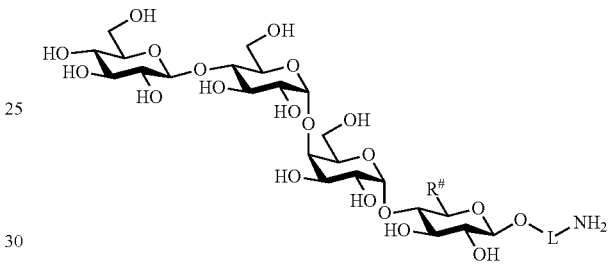   (IV-d)

wherein $R^\#$ and L have the meanings defined herein is also preferred.

Especially preferred is a saccharide of general formula (I), a hexasaccharide of formula (II), a pentasaccharide of formula (III) and a tetrasaccharide of formula (IV) containing the protective immunogenic epitope: β-D-Glpc-(1→4)-α-D-Glcp-(1→4)-α-D-Galp. Thus, hexasaccharide (II-a), (II-c), (II-d), pentasaccharide (III-a), (III-c), (III-d) and tetrasaccharide (IV-a), (IV-d) is especially preferred. Saccharides containing the protective immunogenic epitope β-D-Glpc-(1→4)-α-D-Glcp-(1→4)-α-D-Galp are able to raise high titers of antibodies that recognize selectively *S. pneumoniae* type 8 and opsonize them for killing by phagocytes.

Even more preferred is a saccharide of general formula (I), wherein x represents 3. Hence, a saccharide of general formula (V)

$$V^*\text{—}U_6\text{—}U_5\text{—}U_4\text{—}U_3\text{—}O\text{-}L\text{-}NH_2 \quad (V)$$

wherein

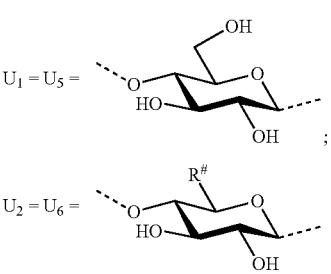

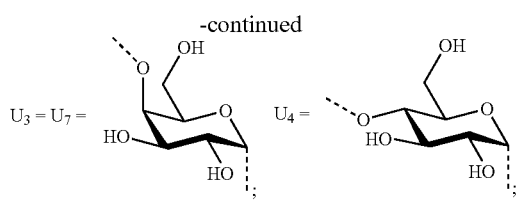

V*— represents H—, H—U$_3$— or H—U$_4$—U$_3$—;
R$^{\#}$ represents —COOH or —CH$_2$OH;

L represents a linker; or a pharmaceutically acceptable salt thereof, is especially preferred. The saccharide of general formula (V) exhibits an extremely robust interaction with human antisera *S. pneumoniae* serotype 8 capsular polysaccharide and murine antibodies raised against *S. pneumoniae* serotype 8 capsular polysaccharide, which are known to protect mice from infection with *S. pneumoniae* type 8 pneumococci. Additionally, the saccharide of general formula (V) elicits antibodies that are cross-reacting with the *S. pneumoniae* serotype 8 capsular polysaccharide, rec Also more preferred is a saccharide of the general formula (V-a)

$$V^*-U_6-U_5-U_4-U_3-O-L^a-L^e-NH_2 \quad (V\text{-}a)$$

wherein
- $-L^a-$ is selected from: $-(CH_2)_o-$, $-(CH_2-CH_2-O)_o-C_2H_4-$, $-(CH_2-CH_2-O)_o-CH_2-$;
- $-L^e-$ is selected from: $-C_2H_4-(O-CH_2-CH_2)_{p1}-$, $-CH_2-(O-CH_2-CH_2)_{p1}-$, $-(CH_2)_{p1}-$, and $-(CH_2)_{p1}-O-(CH_2)_{p2}-$;

$V^*$, o, p1, p2, $U_6$, $U_5$, $U_4$, and $U_3$ have the meanings as defined herein.

Also more preferred is a saccharide of the general formula (VI-a)

$$V^*-U_5-U_4-U_3-U_2-O-L^a-L^e-NH_2 \quad (VI\text{-}a)$$

wherein
- $-L^a-$ is selected from: $-(CH_2)_o-$, $-(CH_2-CH_2-O)_o-C_2H_4-$, $-(CH_2-CH_2-O)_o-CH_2-$;
- $-L^e-$ is selected from: $-C_2H_4-(O-CH_2-CH_2)_{p1}-$, $-CH_2-(O-CH_2-CH_2)_{p1}-$, $-(CH_2)_{p1}-$, and $-(CH_2)_{p1}-O-(CH_2)_{p2}-$;

$V^*$, o, p1, p2, $U_5$, $U_4$, $U_3$, and $U_2$ have the meanings as defined herein.

Still more preferred is a saccharide of the general formula (I-b)

$$V^*-U_{x+3}-U_{x+2}-U_{x+1}-U_x-O-L^a-NH_2 \quad (I\text{-}b)$$

wherein
- $-L^a-$ represents: $-(CH_2)_{o1}-$, $-(CH_2-CH_2-O)_{o2}-C_2H_4-$, $-(CH_2-CH_2-O)_{o2}-CH_2-$;
- o1 is an integer selected from 2, 3, 4, 5 and 6;
- o2 is an integer selected from 1, 2, 3, 4, 5 and 6;

$V^*$, x, $U_x$, $U_{x+1}$, $U_{x+2}$, and $U_{x+3}$ have the meanings as defined herein.

Also more preferred is a saccharide of the general formula (II-f)

$$H-U_{x+1}-U_x-U_{x+3}-U_{x+2}-U_{x+1}-U_x-O-L^a-NH_2 \quad (II\text{-}f)$$

wherein
- $-L^a-$ represents: $-(CH_2)_{o1}-$, $-(CH_2-CH_2-O)_{o2}-C_2H_4-$, $-(CH_2-CH_2-O)_{o2}-CH_2-$;
- o1 is an integer selected from 2, 3, 4, 5 and 6;
- o2 is an integer selected from 1, 2, 3, 4, 5 and 6;

x, $U_x$, $U_{x+1}$, $U_{x+2}$, and $U_{x+3}$ have the meanings as defined herein.

Also more preferred is a saccharide of the general formula (III-f)

$$H-U_x-U_{x+3}-U_{x+2}-U_{x+1}-U_x-O-L^a-NH_2 \quad (III\text{-}f)$$

wherein
- $-L^a-$ represents: $-(CH_2)_{o1}-$, $-(CH_2-CH_2-O)_{o2}-C_2H_4-$, $-(CH_2-CH_2-O)_{o2}-CH_2-$;
- o1 is an integer selected from 2, 3, 4, 5 and 6;
- o2 is an integer selected from 1, 2, 3, 4, 5 and 6;

x, $U_x$, $U_{x+1}$, $U_{x+2}$, and $U_{x+3}$ have the meanings as defined herein.

Also more preferred is a saccharide of the general formula (IV-f)

$$H-U_{x+3}-U_{x+2}-U_{x+1}-U_xO-L^a-NH_2 \quad (IV\text{-}f)$$

wherein
- $-L^a-$ represents: $-(CH_2)_{o1}-$, $-(CH_2-CH_2-O)_{o2}-C_2H_4-$, $-(CH_2-CH_2-O)_{o2}-CH_2-$;
- o1 is an integer selected from 2, 3, 4, 5 and 6;
- o2 is an integer selected from 1, 2, 3, 4, 5 and 6;

x, $U_x$, $U_{x+1}$, $U_{x+2}$, and $U_{x+3}$ have the meanings as defined herein.

Also more preferred is a saccharide of the general formula (V-b)

$$V^*-U_6-U_5-U_4-U_3-O-L^a-NH_2 \quad (V\text{-}b)$$

wherein
- $-L^a-$ represents: $-(CH_2)_{o1}-$, $-(CH_2-CH_2-O)_{o2}-C_2H_4-$, $-(CH_2-CH_2-O)_{o2}-CH_2-$;
- o1 is an integer selected from 2, 3, 4, 5 and 6;
- o2 is an integer selected from 1, 2, 3, 4, 5 and 6;

$V^*$, $U_6$, $U_5$, $U_4$, and $U_3$ have the meanings as defined herein.

Also more preferred is a saccharide of the general formula (VI-b)

$$V^*-U_5-U_4-U_3-U_2-O-L^a-NH_2 \quad (VI\text{-}b)$$

wherein
- $-L^a-$ represents: $-(CH_2)_{o1}-$, $-(CH_2-CH_2-O)_{o2}-C_2H_4-$, $-(CH_2-CH_2-O)_{o2}-CH_2-$;
- o1 is an integer selected from 2, 3, 4, 5 and 6;
- o2 is an integer selected from 1, 2, 3, 4, 5 and 6;

$V^*$, $U_5$, $U_4$, $U_3$, and $U_2$ have the meanings as defined herein.

Still more preferred is a saccharide of the general formula (I-c)

$$V^*-U_{x+3}-U_{x+2}-U_{x+1}-U_x-O-(CH_2)_o-NH_2 \quad (I\text{-}C)$$

wherein
o is an integer selected from 2, 3, 4, 5 and 6;
$V^*$, x, $U_x$, $U_{x+1}$, $U_{x+2}$, and $U_{x+3}$ have the meanings as defined herein.

Also more preferred is a saccharide of the general formula (II-g)

$$H-U_{x+1}-U_x-U_{x+3}-U_{x+2}-U_{x+1}-U_x-O-(CH_2)_o-NH_2 \quad (II\text{-}g)$$

wherein
o is an integer selected from 2, 3, 4, 5 and 6;
x, $U_x$, $U_{x+1}$, $U_{x+2}$, and $U_{x+3}$ have the meanings as defined herein.

Also more preferred is a saccharide of the general formula (III-g)

$$H-U_x-U_{x+3}-U_{x+2}-U_{x+1}-U_x-O-(CH_2)_o-NH_2 \quad (III\text{-}g)$$

wherein
o is an integer selected from 2, 3, 4, 5 and 6;
x, $U_x$, $U_{x+1}$, $U_{x+2}$, and $U_{x+3}$ have the meanings as defined herein.

Also more preferred is a saccharide of the general formula (IV-g)

$$H-U_{x+3}-U_{x+2}-U_{x+1}-U_x-O-(CH_2)_o-NH_2 \quad (IV\text{-}g)$$

wherein
o is an integer selected from 2, 3, 4, 5 and 6;
x, $U_x$, $U_{x+1}$, $U_{x+2}$, and $U_{x+3}$ have the meanings as defined herein.

Also more preferred is a saccharide of the general formula (V-c)

$$V^*-U_6-U_5-U_4-U_3-O-(CH_2)_o-NH_2 \quad (V\text{-}c)$$

wherein
o is an integer selected from 2, 3, 4, 5 and 6;
$V^*$, $U_6$, $U_5$, $U_4$, and $U_3$ have the meanings as defined herein.

Also more preferred is a saccharide of the general formula (VI-c)

$$V^*-U_5-U_4-U_3-U_2-O-(CH_2)_o-NH_2 \quad (VI\text{-}c)$$

wherein
o is an integer selected from 2, 3, 4, 5 and 6;
$V^*$, $U_5$, $U_4$, $U_3$, and $U_2$ have the meanings as defined herein.

In yet another preferred embodiment, the saccharide according to the present invention is selected from the group consisting of:

α-D-glucopyranosyl-(1→4)-α-D-galactopyranosyl-(1→4)-β-D-glucopyranosyluronic acid-(1→4)-β-D-glucopyranosyl-(1→1)-(2-amino)ethanol (10), β-D-glucopyranosyluronic acid-(1→4)-β-D-glucopyranosyl-(1→4)-α-D-glucopyranosyl-(1→4)-α-D-galactopyranosyl-(1→1)-(2-amino)ethanol (18), 5-amino pentanyl β-D-glucopyranosyl uronic acid-(1→4)-β-D-glucopyranosyl-(1→4)-α-D-glucopyranosyl-(1→4)-α-D-galactopyranoside (19), 5-amino pentanyl β-D-glucopyranosyl-(1→4)-β-D-glucopyranosyl-(1→4)-α-D-glucopyranosyl-(1→4)-α-D-galactopyranoside (60), 5-amino pentanyl α-D-galactopyranosyl-(1→4)-β-D-glucopyranosyluronic acid-(1→4)-β-D-glucopyranosyl-(1→4)-α-D-glucopyranoside (20), 5-amino pentanyl α-D-glucopyranosyl-(1→4)-α-D-galactopyranosyl-(1→4)-β-D-glucopyranosyluronic acid-(1→4)-β-D-glucopyranoside (21), 5-amino pentanyl β-D-glucopyranosyl-(1→4)-β-D-glucopyranosyl-(1→4)-α-D-galactopyranosyl-(1→4)-β-D-glucopyranosyl uronic acid (22), α-D-galactopyranosyl-(1→4)-β-D-glucopyranosyluronate-(1→4)-β-D-glucoyranosyl-α-D-glucopyranosyl-(1→4)-α-D-galactopyranosyl-(1→1)-(2-amino)ethanol (55), α-D-glucopyranosyl-(1→4)-α-D-galactopyranosyl-(1→4)-β-D-glucopyranosyluronate-(1→4)-β-D-glucoyranosyl-(1→4)-α-D-glucopyranosyl-(1→4)-α-D-galactopyranosyl-(1→1)-(2-amino)ethanol (57);

5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranosyl-(1→4)-α-D-galactopyranoside (63);

5-amino pentanyl galactopyranosyl-(1→4)-α-D-glucopyranosyl-(1→4)-α-D-galactopyranosyl-(1→4)-β-D-glucopyranosyluronic acid-(1→4)-β-D-glucopyranosyl-(1→4)-α-D-glucopyranoside (64);

5-amino pentanyl β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid-(1→4)-β-D-glucopyranoside (65) ;

5-amino pentanyl α-D-galactopyranosyl-(1→4)-β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid (66);

5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranosyl-(1→4)-α-D-galactopyranoside (67);

5-amino pentanyl β-D-glucopyranosyl-(1→4)-α-D-glucopyranosyl-(1→4)-α-D-galactopyranosyl-(1→4)-β-D-glucopyranosyl-(1→4)-β-D-glucopyranosyl-(1→4)-α-D-glucopyranoside (68);

5-amino pentanyl β-D-glucopyranosyl-(1→4)-β-D-glucopyranosyl-(1→4)-α-D-glucopyranosyl-(1→4)-α-D-galactopyranosyl-(1→4)-β-D-glucopyranosyl-(1→4)-β-D-glucopyranoside (69);

5-amino pentanyl α-D-galactopyranosyl-(1→4)-β-D-glucopyranosyl-(1→4)-α-D-glucopyranosyl-(1→4)-α-D-glucopyranosyl-(1→4)-α-D-galactopyranosyl-(1→4)-β-D-glucopyranoside (70);

3-aminopropyl α-D-galactopyranosyl-(1→4)-β-D-glucopyranosyluronic acid-(1→4)-β-D-glucopyranosyl-(1→4)-α-D-glucopyranosyl-(1→4)-α-D-galactopyranoside (71);

5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranoside (72);

3-aminopropyl β-D-glucopyranosyl-(1→4)-α-D-gl ucopyranosyl-(1→4)-α-D-galactopyranosyl-(1→4)-β-D-glucopyranosyluronic acid-(1→4)-β-D-glucopyranoside (73);

5-amino pentanyl β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid (74);

4-aminobutyl α-D-galactopyranosyl-(1→4)-β-D-glucopyranosyl-(1→4)-β-D-glucopyranosyl-(1→4)- α-D-glucopyranosyl-(1→4-α-D-galactopyranoside (75);

6-amino hexanyl α-D-glucopyranosyl-(1→4)-α-D-galactopyranosyl-(1→4)-β-D-glucopyranosyl-(1→4)-β-D-glucopyranosyl-(1→4)-α-D-glucopyranoside (76);

3-aminopropyl β-D-glucopyranosyl-(1→4)-α-D-glucopyranosyl-(1→4)-α-D-galactopyranosyl-(1→4)-β-D-glucopyranosyl-(1→4)-β-D-glucopyranoside (77);

5-amino pentanyl β-D-glucopyranosyl-(1→4)-β-D-glucopyranosyl-(1→4)-α-D-glucopyranosyl-(1→4)-α-D-galactopyranosyl-(1→4)-β-D-glucopyranoside (78);

4-aminobutyl α-D-galactopyranosyl-(1→4)-β-D-glucopyranosyl-(1→4)-β-D-glucopyranosyl-(1→4)-α-D-glucopyranoside (79);

3-aminopropyl α-D-glucopyranosyl-(1→4)-α-D-galactopyranosyl-(1→4)-β-D-glucopyranosyl-(1→4)-β-D-glucopyranoside (80);

6-amino hexanyl β-D-glucopyranosyl-(1→4)-α-D-glucopyranosyl-(1→4)-α-D-galactopyranosyl-(1→4)-β-D-glucopyranoside (81).

Surprisingly, it was further found that a pure saccharide of general formula (VII) contains the protective immunogenic glycan epitope β-D-Glcp-(1→4)-α-D-Glcp-(1→4)-α-D-Galp and is able to induce a protective immune response against *S. pneumoniae* serotype 8 bacteria in a human and/or animal host. The saccharide of general formula (VII) containing the protective immunogenic glycan epitope β-D-Glcp-(1→4)-α-D-Glcp-(1→4)-α-D-Galp elicits antibodies that are cross-reacting with the *S. pneumoniae* serotype 8 capsular polysaccharide, recognize specifically *S. pneumoniae* serotype 8 bacteria and opsonize them for killing by phagocytes.

Thus, another aspect of the present invention is directed to a saccharide of general formula (VII)

$$S^*—U_5—U_4—U_3—S—O-L-NH_2 \quad (VII)$$

wherein

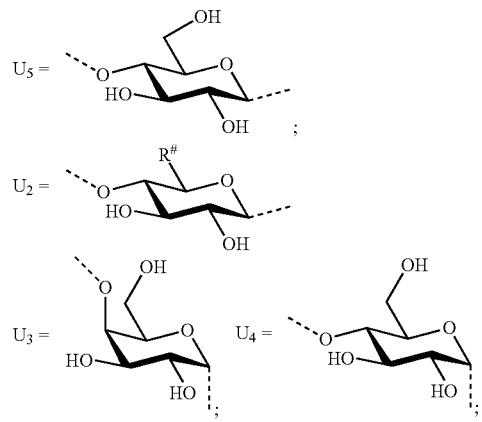

R# represents —COOH or —CH₂OH;
—S— represents —S$_a$— or —S$_b$—;
—S$_a$— represents —(U₅)$_{n1}$—, —(U₅—U₄)$_{n2}$— or —(U₅—U₄—U₃)$_{n3}$—;
—S$_b$— represents —(U₂)$_{n1}$—, —(U₂—U₅)$_{n2}$— or —(U₂—U₅—U₄)$_{n3}$—;
S*— represents S*$_a$— or S*$_b$—;
S*$_a$— represents H—(U₃)$_{n4}$— or H—(U₄—U₃)$_{n5}$—;
S*$_b$— represents H—(U₂)$_{n4}$—, H—(U₃—U₂)$_{n5}$— or H—(U₄—U₃—U₂)$_{n6}$—;
n1, n2, n3, n4, n5 and n6 are selected from 0 and 1;
L is a linker;
with the proviso that
if —S— represents —S$_a$—, then S*— represents S*$_a$—; and
if —S— represents —S$_b$—, then S*— represents S*$_b$—; and
if n1=1, then n6=0; and
if n2=1, then n5=n6=0; and
if n3=1, then n4=n5=n6=0; and
if n4=1, then n3=0; and
if n5=1, then n2=n3=0; and
if n6=1, then n1=n2=n3=0;
or a pharmaceutically acceptable salt thereof.

-L- is defined as a linker and is part of the fragment —O-L-NH₂. Thus, the linker -L- is bound to an oxygen atom and to the nitrogen atom of the NH₂-group. It is preferred that at least two carbon atoms of the linker are between the oxygen atom and the NH₂-group, like —O—C—C—NH₂. The linker L can be an aliphatic chain, wherein the aliphatic chain can optionally include an aromatic chain inserted in it, or a number of heteroatoms oscillating from 0 to 10.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-NH₂) and the NH₂-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the NH₂-group) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably two substituents such as R¹⁰ and R¹¹ or four substituents such as R¹⁰, R¹¹, R¹⁵ and R¹⁴, which have the meanings as defined herein and which are preferably selected from: —F, —Cl, —CH₃, —C₂H₅, —C₃H₇, —C₅H₉, —C₆H₁₃, —OCH₃, —OC₂H₅, —CH₂F, —CHF₂, —CF₃, —C(O)—NH₂, —SCH₃, —SC₂H₅, —NHC(O)CH₃, —N(CH₃)₂, and —N(C₂H₅)₂;

In case the linker -L- is fluorinated, more than two substituents —F are preferred.

Preferably the linker -L- is selected from: —CH₂—, —(CH₂)₂—, —(CH₂)₃—, —(CH₂)₄—, —(CH₂)₅—, —(CH₂)₆—, —(CH₂)₇—, —(CH₂)₈—, —(CH₂)₉—, —(CH₂)₁₀—, —CF₂—, —(CF₂)₂—, —(CF₂)₃—, —(CF₂)₄—, —(CF₂)₅—, —(CF₂)₆—, —(CF₂)₇—, —(CF₂)₈—, —(CF₂)₉—, —(CF₂)₁₀—, —(CH₂)₂—O—(CH₂)₂—, —CH₂—O—(CH₂)₃—, —(CH₂)₃—O—CH₂—, —CH₂—O—(CH₂)₂—, —(CH₂)₂—O—CH₂—, —(CH₂)₃—O—(CH₂)₂—, —(CH₂)₂—O—(CH₂)₃—, —(CH₂)₄—O—CH₂—, —CH₂—O—(CH₂)₄—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$;

wherein
-L$^a$- is selected from: —(CH₂)$_o$—, —(CF₂)$_o$—, —(CH₂—CH₂—O)$_o$—C₂H₄—, —(CH₂—CH₂—O)$_o$—CH₂—, —(CR¹⁰R¹¹)$_o$—,

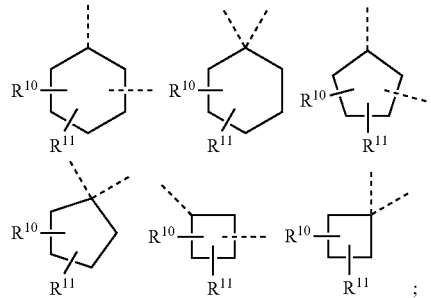

-L$^b$- and -L$^c$- are independently of each other selected from:
—O—, —NH—C(O)—NH—, —NH—C(S)—NH—, —NH—C(O)—, —C(O)—NH—, —NH—C(O)—O—, —NR⁹—, —NR¹⁸—, —SO₂—,

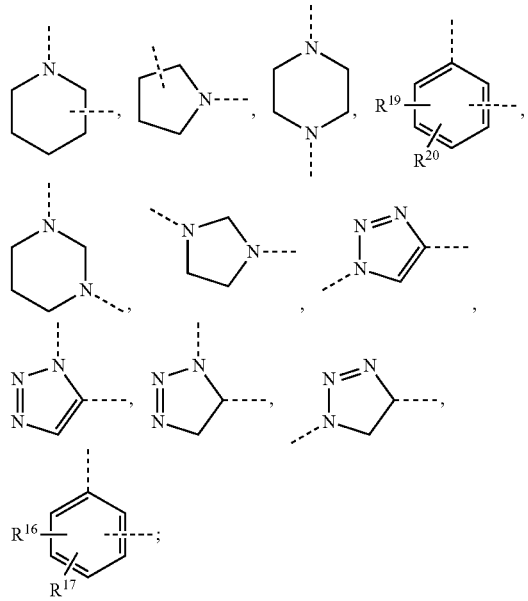

-L$^d$- represents —(CH₂)$_q$—, —CF₂)$_q$—, —(CR¹²R¹³)$_q$—, —(CH₂—CH₂—O)$_q$—C₂H₄—, —(CH₂—CH₂—O)$_q$—CH₂—,

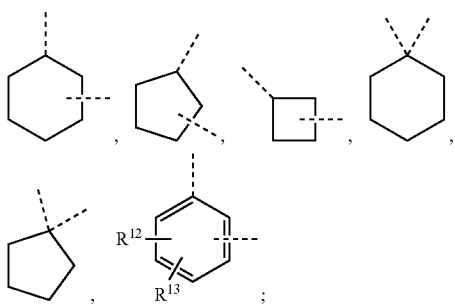

-L$^e$- is selected from: —(CH$_2$)$_{p1}$—, —(CF$_2$)$_{p1}$—, —C$_2$H$_4$— (O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

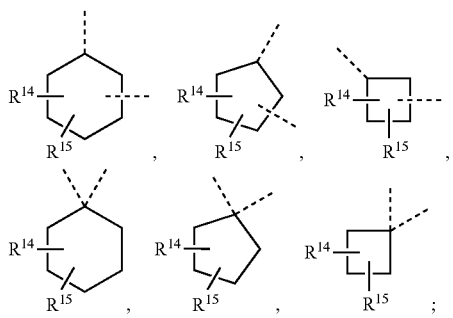

R$^9$ and R$^{18}$ are independently of each other selected from: —CH$_3$, —C$_2$H$_5$, —C$_3$H$_7$, and —C(O)CH$_3$;
R$^{10}$, R$^{11}$, R$^{12}$, R$^{13}$, R$^{14}$, R$^{15}$, R$^{16}$, R$^{17}$, R$^{19}$, R$^{20}$, R$^{21}$ and R$^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$;
o, q, p1 and p2 are independently of each other an integer selected from 1, 2, 3, 4, 5, 6, 7, 8, 9, and 10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

It is clear for the skilled person in the art of carbohydrate chemistry that the saccharides of general (VII) are not containing —O—O— bonds and or sugar fragments (U$_2$, U$_3$, U$_4$, U$_5$) connected or bound to each other via their anomeric or C-1 carbons. It is also clear for the person skilled in the art that the stereochemistry of the glycosidic bond is the stereochemistry indicated for the anomeric centre of the sugar fragment in the general formula. Hence, the stereochemistry of the anomeric centre for sugar fragment U$_1$ and U$_5$ is β, for sugar fragment U$_2$ and U$_6$ is β, for sugar fragment U$_3$ and U$_7$ is α and for sugar fragment U$_4$ is α.

Preferred is a saccharide of general formula (VII), wherein —S— represents —S$_a$— and S*— represents S*$_a$—. Thus, a saccharide of general formula (VIII)

$$S_a^*—U_5—U_4—U_3—S_a—O-L-NH_2 \qquad (VIII)$$

wherein

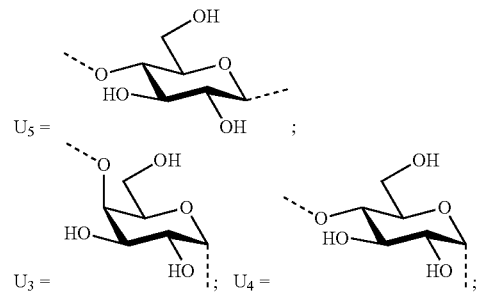

—S$_a$— represents —(U$_5$)$_{n1}$—, —(U$_5$—U$_4$)$_{n2}$— or —(U$_5$—U$_4$—U$_3$)$_{n3}$—;
S*$_a$— represents H—(U$_3$)$_{n4}$— or H—(U$_4$—U$_3$)$_{n5}$—;
n1, n2, n3, n4 and n5 are selected from 0 and 1;
L is a linker;
with the proviso that
if n2=1, then n5=0; and
if n3=1, then n4=n5=0; and
if n4=1, then n3=0; and
if n5=1, then n2=n3=0;
or a pharmaceutically acceptable salt thereof is also preferred.

Especially preferred is a saccharide of general formula (VII), wherein —S— represents —S$_b$— and S*— represents S*$_b$—. Hence, a saccharide of general formula (IX)

$$S_b^*—U_5—U_4—U_3—S_b—O-L-NH_2 \qquad (IX)$$

wherein

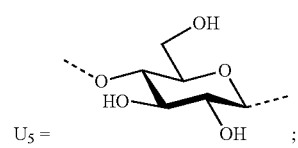

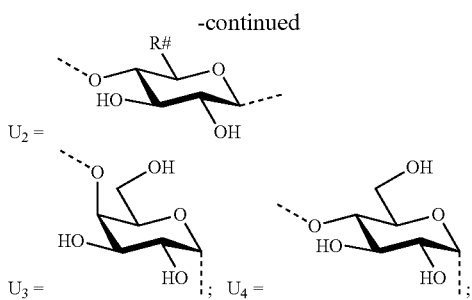

$R^{\#}$ represents —COOH or —CH$_2$OH;

—S$_b$— represents —(U$_2$)$_{n1}$—, —(U$_2$—U$_5$)$_{n2}$— or —(U$_2$—U$_5$—U$_4$)$_{n3}$—;

S*$_b$— represents H—(U$_2$)$_{n4}$—, H—(U$_3$—U$_2$)$_{n5}$— or H—(U$_4$—U$_3$—U$_2$)$_{n6}$—;

n1, n2, n3, n4, n5 and n6 are selected from 0 and 1;

L is a linker;

with the proviso that if n1=1, then n6=0; and if n2=1, then n5=n6=0; and if n3=1, then n4=n5=n6=0; and if n4=1, then n3=0; and if n5=1, then n2=n3=0; and if n6=1, then n1=n2=n3=0;

or a pharmaceutically acceptable salt thereof,

Preferably the linker -L- is selected from: -L$^a$-, -L$^a$-L$^e$-, -L$^a$-L$^b$-L$^e$-, -L$^a$-L$^d$-L$^e$-; wherein -L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;

-L$^b$- represents —O—;

-L$^d$- is selected from —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;

and o, q, p1 and p2 are independently of each other an integer selected from 1, 2, 3, 4, 5, and 6.

Therefore, a saccharide of general formula (VII), (VIII) or (IX) wherein

-L- is selected from: -L$^a$-, -L$^a$-L$^e$-, -L$^a$-L$^b$-L$^e$- and -L$^a$-L$^d$-L$^e$-;

-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;

-L$^b$- represents —O—;

-L$^d$- is selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;

and o, q, p1 and p2 are independently of each other an integer selected from 1, 2, 3, 4, 5, and 6 is especially preferred.

Even more preferred is a saccharide of general formula (VII), (VIII) or (IX) wherein -L- represents —(CH$_2$)$_o$— and o is an integer selected from 2, 3, 4, 5 and 6.

Still more preferred is a saccharide of the general formula (VII-a)

$$S^*—U_5—U_4—U_3—S—O-L^a-L^e-NH_2 \qquad \text{(VII-a)}$$

wherein

-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;

-L$^e$- is selected from: —C$_2$H$_4$—(O—CH$_2$—CH$_2$)$_{p1}$—, —CH$_2$—(O—CH$_2$—CH$_2$)$_{p1}$—(CH$_2$)$_{p1}$—, and —(CH$_2$)$_{p1}$—O—(CH$_2$)$_{p2}$—;

S*, S, o, p1, p2, U$_5$, U$_4$, and U$_3$ have the meanings as defined herein.

Also more preferred is a saccharide of the general formula (VIII-a)

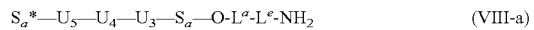

$$S_a^*—U_5—U_4—U_3—S_a—O-L^a-L^e-NH_2 \qquad \text{(VIII-a)}$$

wherein

-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;

-L$^e$- is selected from: —C$_2$H$_4$—(O—CH$_2$—CH$_2$)$_{p1}$—, —CH$_2$—(O—CH$_2$—CH$_2$)$_{p1}$—(CH$_2$)$_{p1}$—, and —(CH$_2$)$_{p1}$—O—(CH$_2$)$_{p2}$—;

S$_a$*, S$_a$, o, p1, p2, U$_5$, U$_4$, and U$_3$ have the meanings as defined herein.

Also more preferred is a saccharide of the general formula (IX-a)

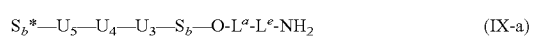

$$S_b^*—U_5—U_4—U_3—S_b—O-L^a-L^e-NH_2 \qquad \text{(IX-a)}$$

wherein

-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;

-L$^e$- is selected from: —C$_2$H$_4$—(O—CH$_2$—CH$_2$)$_{p1}$—, —CH$_2$—(O—CH$_2$—CH$_2$)$_{p1}$—(CH$_2$)$_{p1}$—, and —(CH$_2$)$_{p1}$—O—(CH$_2$)$_{p2}$—;

S$_b$*, S$_b$, o, p1, p2, U$_5$, U$_4$, and U$_3$ have the meanings as defined herein.

Still more preferred is a saccharide of the general formula (VII-b)

$$S^*—U_5—U_4—U_3—S—O-L^a-NH_2 \qquad \text{(VII-b)}$$

wherein

-L$^a$- represents: —(CH$_2$)$_{o1}$—, —(CH$_2$—CH$_2$—O)$_{o2}$—C$_2$H$_4$—, —(CH$_2$—CH$_2$—O)$_{o2}$—CH$_2$—;

o1 is an integer selected from 2, 3, 4, 5 and 6;

o2 is an integer selected from 1, 2, 3, 4, 5 and 6;

S*, S, U$_5$, U$_4$, and U$_3$ have the meanings as defined herein.

Also more preferred is a saccharide of the general formula (VIII-b)

$$S_a^*—U_5—U_4—U_3—S_a—O-L^a-NH_2 \qquad \text{(VIII-b)}$$

wherein

-L$^a$- represents: —(CH$_2$)$_{o1}$—, —(CH$_2$—CH$_2$—O)$_{o2}$—C$_2$H$_4$—, —(CH$_2$—CH$_2$—O)$_{o2}$—CH$_2$—;

o1 is an integer selected from 2, 3, 4, 5 and 6;

o2 is an integer selected from 1, 2, 3, 4, 5 and 6;

S$_a$*, S$_a$, U$_5$, U$_4$, and U$_3$ have the meanings as defined herein.

Also more preferred is a saccharide of the general formula (IX-b)

$$S_b^*—U_5—U_4—U_3—S_b—O-L^a-NH_2 \qquad \text{(IX-b)}$$

wherein

-L$^a$- represents: —(CH$_2$)$_{o1}$—, —(CH$_2$—CH$_2$—O)$_{o2}$—C$_2$H$_4$—, —(CH$_2$—CH$_2$—O)$_{o2}$—CH$_2$—;

o1 is an integer selected from 2, 3, 4, 5 and 6;

o2 is an integer selected from 1, 2, 3, 4, 5 and 6;

S$_b$*, S$_b$, U$_5$, U$_4$, and U$_3$ have the meanings as defined herein.

Still more preferred is a saccharide of the general formula (VII-c)

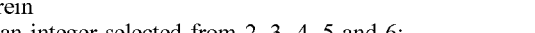

$$S^*—U_5—U_4—U_3—S—O—(CH_2)_o—NH_2 \qquad \text{(VII-c)}$$

wherein o is an integer selected from 2, 3, 4, 5 and 6;

S*, S, U$_5$, U$_4$, and U$_3$ have the meanings as defined herein.

Also more preferred is a saccharide of the general formula (VIII-c)

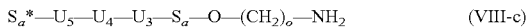
$$S_a{}^*—U_5—U_4—U_3—S_a—O—(CH_2)_o—NH_2 \quad (VIII\text{-}c)$$

wherein
o is an integer selected from 2, 3, 4, 5 and 6;
$S_a{}^*$, $S_a$, $U_5$, $U_4$, and $U_3$ have the meanings as defined herein.

Also more preferred is a saccharide of the general formula (IX-c)

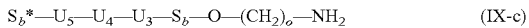
$$S_b{}^*—U_5—U_4—U_3—S_b—O—(CH_2)_o—NH_2 \quad (IX\text{-}c)$$

wherein
o is an integer selected from 2, 3, 4, 5 and 6;
$S_b{}^*$, $S_b$, $U_5$, $U_4$, and $U_3$ have the meanings as defined herein.

In yet another preferred embodiment, the saccharide according to the present invention is elected from the group consisting of:

β-D-glucopyranosyl-(1→4)-β-D-glucopyranosyl-(1→4)-α-D-glucopyranosyl-(1→4)-α-D-galactopyranosyl-(1→1)-(2-amino)ethanol (60), β-D-glucopyranosyluronic acid-(1→4)-β-D-glucopyranosyl-(1→4)-α-D-glucopyranosyl-(1→4)-α-D-galactopyranosyl-(1→1)-(2-amino)ethanol (18), 5-amino pentanyl β-D-glucopyranosyl uronic acid-(1→4)-β-D-glucopyranosyl-(1→4)-α-D-glucopyranosyl-(1→4)-α-D-galactopyranoside (19), β-D-Glucoyranosyl-(1→4)-α-D-glucopyranosyl-(1→4)-α-D-galactopyranosyl-(1→1)-(2-amino)ethanol (62), 5-amino pentanyl β-D-glucopyranosyl-(1→4)-α-D-glucopyranosyl-(1→4)-α-D-galactopyranosyl-(1→4)-β-D-glucopyranosyl uronic acid (22), α-D-galactopyranosyl-(1→4)-β-D-glucopyranosyluronate-(1→4)-β-D-glucoyranosyl-α-D-glucopyranosyl-(1→4)-α-D-galactopyranosyl-(1→1)-(2-amino)ethanol (55), α-D-glucopyranosyl-(1→4)-α-D-galactopyranosyl-(1→4)-β-D-glucopyranosyluronate-(1→4)-β-D-glucoyranosyl-(1→4)-α-D-glucopyranosyl-(1→4)-α-D-galactopyranosyl-(1→1)-(2-amino)ethanol (57).

4-amino butyl β-D-glucopyranosyl-(1→4)-α-D-glucopyranosyl-(1→4)-α-D-galactopyranosyl-(1→4)-β-D-glucopyranosyl -(1→4)-α-D-glucopyranosyl-(1→4)-α-D-galactopyranoside (82);

3-aminopropyl α-D-galactopyranosyl-(1→4)-β-D-glucopyranosyl-(1→4)-α-D-glucopyranosyl-(1→4)-α-D-galactopyranosyl-(1→4)-β-D-glucopyranosyl-(1→4)-α-D-glucopyranoside (83);

3-aminopropyl α-D-glucopyranosyl-(1→4)-α-D-galactopyranosyl-(1→4)-β-D-glucopyranosyl-(1→4)-α-D-glucopyranosyl-(1→4)-α-D-galactopyranosyl-(1→4)-β-D-glucopyranoside (84);

6-amino hexanyl α-D-galactopyranosyl-(1→4)-β-D-glucopyranosyl-(1→4)-α-D-glucopyranosyl-(1→4)-α-D-galactopyranosyl-(1→4)-β-D-glucopyranoside (85);

3-aminopropyl α-D-glucopyranosyl-(1→4)-α-D-galactopyranosyl-(1→4)-β-D-glucopyranosyl-(1→4)-α-D-glucopyranosyl-(1→4-α-D-galactopyranoside (86);

4-aminobutyl β-D-glucopyranosyl-(1→4)-α-D-glucopyranosyl-(1→4)-α-D-galactopyranosyl-(1→4)-β-D-glucopyranosyl-(1→4)-α-D-glucopyranoside (87);

4-aminobutyl β-D-glucopyranosyl-(1→4)-α-D-glucopyranosyl-(1→4)-α-D-galactopyranosyl-(1→4)-β-D-glucopyranoside (88);

6-aminohexanyl α-D-galactopyranosyl-(1→4)-β-D-glucopyranosyl-(1→4)-α-D-glucopyranosyl-(1→4)-α-D-glucopyranoside (89).

Chemical Synthesis

A saccharide according to the present invention can be synthesized via several synthetic routes.

For example, a saccharide according to the present invention can be assembled starting from thioglycoside building blocks BB2 (precursor for the sugar fragment $U_1$, $U_5$, $U_2$ and $U_6$), BB3 (precursor for the sugar fragment $U_2$ and $U_6$), BB4 (precursor for the sugar fragment $U_3$ and $U_7$) and BB5 (precursor for the sugar fragment $U_4$) and functionalized solid support BB1 (*Angew. Chem. Int. Ed.* 2013, 52, 5858.) (see Scheme 1) by automated solid phase synthesis.

The synthetic process, which is summarized in Scheme 1 involves:

assembly of the desired oligosaccharide, which includes glycosylation with the appropriate thioglycoside (BB2, BB3, BB4 or BB5) by activation with NIS/TfOH; followed by removal of the temporary protecting group Fmoc by treatment with $Et_3N$;

cleavage from the solid support; and removal of the permanent protecting groups.

Scheme 1: Automated solid phase syntheseis of saccharides of general formula (I).

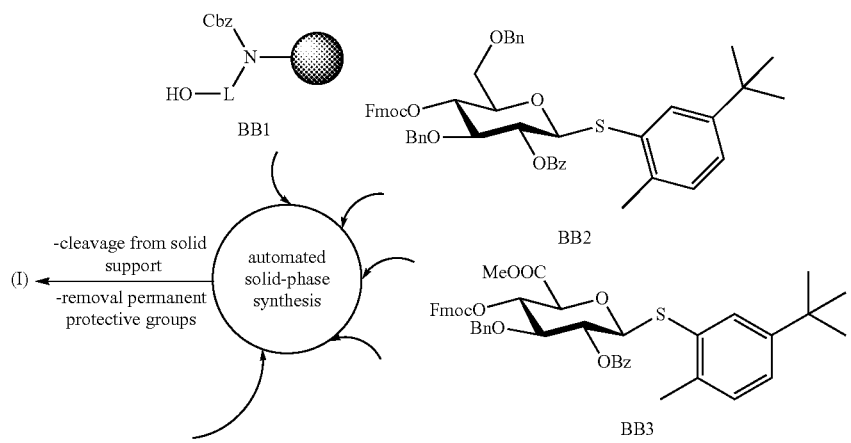

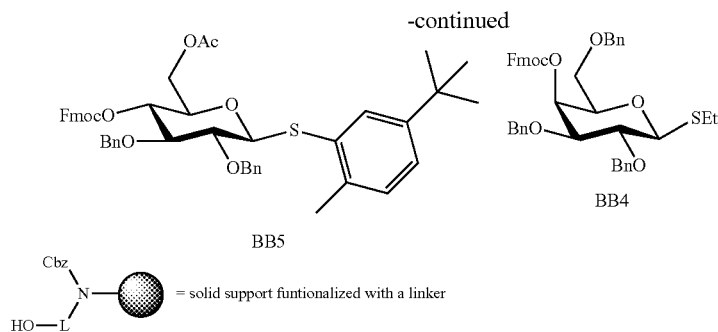

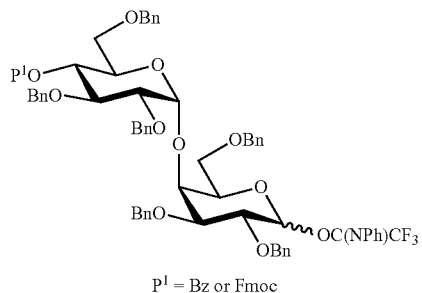

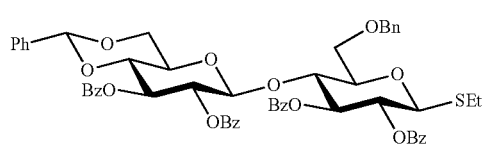

Alternatively, solution-phase synthesis of oligosaccharides can be used for accessing saccharides of general formula (I). To accelerate the synthetic process, disaccharidic building blocks such as BB6 and BB7 are preferably used as elongating units.

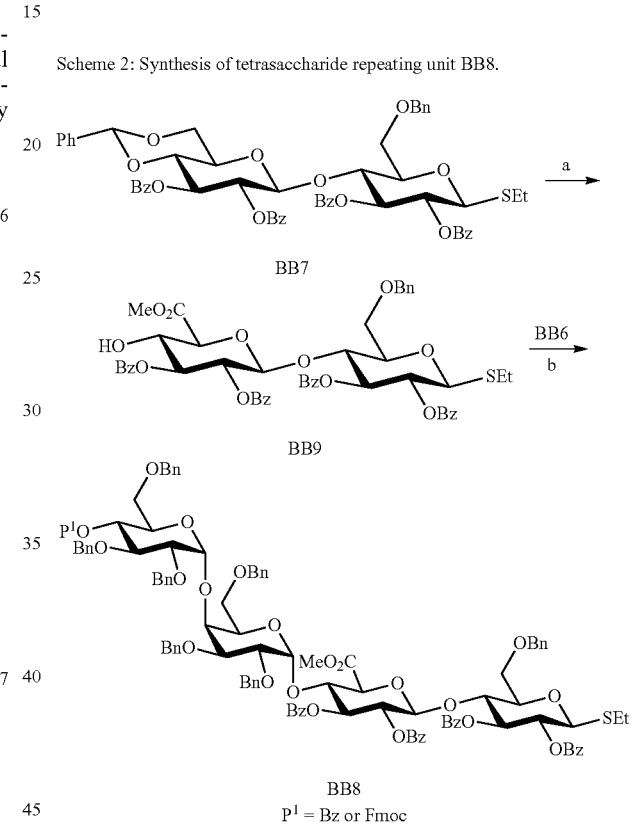

Scheme 2: Synthesis of tetrasaccharide repeating unit BB8.

a. i. EtSH, p-TsOH; ii. BAIB, Tempo; iii. TMS-CHN$_2$; b. BB6, TMSOTf, Et$_2$O/DCM.

The skilled person will appreciate that for accessing higher saccharides of general formula (I), it is convenient to use higher elongating units, such as tetrasaccharide BB8, that can be easily obtained starting from disaccharides BB6 and BB7 according to Scheme 2. Thus, the benzylidene acetal on disaccharide BB7 can be removed by treatment with EtSH, p-TsOH to provide an intermediate diol, which is further submitted to regioselective oxidation with BAIB and Tempo and subsequent esterification of the newly formed carboxylic acid to give secondary alcohol BB9. Alcohol BB9 can be further subjected to glycosylation reaction with disaccharide BB6 to provide tetrasaccharide BB8 that can be directly used as elongating unit. Conveniently, the hydroxyl group at the C-4 position of the α-glucoside moiety can be protected with an orthogonal Fmoc protecting group that enables selective removal in anticipation of further glycosylation reactions. However, if the α-glucoside moiety constitutes the terminal monosaccharide at the non-reducing end, protection of the hydroxyl group at the C-4 position as a benzoate ester will expedite the synthesis.

Microarray

As shown in FIG. 4, the inventive compounds of the formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), (IX-a)-(IX-c) especially saccharides 10, 18, 19, 20, 21, 22, 55, 57, 60 and 62-89 share epitopes with the SP-8 native polysaccharide. The synthetic oligosaccharides were printed on N-hydroxysuccinimide-functionalized glass slides and incubated with either a rabbit antiserum against the native Sp8 bacterium (type 8 antiserum, SSI Diagnostica, FIG. 4 (D)) or combined sera of humans vaccinated with Pneumovax23® ("007sp", National Institute for Biological Standards and Control, FIG. 4 (B), (C)). While the rabbit antiserum revealed recognition of all printed tetrasaccharides (FIG. 4 (D)), the antiserum from human vaccinated with Pneumovax23® recognized only compounds 19, 20, 22 and 18 (see FIGS. 4 (B) and 4 (C)). Robust interactions are observed between saccharides 19 and 18 and the antiserum from human vaccinated with Pneumovax23®. Incubation with SP-8 native polysaccharide abrogated the binding (see FIGS. 4 (B) and 4 (C)). These data demonstrate the specificity and cross reactivity of tetrasaccharides 18, 19 and 20 towards binding to anti-SP8 CPS antibodies.

Microarray analysis enabled also the evaluation of the binding of the mAb 28H11 (a protective murine IgM) to saccharides 19, 20, 21 and 22 (see FIG. 12). MAb 28H11 is a murine IgM that has been raised against native *S. pneumoniae* type 8 CPSs and protects mice from infection with live *S. pneumoniae* type 8 pneumococci in various settings (Yano and Pirofski (2011), *Clin. Vaccine Immunol.*, 18 (1), 59-66). Glycan microarray analysis revealed a robust interaction of mAb 28H11 with saccharide 19 that was specific to *S. pneumoniae* type 8, as shown by the ablation of binding by native *S. pneumoniae* type 8 CPSs of up to 10 μg/mL (see FIG. 12).

Glycoconjugates

Another aspect of the present invention is directed to a conjugate comprising a synthetic saccharide of general formula (I) covalently bound or covalently linked to an immunogenic carrier through the nitrogen atom of the —O-L-NH$_2$ group. In other words, another aspect of the present invention is directed to a saccharide of any of the general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) conjugated with an immunogenic carrier through the nitrogen atom of the —O-L-NH$_2$ group. Thus, a conjugate comprising a synthetic saccharide of the general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) covalently bound or covalently linked to an immunogenic carrier through the nitrogen atom of the OLNH$_2$ group is also defined as a conjugate obtained by reacting a saccharide of any of the general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) with an immunogenic carrier. Said conjugate proved to be efficient as a vaccine for immunization against diseases associated with *Streptococcus pneumoniae* serotype 8 bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, a saccharide of general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) is conjugated to an immunogenic carrier to provide a conjugate presenting increased immunogenicity in comparison with the saccharide.

Said conjugate consists of at least one synthetic saccharide of the general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) and an immunogenic carrier to which the at least one saccharide of the general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) is covalently bound.

Surprisingly, it was found that immunization with a conjugate according to the present invention results in the production of high titers of antibodies specific to the carbohydrate part of the saccharide according to the present invention. Said antibodies are cross-reacting with the natural SP-8 polysaccharides and present opsonophagocytic and bactericidal activity, thus conferring protection against *S. pneumoniae* serotype 8 bacteria. Interactions between monoclonal antibodies elicited by the conjugates of the present invention and *S. pneumoniae* serotype 8 bacteria are specific, since no binding can be observed by antibody isotype controls or towards *S. pneumoniae* serotypes 1 or 3 (see for e.g. FIGS. 8, 9 and 10).

In this context the term "immunogenic carrier" is defined as a structure, which is conjugated to the saccharide to form a conjugate that presents an increased immunogenicity in comparison with the saccharide per se. Thus, the conjugation of a saccharides of the general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) to the immunogenic carrier has as effect the stimulation of the immune response against the saccharide of the general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) without inducing an immune response against the said immunogenic carrier.

Preferred immunogenic carriers are carrier proteins or glycosphingolipids with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, outer membrane protein (OMP), bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include, but are not restricted to N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP), bis-(4-nitrophenyl) adipate and bis-(4-nitrophenyl) succinate (see FIG. 1). Preferred activated esters are disuccinimidyl adipate (DSA), disuccinimidyl glutarate (DSG), bis-(4-nitrophenyl) adipate and bis-(4-nitrophenyl) succinate.

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the inventive saccharides described herein are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker functionalizing the inventive saccharides.

Said functional group X of the interconnecting molecules is selected from the group comprising or consisting of maleimide; α-iodoacetyl; α-bromoacetyl; and N-hydroxysuccinimide ester (NHS), aldehyde, imidoester, carboxylic acid, alkyl sulfonate, sulfonyl chloride, epoxide, anhydride, carbonate (see FIG. 2).

Preferred is a conjugate of general formula (X)

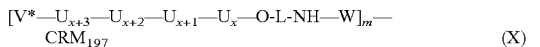

$[V^*—U_{x+3}—U_{x+2}—U_{x+1}—U_x—O-L-NH—W]_m—CRM_{197}$ (X)

wherein m is comprised between 2 and 18;
—W— is selected from:

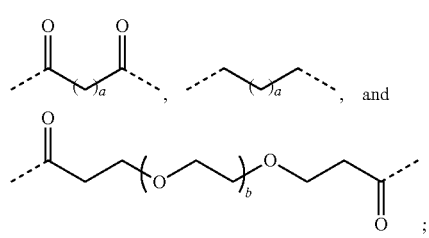

a represents an integer from 1 to 10;
b represents an integer from 1 to 4; and
$V^*$, $U_{x+3}$, $U_{x+2}$, $U_{x+1}$, $U_x$, x and L have the meanings defined herein.

Preferably, the linker -L- is selected from: $-L^a-$, $-L^a-L^e-$, $-L^a-L^b-L^e-$, and $-L^a-L^d-L^e-$;
$-L^a-$ is selected from: $—(CH_2)_o—$, $—(CH_2—CH_2—O)_o—C_2H_4—$, $—(CH_2—CH_2—O)_o—CH_2—$;
$-L^b-$ represents $—O—$;
$-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;
$-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;
and o, q, p1 and p2 are independently of each other an integer selected from 1, 2, 3, 4, 5, and 6.

It is also preferred that —W— represents

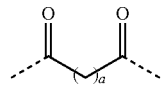

and a is an integer selected from 2, 3, 4, 5 and 6 is especially preferred.

Hence, a conjugate of general formula (X), wherein the linker -L- is selected from: $-L^a-$, $-L^a-L^e-$, $-L^a-L^b-L^e-$, and $-L^a-L^d-L^e-$;
$-L^a-$ is selected from: $—(CH_2)_o—$, $—(CH_2—CH_2—O)_o—C_2H_4—$, $—(CH_2—CH_2—O)_o—CH_2—$;
$-L^b-$ represents $—O—$;
$-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;
$-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;
o, q, p1 and p2 are independently of each other an integer selected from 1, 2, 3, 4, 5, and 6;
—W— represents

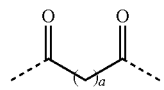

and a is an integer selected from 2, 3, 4, 5 and 6 is especially preferred.

Even more preferred is a conjugate of general formula (X), wherein x represents 3. Thus, a conjugate of general formula (XI)

$[V^*—U_6—U_5—U_4—U_3—O-L-NH—W]_m—CRM_{197}$ (XI)

wherein m is comprised between 2 and 18;
—W— is selected from:

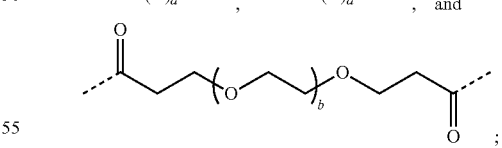

a represents an integer from 1 to 10;
b represents an integer from 1 to 4;

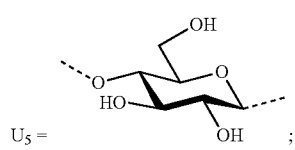

$U_5 =$

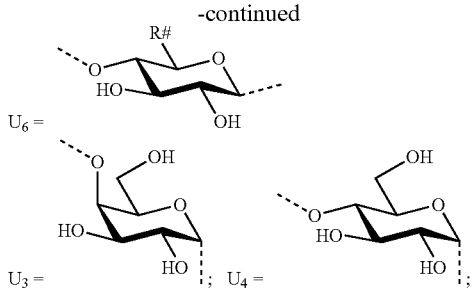

V* represents H—, H—$U_3$— or H—$U_4$—$U_3$—;
R# represents —COOH or —$CH_2OH$; and
L represents a linker is especially preferred.

Preferably, in general formula (XI) the linker -L- is selected from: -$L^a$-, -$L^a$-$L^e$-, -$L^a$-$L^b L^e$-, and -$L^a$-$L^d$-$L^e$-;
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—;
-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;
-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;
o, q, p1 and p2 are independently of each other an integer selected from 1, 2, 3, 4, 5, and 6;
—W— represents

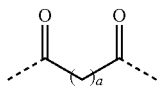

and a is an integer selected from 2, 3, 4, 5 and 6.

Especially preferred is a conugate of general formula (X) or (XI), wherein the linker -L- represents —$(CH_2)_o$—, o is an integer selected from 2, 3, 4, 5 and 6;
—W— represents

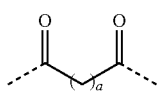

and a is an integer selected from 2, 3, 4, 5 and 6.

Preferably m is comprised between 2 and 18, more preferably between 5 and 15, even more preferably between 8 and 12.

Another aspect of the present invention is directed to a conjugate of general formula (XII)

[S*—$U_5$—$U_4$—$U_3$—S—O-L-NH—W]$_m$CRM$_{197}$ (XII)

wherein
m is comprised between 2 and 18;
—W— is selected from:

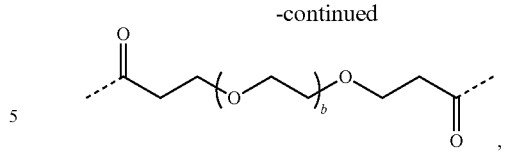

a represents an integer from 1 to 10; and
b represents an integer from 1 to 4;

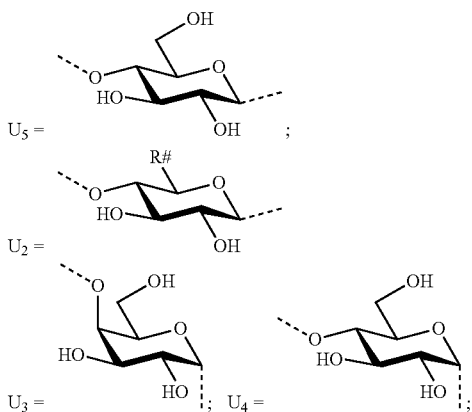

R# represents —COOH or —$CH_2OH$;
—S— represents —$S_a$— or —$S_b$—;
—$S_a$— represents —$(U_5)_{n1}$—, —$(U_5$—$U_4)_{n2}$— or —$(U_5$—$U_4$—$U_3)_{n3}$—;
—$S_b$— represents —$(U_2)_{n1}$—, —$(U_2$—$U_5)_{n2}$— or —$(U_2$—$U_5$—$U_4)_{n3}$—;
S*— represents S*$_a$—, or S*$_b$—;
S*$_a$— represents H—$(U_3)_{n4}$— or H—$(U_4$—$U_3)_{n5}$—;
S*$_b$— represents H—$(U_2)_{n4}$—, H—$(U_3$—$U_2)_{n5}$— or H—$(U_4$—$U_3$—$U_2)_{n6}$—;
n1, n2, n3, n4, n5 and n6 are selected from 0 and 1;
L is a linker;
with the proviso that
if —S— represents —$S_a$—, then S*— represents S*$_a$—; and
if —S— represents —$S_b$—, then S*— represents S*$_b$—; and
if n1=1, then n6=0; and
if n2=1, then n5=n6=0; and
if n3=1, then n4=n5=n6=0; and
if n4=1, then n3=0; and
if n5=1, then n2=n3=0; and
if n6=1, then n1=n2=n3=0.

A further preferred conjugate is a conjugate of general formula (XIII)

[S$_b$*—$U_5$—$U_4$—$U_3$—S$_b$—O-L-NH—W]$_m$CRM$_{197}$ (XIII)

wherein
m is comprised between 2 and 18;
—W— is selected from:

-continued

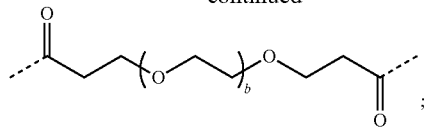

a represents an integer from 1 to 10; and
b represents an integer from 1 to 4;

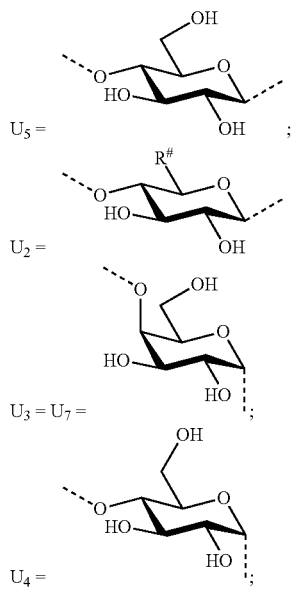

$R^{\#}$ represents —COOH or —CH$_2$OH;
—S$_b$— represents —(U$_2$)$_{n1}$—, —(U$_2$—U$_5$)$_{n2}$— or —(U$_2$—U$_5$—U$_4$)$_{n3}$—;
S*$_b$— represents H—(U$_2$)$_{n4}$—, H—(U$_3$—U$_2$)$_{n5}$— or H—(U$_4$—U$_3$—U$_2$)$_{n6}$—;
n1, n2, n3, n4, n5 and n6 are selected from 0 and 1;
L is a linker;
with the proviso that
if n1=1, then n6=0; and
if n2=1, then n5=n6=0; and
if n3=1, then n4=n5=n6=0; and
if n4=1, then n3=0; and
if n5=1, then n2=n3=0; and
if n6=1, then n1=n2=n3=0.

Preferably, the linker L is selected from: -L$^a$-, -L$^a$-L$^e$-, -L$^a$-L$^b$-L$^e$-, and -L$^a$-L$^d$-L$^e$-;
-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^b$- represents —O—;
-L$^d$- is selected from: —(CH$_2$)$_q$—, —(CF$_2$)$_q$—, —(CH$_2$—CH$_2$—O)$_q$C$_2$H$_4$—, and —(CH$_2$—CH$_2$—O)$_q$—CH$_2$—;
-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
and o, q, p1 and p2 are independently of each other an integer selected from 1, 2, 3, 4, 5, and 6.

It is also preferred that —W— represents

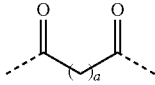

and a is an integer selected from 2, 3, 4, 5 and 6 is especially preferred.

Hence, a conjugate of general formula (XII) or (XIII), wherein the linker -L- is selected from: -L$^a$-, -L$^a$-L$^e$-, -L$^a$-L$^b$-L$^e$-, and -L$^a$-L$^d$-L$^e$-;
-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^b$- represents —O—;
-L$^d$- is selected from: —(CH$_2$)$_q$—, —(CF$_2$)$_q$—, —(CH$_2$—CH$_2$—O)$_q$—C$_2$H$_4$—, and —(CH$_2$—CH$_2$—O)$_q$—CH$_2$—;
-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— and —(CH$_2$)$_{p1}$—O—(CH$_2$)$_{p2}$—;
o, q, p1 and p2 are independently of each other an integer selected from 1, 2, 3, 4, 5, and 6;
—W— represents

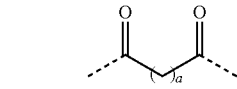

and a is an integer selected from 2, 3, 4, 5 and 6 is especially preferred.

Especially preferred is a conjugate of general formula (XII) or (XIII), wherein the linker -L- represents —(CH$_2$)$_o$—,
o is an integer selected from 2, 3, 4, 5 and 6;
—W— represents

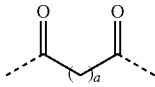

and a is an integer selected from 2, 3, 4, 5 and 6.

Still more preferred is a conjugate of the general formula (X-a)

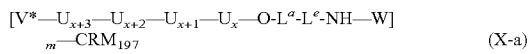

(X-a)

wherein
-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^e$- is selected from: —C$_2$H$_4$—(O—CH$_2$—CH$_2$)$_{p1}$—, —CH$_2$—(O—CH$_2$—CH$_2$)$_{p1}$—, —(CH$_2$)$_{p1}$—, and —(CH$_2$)$_{p1}$—O—(CH$_2$)$_{p2}$—;
V*, x, m, o, p1, p2, U$_x$, U$_{x+1}$, U$_{x+2}$, U$_{x+3}$ and CRM$_{197}$ have the meanings as defined herein.

Also more preferred is a conjugate of the general formula (XI-a)

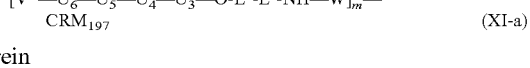

(XI-a)

wherein
-L$^a$- is selected from: —(CH$_2$)$_o$—, —(CH$_2$—CH$_2$—O)$_o$—C$_2$H$_4$—, —(CH$_2$—CH$_2$—O)$_o$—CH$_2$—;
-L$^e$- is selected from: —C$_2$H$_4$—(O—CH$_2$—CH$_2$)$_{p1}$—, —CH$_2$—(O—CH$_2$—CH$_2$)$_{p1}$—, —(CH$_2$)$_{p1}$—, and —(CH$_2$)$_{p1}$—O—(CH$_2$)$_{p2}$—;

$V^*$, x, m, o, p1, p2, $U_6$, $U_5$, $U_4$, $U_3$ and $CRM_{197}$ have the meanings as defined herein.

Also more preferred is a conjugate of the general formula (XII-a)

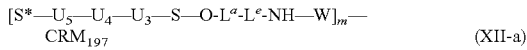
$$[S^*\text{—}U_5\text{—}U_4\text{—}U_3\text{—}S\text{—}O\text{-}L^a\text{-}L^e\text{-}NH\text{—}W]_m\text{—}CRM_{197} \quad (XII\text{-a})$$

wherein
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^e$- is selected from: —$C_2H_4$—$(O$—$CH_2$—$CH_2)_{p1}$—, —$CH_2$—$(O$—$CH_2$—$CH_2)_{p1}$—, —$(CH_2)_{p1}$—, and —$(CH_2)_{p1}$—$O$—$(CH_2)_{p2}$—;
$S^*$, S, m, o, p1, p2, $U_5$, $U_4$, $U_3$ and $CRM_{197}$ have the meanings as defined herein.

Also more preferred is a conjugate of the general formula (XIII-a)

$$[S_b^*\text{—}U_5\text{—}U_4\text{—}U_3\text{—}S_b\text{-}O\text{-}L^a\text{-}L^e\text{-}NH\text{—}W]_m\text{—}CRM_{197} \quad (XIII\text{-a})$$

wherein
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^e$- is selected from: —$C_2H_4$—$(O$—$CH_2$—$CH_2)_{p1}$—, —$CH_2$—$(O$—$CH_2$—$CH_2)_{p1}$——$(CH_2)_{p1}$—, and —$(CH_2)_{p1}$—$O$—$(CH_2)_{p2}$—;
$S_b^*$, $S_b$, m, o, p1, p2, $U_5$, $U_4$, $U_3$ and $CRM_{197}$ have the meanings as defined herein.

Still more preferred is a conjugate of the general formula (X-b)

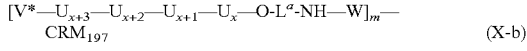
$$[V^*\text{—}U_{x+3}\text{—}U_{x+2}\text{—}U_{x+1}\text{—}U_x\text{—}O\text{-}L^a\text{-}NH\text{—}W]_m\text{—}CRM_{197} \quad (X\text{-b})$$

wherein
-$L^a$- represents: —$(CH_2)_{o1}$—, —$(CH_2$—$CH_2$—$O)_{o2}$—$C_2H_4$—, —$(CH_2$—$CH_2$—$O)_{o2}$—$CH_2$—;
o1 is an integer selected from 2, 3, 4, 5 and 6;
o2 is an integer selected from 1, 2, 3, 4, 5 and 6;
$V^*$, x, m, $U_x$, $U_{x+1}$, $U_{x+2}$, $U_{x+3}$ and $CRM_{197}$ have the meanings as defined herein.

Also more preferred is a conjugate of the general formula (XI-b)

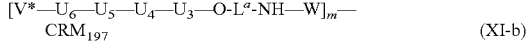
$$[V^*\text{—}U_6\text{—}U_5\text{—}U_4\text{—}U_3\text{—}O\text{-}L^a\text{-}NH\text{—}W]_m\text{—}CRM_{197} \quad (XI\text{-b})$$

wherein
-$L^a$- represents: —$(CH_2)_{o1}$—, —$(CH_2$—$CH_2$—$O)_{o2}$—$C_2H_4$—, —$(CH_2$—$CH_2$—$O)_{o2}$—$CH_2$—;
o1 is an integer selected from 2, 3, 4, 5 and 6;
o2 is an integer selected from 1, 2, 3, 4, 5 and 6;
$V^*$, x, m, $U_6$, $U_5$, $U_4$, $U_3$ and $CRM_{197}$ have the meanings as defined herein.

Also more preferred is a conjugate of the general formula (XII-b)

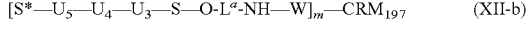
$$[S^*\text{—}U_5\text{—}U_4\text{—}U_3\text{—}S\text{—}O\text{-}L^a\text{-}NH\text{—}W]_m\text{—}CRM_{197} \quad (XII\text{-b})$$

wherein
-$L^a$- represents: —$(CH_2)_{o1}$—, —$(CH_2$—$CH_2$—$O)_{o2}$—$C_2H_4$—, —$(CH_2$—$CH_2$—$O)_{o2}$—$CH_2$—;
o1 is an integer selected from 2, 3, 4, 5 and 6;
o2 is an integer selected from 1, 2, 3, 4, 5 and 6;
$S^*$, S, m, $U_5$, $U_4$, $U_3$ and $CRM_{197}$ have the meanings as defined herein.

Also more preferred is a conjugate of the general formula (XIII-b)

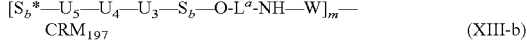
$$[S_b^*\text{—}U_5\text{—}U_4\text{—}U_3\text{—}S_b\text{—}O\text{-}L^a\text{-}NH\text{—}W]_m\text{—}CRM_{197} \quad (XIII\text{-b})$$

wherein
-$L^a$- represents: —$(CH_2)_{o1}$—, —$(CH_2$—$CH_2$—$O)_{o2}$—$C_2H_4$—, —$(CH_2$—$CH_2$—$O)_{o2}$—$CH_2$—;
o1 is an integer selected from 2, 3, 4, 5 and 6;
o2 is an integer selected from 1, 2, 3, 4, 5 and 6;
$S_b^*$, $S_b$, m, $U_5$, $U_4$, $U_3$ and $CRM_{197}$ have the meanings as defined herein.

Still more preferred is a conjugate of the general formula (X-c)

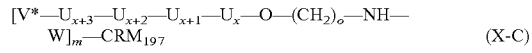
$$[V^*\text{—}U_{x+3}\text{—}U_{x+2}\text{—}U_{x+1}\text{—}U_x\text{—}O\text{—}(CH_2)_o\text{—}NH\text{—}W]_m\text{—}CRM_{197} \quad (X\text{-C})$$

wherein
o is an integer selected from 2, 3, 4, 5 and 6;
$V^*$, x, m, $U_x$, $U_{x+1}$, $U_{x+2}$, $U_{x+3}$ and $CRM_{197}$ have the meanings as defined herein.

Also more preferred is a conjugate of the general formula (XI-c)

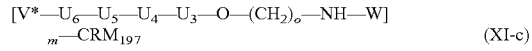
$$[V^*\text{—}U_6\text{—}U_5\text{—}U_4\text{—}U_3\text{—}O\text{—}(CH_2)_o\text{—}NH\text{—}W]_m\text{—}CRM_{197} \quad (XI\text{-c})$$

wherein
o is an integer selected from 2, 3, 4, 5 and 6;
$V^*$, x, m, $U_6$, $U_5$, $U_4$, $U_3$ and $CRM_{197}$ have the meanings as defined herein.

Also more preferred is a conjugate of the general formula (XII-c)

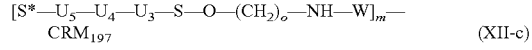
$$[S^*\text{—}U_5\text{—}U_4\text{—}U_3\text{—}S\text{—}O\text{—}(CH_2)_o\text{—}NH\text{—}W]_m\text{—}CRM_{197} \quad (XII\text{-c})$$

wherein
o is an integer selected from 2, 3, 4, 5 and 6;
$S^*$, S, m, $U_5$, $U_4$, $U_3$ and $CRM_{197}$ have the meanings as defined herein.

Also more preferred is a conjugate of the general formula (XIII-c)

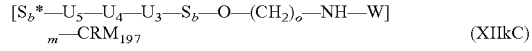
$$[S_b^*\text{—}U_5\text{—}U_4\text{—}U_3\text{—}S_b\text{—}O\text{—}(CH_2)_o\text{—}NH\text{—}W]_m\text{—}CRM_{197} \quad (XIIkC)$$

wherein
o is an integer selected from 2, 3, 4, 5 and 6;
$S_b^*$, $S_b$, m, $U_5$, $U_4$, $U_3$ and $CRM_{197}$ have the meanings as defined herein.

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glyco-sphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci.* USA, 1998, 95, 5690).

The conjugates of the inventive saccharides with a glycosphingolipid with immunomodulatory properties have the advantage of being heat stable. To be suitable for conjugation, on the glycosphingolipid with immunomodulatory properties a functionality is introduced. Said functionality is prone to react directly with the terminal amino group of the linker of the inventive to provide conjugates of the saccharides or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride. A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C-6 position of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected of the group comprising or consisting of maleimide, α-iodoacetyl, α-bromoacetyl, N-hydroxysuccinimide ester (NHS), aldehyde, carboxylic acid, epoxyde, alkyl sulfonate, sulfonyl chloride, anhydride, carbonate.

Preferably, di(N-succinimidyl) adipate or bis(4-nitrophenyl) adipate is first reacted with a synthetic saccharide having a primary amino group. Activated saccharide is subsequently condensed with a glycosphingolipid, which is modified at C-6 position by an interconnecting molecule having a terminal amino functionality in order to afford the conjugate (FIG. 3 (B)).

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

It was found that the saccharide of general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) covalently linked or covalently bound to an immunogenic carrier through the nitrogen atom of the —O-L-NH$_2$ group or in other words the conjugate obtained by reacting a saccharide of general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), or (IX-a)-(IX-c) with an immunogenic carrier, and especially a conjugate of general formula (X), (X-a)-(X-c), (XI), (XI-a)-(XI-c), (XII), (XII-a)-(XII-c), (XIII), or (XIII-a)-(XIII-c) elicits an immune response in a human and/or animal host, and therefore is useful in the prevention and/or treatment of a disease associated with bacteria containing in their capsular polysaccharide one of the following saccharide fragments:

α-D-Glcp-(1→4)-α-D-Galp-(1→4)-β-D-GlcAp-(1→4)-β-D-Glcp,

β-D-Glcp-(1→4)-α-D-Glcp-(1→4)-α-D-Galp-(1→4)-β-D-GlcAp,

β-D-GlcAp-(1→4)-β-D-Glcp-(1→4)-α-D-Glcp-(1→4)-α-D-Galp,

α-D-Galp-(1→4)-β-D-GlcAp-(1→4)-β-D-Glcp-(1→4)-α-D-Glcp.

Preferably, the bacterium containing in the capsular polysaccharide one of the above mentioned saccharide fragments is *Streptococcus pneumoniae* serotype 8. Diseases associated with *Streptococcus pneumoniae* serotype 8 include pneumonia, meningitis, otitis media, bacteremia and acute exacerbation of chronic bronchitis, sinusitis, arthritis and conjunctivitis.

Pharmaceutical Composition

One aspect of the present invention relates to a pharmaceutical composition, especially a vaccine containing at least one synthetic saccharide according to the present invention and/or a pharmaceutical acceptable salt thereof and/or a conjugate comprising a saccharide according to the present invention covalently linked to an immunogenic carrier through the nitrogen atom of the —O-L-NH$_2$ group together with at least one pharmaceutical acceptable adjuvant, cryoprotectant, lyoprotectant, excipient and/or diluent.

In another aspect of the present invention, said pharmaceutical composition or vaccine further comprises at least one of capsular polysaccharides and/or capsular polysaccharide fragments and/or protein conjugates thereof of *Streptococcus pneumoniae* bacteria selected from the group comprising or consisting of *Streptococcus pneumoniae* serotypes 4, 6B, 9V, 14, 18C, 19F and 23F, preferably serotypes 1, 3, 4, 5, 6A, 6B, 7F, 9V, 14, 18C, 19F and 23F, and more preferably serotypes 1, 2, 3, 4, 5, 6A, 6B, 7F, 8, 9N, 9V, 10A, 11A, 14, 15B, 17F, 18C, 19F, 19A, 20, 22F, 23F and 33F.

The vaccine may be prepared in the form of a suspension or may be lyophilized. The suspension form may be stored frozen. In the lyophilized form, it is preferable to add one or more stabilizers. Vaccination can be performed at any age. The vaccine many be administered subcutaneously, by spray, by injection, orally, intraocularly, intratracheally or nasally. The amount of vaccine of the invention to be administered a human or animal and the regime of administration can be determined in accordance with standard techniques well known to those of ordinary skill in the pharmaceutical and veterinary arts taking into consideration such factors as the particular antigen, the adjuvant (if present), the age, sex, weight, species and condition of the particular animal or human host, and the route of administration.

Another aspect of the present invention is directed to a method of inducing immune response against *Streptococcus pneumoniae* in a human and/or animal host, said method comprising administering of the saccharide according to the present invention and/or salt thereof and/or a a conjugate comprising a saccharide according to the present invention covalently linked to an immunogenic carrier through the nitrogen atom of the —O-L-NH$_2$ group and/or a mixture thereof or pharmaceutical composition thereof to said human and/or animal host. A method of treating or preventing diseases caused by *Streptococcus pneumoniae* in a human and/or animal host according to the present invention comprises administering of at least one saccharide according to the present invention and/or salt thereof and/or a conjugate comprising a saccharide according to the present invention covalently linked to an immunogenic carrier through the nitrogen atom of the —O-L-NH$_2$ group and/or a mixture thereof or pharmaceutical composition thereof to said human and/or animal host.

Intravenous and parenteral administration is preferred. Such compositions may be in admixture with a suitable carrier, diluent, or excipient such as sterile water, physiological saline, glucose or the like. For instance, lyophilized saccharides of the invention can ultimately be reconstituted with a liquid component to give material suitable for administration to a said human and/or animal host. The reconstitution will typically take place at the point of use. Thus, a saccharide of the invention and an oil-in-water emulsion adjuvant or a buffer solution of an adjuvant may be kept separately in a packaged or distributed vaccine kit, ready for final formulation at the time of use. In a kit containing two containers, one will include liquid for reconstitution and the second container includes lyophilized material. For stability reasons, the lyophilized component of the invention may include a stabilizer such as lactose, sucrose and/or mannitol, as well as mixtures thereof. Using a sucrose/mannitol mixture can speed up the drying process. A lyophilized component may also include sodium chloride. Soluble components in the lyophilized material will be retained in the composition after reconstitution, and so final liquid vaccines may thus contain lactose and/or sucrose.

Formulation of the vaccines of the present invention can be accomplished using methods known by the art. Obviously, the choice of suitable carriers and other additives will depend on the exact route of administration and the nature of the particular dosage form.

The vaccine compositions of the present invention may contain one or more adjuvants. The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant), saponins, aluminium or calcium salts (e.g. alum), non-ionic block polymer surfactants, α-galactosylceramide and many others.

The vaccines of the present invention can contain auxiliary substances such as wetting or emulsifying agents, pH buffering agents, gelling or viscosity enhancing additives, preservatives, flavoring agents, colors, and the like, depending upon the route of administration and the preparation desired. Compositions of the invention may include an antimicrobial, particularly when packaged in multiple dose formats. Antimicrobials such as thiomersal and 2-phenoxyethanol are commonly found in vaccines, but it is preferred to use either a mercury-free preservative or no preservative at all.

Further, the inventive vaccines may include a temperature protective agent. Examples include glycerin, propylene glycol, and/or polyethylene glycol (PEG).

The pharmaceutical compositions of the present invention are conveniently provided as liquid preparations, e.g., isotonic aqueous solutions, suspensions, emulsions or viscous compositions that may be buffered to a selected pH. Pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic solutions, emulsions or suspensions, including saline and buffered media.

The pH of a composition after reconstitution is preferably between 6 and 8 and more preferably between 6.5 and 7.5 (e.g. about 7). Compositions of the invention may be maintained by the use of a buffer e.g. a Tris buffer, acetate, glutamate, lactate, maleate, tartrate, phosphate, citrate, carbonate, glycinate, histidine, glycine, succinate and triethanolamine buffer. Thus, compositions of the invention will preferably include a buffer. The isotonic agent may be an ionic isotonic agent such as a salt or a non-ionic isotonic agent such as a carbohydrate. Examples of ionic isotonic agents include, but are not limited to NaCl, CaCl$_2$, KCl and MgCl$_2$. Examples of non-ionic isotonic agents include but are not limited to sorbitol and glycerol.

In a preferred embodiment of the invention, the vaccine composition is formulated as a sterile liquid, pyrogene-free, phosphate-buffered physiological saline, with or without a preservative.

A pharmaceutically acceptable preservative can be employed to increase the shelf life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

The pharmaceutical compositions of the invention can be formulated as single dose vials, multidose vials or as pre-filled syringes.

Further preferred, the pharmaceutical composition is formulated in the form of a lyophilisate or liquid buffer solution.

The vaccine or pharmaceutical composition of the present invention is prepared in a conventional solid or liquid carrier or diluents and a conventional pharmaceutically-made adjuvant at suitable dosage level in a known way. The preferred preparations and formulations are in administrable, form which is suitable for oral application. These administrable forms, for example, include pills, tablets, film tablets, coated tablets, capsules, powders and deposits. Forms other than oral administrable forms are also possible. The inventive vaccine or pharmaceutical composition may be administered by any appropriate means, including but not limited to inhalation, injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrically, intracutaneously, intravaginally, intravasally, intranasally, intrabuccally, percutaneously, sublingually, or any other means available within the pharmaceutical arts.

The vaccine or pharmaceutical composition of the present invention, containing at least one synthetic saccharide of any of general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c), preferably the saccharides 10, 18, 19, 20, 21, 22, 55, 57, 60 and 62 or pharmaceutically acceptable salt thereof, or a a conjugate comprising a saccharide of general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) covalently linked to an immunogenic carrier through the nitrogen atom of the —O-L-NH$_2$ group as an active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active ingredient may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent of the saccharide according to the present invention.

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavouring agents and preservatives may also be included where appropriate. Some of the terms noted above, namely disintegrants, diluents, lubricants, binders and the like, are discussed in more detail below.

Additionally, the vaccine or pharmaceutical composition of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidifies.

Also included are solid form preparations, which are intended to be converted, shortly before use, to liquid form preparations for either oral or parenteral administration. Such liquid forms include solutions, suspensions and emulsions.

The inventive vaccine or pharmaceutical composition containing at least one synthetic saccharide of any of general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c), preferably the saccharides 10, 18, 19, 20, 21, 22, 55, 57, 60 and 62-89 or pharmaceutically acceptable salt thereof, or a conjugate comprising a saccharide covalently linked or covalently bound to an immunogenic carrier through the nitrogen atom of the —O-L-NH$_2$ group may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or moulded solid dosage form containing the active ingredients with suitable diluents. The tablet can be prepared by compression of mixtures or granulations obtained by wet granulation, dry granulation or by compaction well known to a person skilled in the art.

Oral gels refer to the active ingredients dispersed or solubilized in a hydrophilic semi-solid matrix.

Powders for constitution refer to powder blends containing the active ingredients and suitable diluents which can be suspended in water or juices.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives, such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'I-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Colouring agents are excipients that provide coloration to the composition or the dosage form. Such excipients can include food grade dyes and food grade dyes adsorbed onto a suitable adsorbent such as clay or aluminium oxide. The amount of the colouring agent can vary from about 0.01 to 10% by weight of the composition, preferably from about 0.05 to 6% by weight, more preferably from about 0.1 to about 4% by weight of the composition, and most preferably from about 0.1 to about 1%.

Techniques for the formulation and administration of the vaccine of the present invention may be found in "Remington's Pharmaceutical Sciences" Mack Publishing Co., Easton Pa. A suitable vaccine composition comprising at least one saccharide of any one of the general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c), preferably the saccharides 10, 18, 19, 20, 21, 22, 55, 57, 60 and 62-89 or pharmaceutically acceptable salt thereof, or a conjugate comprising a saccharide covalently linked to an immunogenic carrier through the nitrogen atom of the —O-L-NH$_2$ group, may be a solution of such saccharide(s) in a suitable liquid pharmaceutical carrier or any other formulation such as tablets, pills, film tablets, coated tablets, dragees, capsules, powders and deposits, gels, syrups, slurries, suspensions, emulsions, and the like.

A therapeutically effective dosage of one conjugate according to the present invention or of one saccharide according to the present invention refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index.

The actual amount of the composition administered will be dependent on the subject being treated, on the subject's weight, the severity of the affliction, the manner of administration and the judgement of the prescribing physician.

Antibody and Immunological Assays

The present invention refers also to an antibody against at least one synthetic saccharide according to the present invention. The antibody is produced by the monoclonal hybridoma. The antibody is useful for diagnostics, prophylaxis, and treatment of pneumonia, meningitis, otitis media, bacteremia and acute exacerbation of chronic bronchitis, sinusitis, arthritis and conjunctivitis. Another embodiment of the present invention concerns the use of the antibody for manufacture of medicaments or devices for diagnosis, prophylaxis, and treatment of pneumonia, meningitis, otitis media, bacteremia and acute exacerbation of chronic bronchitis, sinusitis, arthritis and conjunctivitis caused by *S. pneumoniae*, and preferably by *S. pneumoniae* serotype 8.

The term "antibody" as used herein encompasses polyclonal and monoclonal antibody preparations, as well as preparations including hybrid antibodies, F(ab')$_2$ fragments, F(ab) molecules, single domain antibodies and functional fragments thereof, which exhibit immunological binding properties of the parent antibody molecule.

The antibody according to the invention may be polyclonal or monoclonal.

The saccharide of any one of general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c), preferably the saccharides 10, 18, 19, 20, 21, 22, 55, 57, 60 or 62-89 or a conjugate comprising one of the above-mentioned saccharides covalently linked to an immunogenic carrier through the nitrogen atom of the —O-L-NH$_2$ group or the antibody thereof can be used for preparing a pharmaceutical composition, especially a vaccine, for the treatment or prevention of diseases caused by *S. pneumoniae*, preferably *S. pneumoniae* serotype 8. The saccharide of the present invention or the antibody raised against and recognizing the saccharide according to the present invention can be used for the treatment or prevention of a disease caused by *S. pneumoniae*, preferably *S. pneumoniae* serotype 8.

Further the present invention refers to at least one saccharide of general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) according to the invention or at least one antibody against at least one saccharide of the present invention for use in immunological assays for diagnosis of pneumonia, meningitis, otitis media, bacteremia and acute exacerbation of chronic bronchitis, sinusitis, arthritis and conjunctivitis caused by *S. pneumoniae*, preferably *S. pneumoniae* serotype 8.

Such assays comprise, for instance, microarray and ELISA useful for diagnosis of diseases caused by *S. pneumoniae*, preferably *S. pneumoniae* serotype 8. Therefore, another aspect of the present invention refers to the use of any one of saccharides of formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) for diagnosis of diseases caused by *S. pneumoniae*, preferably *S. pneumoniae* serotype 8.

Any one of saccharides of general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) or a mixture of such saccharides could be immobilized on a microarray surface or any other surface and used for an in vitro method of detecting S. pneumoniae serotype 8. A method of identifying S. pneumoniae serotype 8 comprises the use of at least one saccharide of the present invention. Furthermore, the synthetic saccharide of general formulae (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) or a mixture of such saccharides can be used as an analytical standard for immunoassays.

Thus, the saccharide of general formula (I), (I-a)-(I-c), (II), (II-a)-(II-g), (III), (III-a)-(III-g), (IV), (IV-a)-(IV-g), (V), (V-a)-(V-c), (VI), (VI-a)-(VI-c), (VII), (VII-a)-(VII-c), (VIII), (VIII-a)-(VIII-c), (IX), and (IX-a)-(IX-c) can be used as a marker in immunological assays for detection of antibodies against Streptococcus pneumoniae type 8.

Thus, another aspect of the present invention is related to a solid support comprising at least one saccharide according to the present invention This solid support is preferable a part of a diagnostic device. The solid support and the diagnostic device are used for diagnosis of pneumonia, meningitis, otitis media, bacteremia and acute exacerbation of chronic bronchitis, sinusitis, arthritis and conjunctivitis caused by S. pneumoniae, preferably S. pneumoniae serotype 8, wherein the at least one saccharide according to the present invention is immobilized on said solid support by preferably covalent bonding.

Preferably, the solid support is selected from the group comprising a glass slide, glass plate, a microtitre plate, microspheres, or beads.

The inventive saccharide is preferably covalently bound to the solid support using an interconnecting molecule.

Moreover, the present invention shows that the inventive saccharide can be used in immunological assays detection of for pneumonia, meningitis, otitis media, bacteremia and acute exacerbation of chronic bronchitis, sinusitis, arthritis and conjunctivitis caused by S. pneumoniae, preferably S. pneumoniae serotype 8. Such assays comprise, for instance, microarray and ELISA useful for diagnosis of pneumonia, meningitis, otitis media, bacteremia and acute exacerbation of chronic bronchitis, sinusitis, arthritis and conjunctivitis caused by S. pneumoniae, preferably S. pneumoniae serotype 8.

Therefore another aspect of the present invention refers to the use of a saccharide according to the present invention for diagnosis of pneumonia, meningitis, otitis media, bacteremia and acute exacerbation of chronic bronchitis, sinusitis, arthritis and conjunctivitis caused by S. pneumoniae, preferably S. pneumoniae serotype 8.

There are different possibilities for the choice of an assay system in which a saccharide according to the present invention is used for diagnosis of pneumonia, meningitis, otitis media, bacteremia and acute exacerbation of chronic bronchitis, sinusitis, arthritis and conjunctivitis caused by S. pneumoniae, preferably S. pneumoniae serotype 8. An assay conducted for diagnostic purposes according to the invention may be an immune assay like a solid-phase enzyme immunoassay (EIA), an enzyme linked immunosorbent assay (ELISA), especially an "indirect" ELISA or a radioimmune assay (RIA).

Preferably, the saccharide according to the present invention is covalently linked on the solid support through an interconnecting molecule. Thus, the saccharide according to the present invention can be covalently linked on the solid support directly or indirectly through the nitrogen atom of the —O-L-NH$_2$ group (see FIG. 3 (C)).

The solid support is preferably selected from the group comprising or consisting of: a glass slide, a microtitre plate, test tubes, microspheres, nanoparticle or beads.

It is particularly preferred that the solid support is a glass slide or a microtitre plate. A microtitre plate or microplate or microwell plate is a flat plate with multiple "wells" used as small test tubes. Typically, a microtitre plate having 6, 24, 96, 384 or even 1536 sample wells can be used. Microplates are produced from many different materials, like polycarbonate for microtitre plate used for PCR. The most common is polystyrene as used for most optical detection microplates. It can be colored white by the addition of titanium dioxide for optical absorbance or luminescence detection or black by the addition of carbon for fluorescent biological assays.

(B) Inhibition of binding with mAb 1 H8 and 1F1 (100 μg/mL) pre-adsorbed with SP8 CPS (10 μg/mL concentration). Non-parametric, one-tailed t test with Welch's correction: P<0.01; *P<0.001: binding of mAbs 1H8 and 1F1 to pentasaccharide 55 and hexasaccharide 57 was abrogated by inhibition with native SP8 polysaccharide;

(C) structure compound 90.

Figure 12:
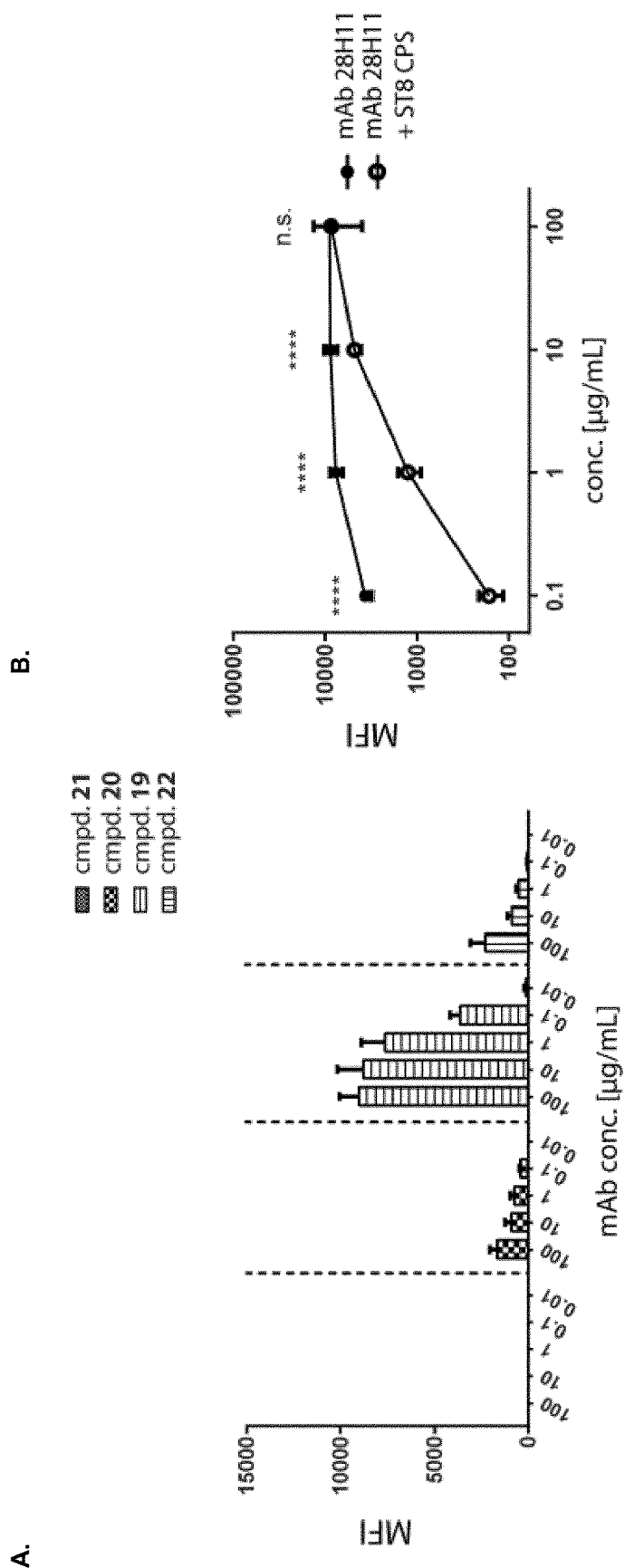

FIG. 12: Microarray analysis of the binding of the mAb 28H11 (protective murine IgM) to saccharides 19, 20, 21 and 22. (A) Binding at different concentrations of mAb 28H11. (B) Inhibition of the binding of mAb 28H11 to compound 19 by addition of native *S. pneumoniae* type 8 CPS (10 μg/mL).

Figure 13:
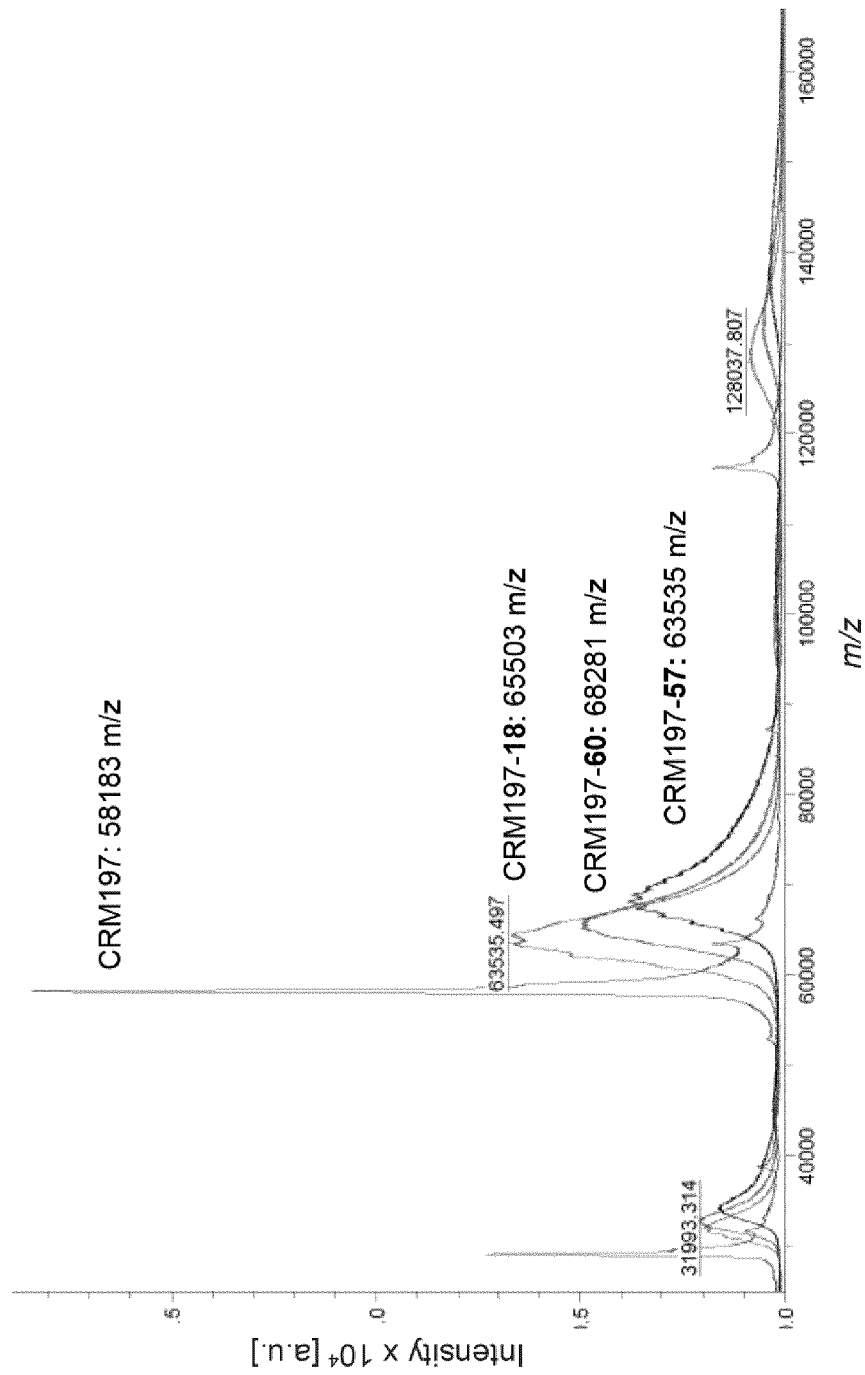

FIG. 13: Characterization by MALDI-MS of the conjugates $CRM_{197}$-18, $CRM_{197}$-60 and $CRM_{197}$-57.

Figure 14:
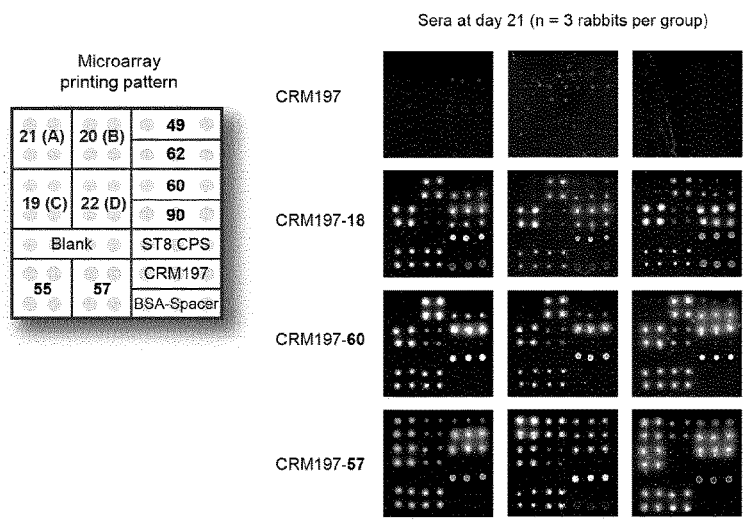
Figure 14:
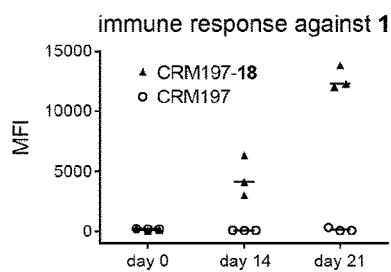
Figure 14:
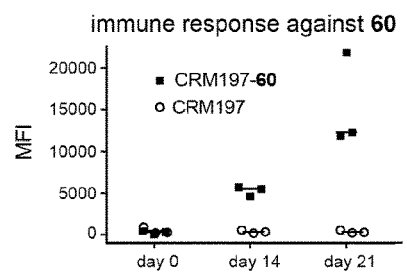
Figure 14:
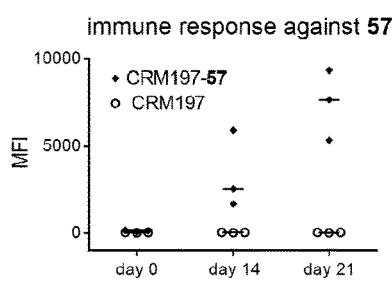
Figure 14:
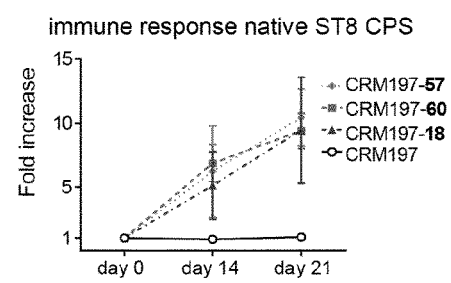
Figure 14:
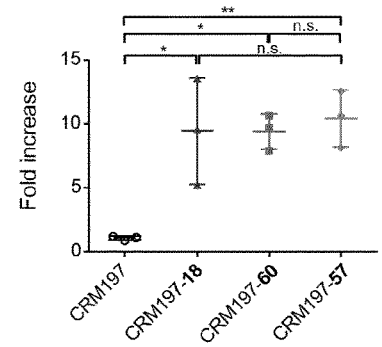
Figure 14:
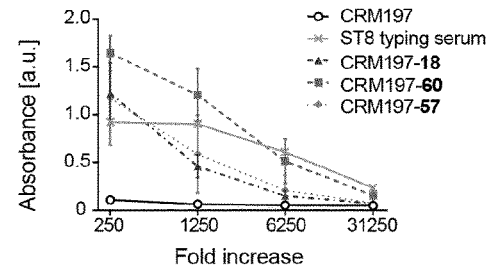

FIG. 14: Evaluation of the immune response against the conjugates $CRM_{197}$-18, $CRM_{197}$-60, and $CRM_{197}$-57. in rabbits. (A)-(D), glycan microarray analysis of the immune response against *S. pneumoniae* type 8-related glycans (1:50 dilution).

(A) glycan microarray analysis of sera at day 21. All rabbits immunized with conjugates show a marked immune response against S. pneumoniae type 8 CPS-related oligosaccharides and ST8 CPS.

(B) time course of the immune response against tetrasaccharide 19 of rabbits immunized with $CRM_{197}$-18 or $CRM_{197}$ alone.

(C) time course of the immune response against tetrasaccharide 60 of rabbits immunized with $CRM_{197}$-60 or $CRM_{197}$ alone.

(D) time course of the immune response against hexasaccharide 57 of rabbits immunized with $CRM_{197}$-57 or $CRM_{197}$ alone.

(E) time course of the immune response against *S. pneumoniae* CPS of immunized rabbits, as assessed by polysaccharide ELISA (1:50 dilution). Values depict fold increase compared to the values of pre-immune sera.

(F) comparison of the immune response against *S. pneumoniae* type 8 CPS at day 21, as assessed by polysaccharide ELISA. Statistical analysis was performed (one-way ANOVA, Bonferroni correction) and Asterisks depict P values: n.s. not significant; * P <0.05; ** P <0.005. G, comparison of the immune response against *S. pneumoniae* type 8 CPS at day 21 at different dilutions, as assessed by polysaccharide ELISA. Rabbit-derived *S. pneumoniae* type 8 typing serum was used as a reference.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

1. Chemical Synthetic Experiments

General Information for Chemical Synthesis.

All commercially available starting materials and reagents were used as received unless otherwise noted. All the reactions were performed under argon atmosphere. Solvents were dried. High-resolution mass spectra (HRMS) were recorded with an Agilent 6210 ESI-TOF mass spectrometer at the Freie Universitat Berlin.

Abbreviations

In the following schemes occurring abbreviations mean Ac (acetyl), BAIB ([bis(acetoxy)iodo]benzene), Bn (benzyl), t-Bu (tert-butyl), Bz (benzoyl), Cbz (carboxybenzyl), DCM (dichloromethane), DDQ (2,3-dichloro-5,6-dicyano-1,4-benzoquinone), Im (imidazole), NAP (2-naphthylmethyl), NIS (N-iodosuccinimide), Py/Pyr (pyridine), TEMPO ((2,2,6,6-tetramethyl-1-piperdinyl)oxy), Tf (trifluoromethanesulfonyl), THF (tetrahydrofurane), TMS(trimethylsilyl), TMSOTf (trimethylsilyl trifluoromethane sulfonate), p-Ts (para-tolylsulfonyl).

Synthesis of saccharide by [2+2] glycosylation Approach

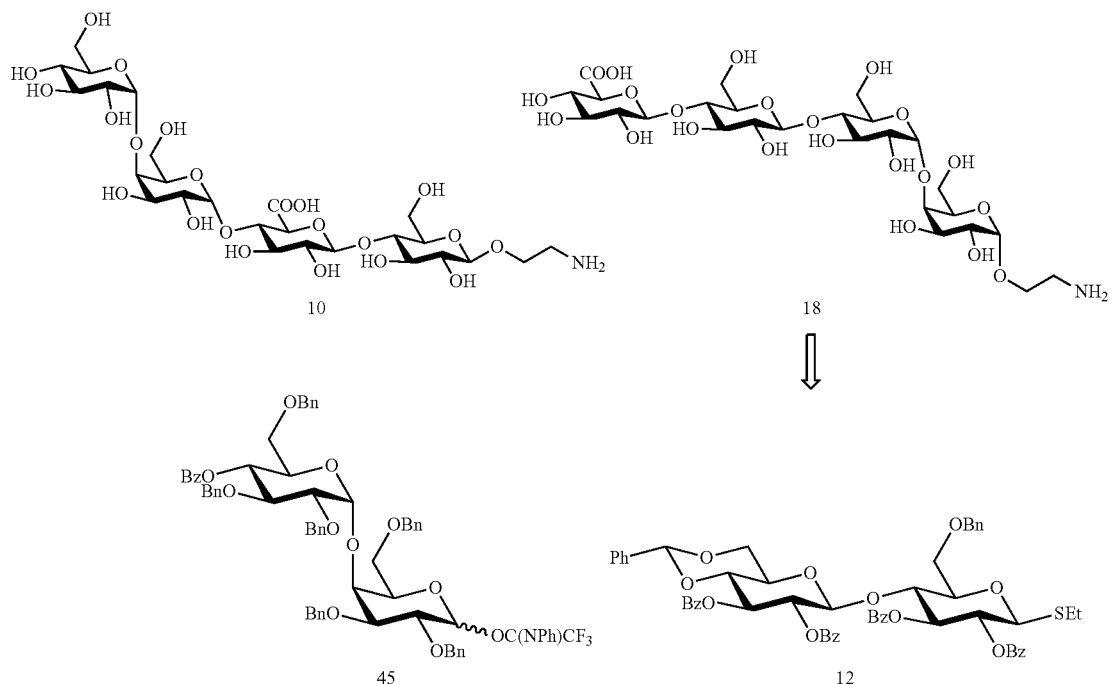

10

18

Example 1-1

Synthesis of Compound 3

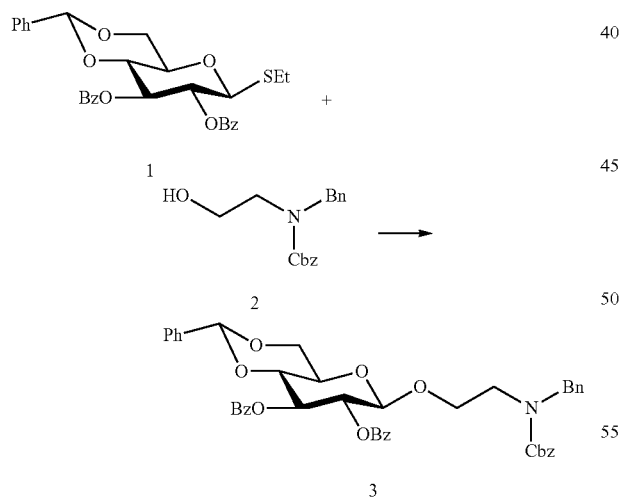

Thioglycoside donor substrate 1 (6.0 g, 11.53 mmol) and acceptor with C-2 linker 2 (dried azeotropically using toluene in rotary evaporator, 3.93 g, 13.83 mmol) were taken in dry DCM (100 mL) and added 5 g of MW dried 4 Å MS to it and stirred at rt for 15 min and then cooled to —10° C. NIS (3.83 g, 17.29 mmol) and TfOH (0.15 mL, 1.73 mmol) were then added to RM (reaction mixture) and stirred at −10° C. to −5° C. for 1 hr. Reaction completion was monitored by TLC. RM was then quenched with 10% aq. $Na_2S_2O_3$ solution (50 mL) and then extracted with EtOAc (25 ml×3). Combined organic layer was then washed with brine (10 ml), dried over anhydrous $Na_2SO_4$, filtered and concentrated in vacuum to get pale yellow oily compound. Crude product was purified on silica gel column chromatography using 20-30% EtOAc in hexanes to get spot which on evaporation yielded desired product 3 as pale yellow colored transparent gummy liquid (7.60 g, 89%).

$^1$H NMR (400 MHz, $CDCl_3$) δ=7.97 (dd, J=8.4, 1.2 Hz, 4H), 7.59-6.90 (m, 21H), 5.91-5.71 (m, 1H), 5.62-5.41 (m, 2H), 5.22-4.95 (m, 2H), 4.80 (d, J=7.7 Hz, 0.5H), 4.67 (d, J=7.7 Hz, 0.5H), 4.56-4.22 (m, 3H), 4.10-3.52 (m, 5H), 3.50-3.33 (m, 2H). $^{13}$C NMR (101 MHz, $CDCl_3$) δ=165.7, 165.4, 156.35, 156.2, 137.9, 136.9, 133.4, 133.2, 129.9, 129.5, 129.3, 129.1, 128.7, 128.5, 128.4, 128.3, 128.1, 127.8, 127.4, 127.2, 126.2, 101.9, 101.6, 78.9, 72.6, 72.1, 69.1, 68.7, 67.4, 67.2, 66.7, 51.7, 46.9, 45.8.

Example 1-2

Synthesis of Compound 4

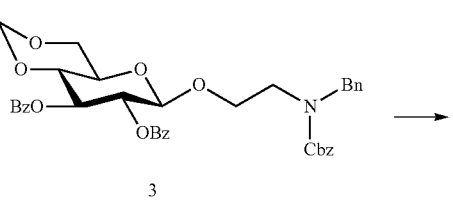

3

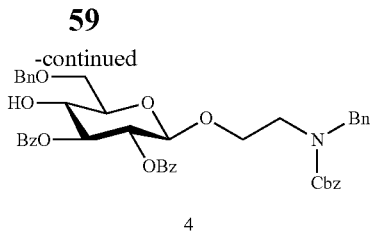

4

Substrate 3 (7.50 g, 10.08 mmol) was taken in DCM (75 mL) under argon with activated 3 Å MS for 10 min before cooling to 0° C. Added triethylsilane (12.88 mL, 81.0 mmol) followed by TFA (4.66 mL, 60.5 mmol) drop wise and stirred the RM at rt for 16 h before quenching with water (100 mL). Extracted the aqueous with DCM (30 mL×3), combined organics were washed thoroughly with water (20 mL×3), brine (20 mL), dried over anhyd. Na$_2$SO$_4$, filtered, evaporated in vacuum to get colorless gummy solid. Crude product was purified by silica column chromatography using 30%-100% EtOAc in hexanes to get product 4 and evaporated in vacuum to get colorless oil (6.1 g, 81%).

$^1$H NMR (400 MHz, CDCl$_3$) δ=8.04-7.84 (m, 4H), 7.60-6.87 (m, 21H), 5.55-5.36 (m, 2H), 5.22-4.90 (m, 2H), 4.77-4.53 (m, 3H), 4.51-4.30 (m, 2H), 4.06-3.93 (m, 2H), 3.87-3.53 (m, 4H), 3.46-3.20 (m, 3H). $^{13}$C NMR (101 MHz, CDCl$_3$) δ=167.3, 165.5, 138.0, 137.7, 133.6, 130.1, 129.9, 128.6, 128.5, 128.1, 127.9, 127.8, 127.4, 101.3, 101.2, 76.7, 74.7, 73.9, 71.6, 71.5, 71.2, 70.0, 69.0, 67.4, 67.2, 51.7, 46.8, 45.8.

Example 1-3

Synthesis of Compound 5

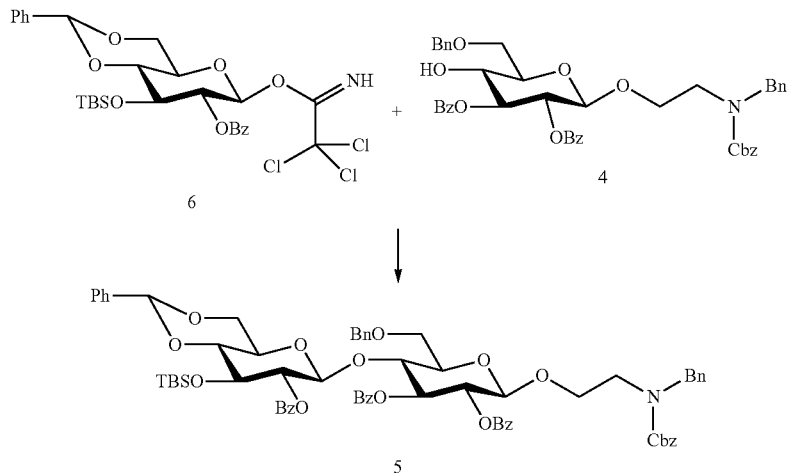

Acceptor 4 (2.0 g, 2.68 mmol) was taken in DCM (30 mL) with activated 4 Å AWMS and stirred at rt for 30 min before cooling to 0° C. TMSOTf (0.49 µL, 0.27 mmol) was then added followed by the imidate donor 6 (Carbohydrate Res 2008, 344, 439-447.) (2.20 g, 3.89 mmol) in DCM (5 mL) over 5 min and the reaction mixture was stirred for 30 min at 0° C. Quenched the RM with Et$_3$N (1 mL), filtered and the solvents removed under vacuum. Crude product was purified by flash chromatography using EtOAc in hexanes to get product 5 (3.2 g, 98%).

$^1$H NMR (400 MHz, CDCl$_3$) δ=8.13-6.88 (m, 35H), 5.67-5.52 (m, 1H), 5.46-5.31 (m, 1H), 5.20 (s, 1H), 5.16-4.89 (m, 3H), 4.68 (t, J=11.2 Hz, 1H), 4.55 (d, J=8.1 Hz, 1.5H), 4.47-4.24 (m, 3.5H), 4.20-3.89 (m, 1.5H), 3.89-3.19 (m, 9.5H), 3.13 (td, J=9.7, 4.9 Hz, 1H), 2.63 (t, J=10.2 Hz, 1H), 0.63 (s, 9H), -0.12 (s, 3H), -0.19 (s, 3H). $^{13}$C NMR (101 MHz, CDCl$_3$) δ=165.4, 165.36, 164.7, 138.2, 137.1, 133.4, 133.2, 129.94, 129.9, 129.2, 128.7, 128.6, 128.5, 128.4, 128.2, 128.0, 127.8, 127.3, 126.4, 101.7, 101.2, 101.1, 81.2, 75.5, 75.1, 74.6, 73.7, 73.4, 73.0, 68.9, 68.0, 67.3, 66.1, 51.7, 46.9, 25.6, 18.0, -4.1, -4.8.

Example 1-4

Synthesis of Compound 7

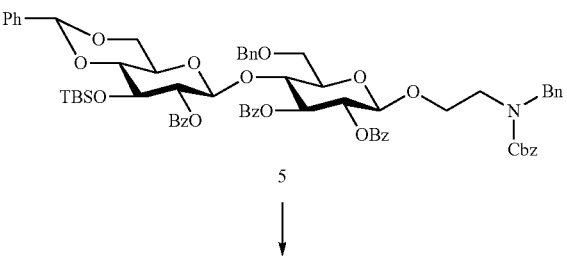

↓

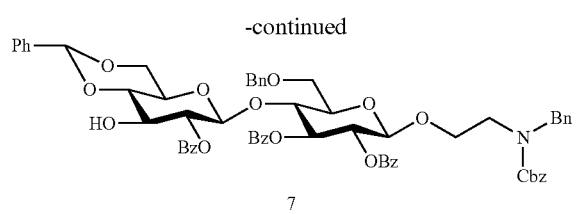

Substrate 5 (1.6 g, 1.317 mmol) was taken in pyridine (10 mL) at 0° C. and added HF-pyridine (3.56 mL, 39.5 mmol)

to it and stirred at rt for 24 h. RM was washed with water and extracted with DCM (20 mL×3). Combined organics were then washed with dil. HCl (50 mL×2), sat. NaHCO$_3$ solution (50 mL), brine (10 mL), dried over Na$_2$SO$_4$, filtered and concentrated in vacuum to get crude product which on purification using silica column chromatography using 35-40% EtOAc in hexanes yielded white colored foam 7 (1.3 g, 90%).

$^1$H NMR (400 MHz, CDCl$_3$) δ=8.15-6.92 (m, 1H), 5.65-5.51 (m, 1H), 5.44-5.30 (m, 1H), 5.23 (s, 1H), 5.11-5.04 (m, 3H), 4.77-4.49 (m, 3H), 4.49-4.24 (m, 4H), 4.25 -3.91 (m, 2H), 3.91-3.59 (m, 4H), 3.57-3.00 (m, 7H), 2.68 (t, J=10.3 Hz,1H). $^{13}$C NMR (101 MHz, CDCl$_3$) δ=165.4, 165.3, 156.4, 156.2, 138.2, 136.9, 133.6, 133.2, 130.3, 130.0, 129.9, 129.4, 128.7, 128.7, 128.5, 128.5, 128.4, 128.1, 128.1, 127.8, 127.4, 126.4, 101.8, 101.2, 101.1, 80.6, 75.9, 74.9, 74.7, 73.7, 73.5, 72.6, 72.0, 71.9, 68.9, 67.9, 67.4, 67.2, 66.0, 51.7, 46.9, 45.9.

Example 1-5

Synthesis of Compound 8

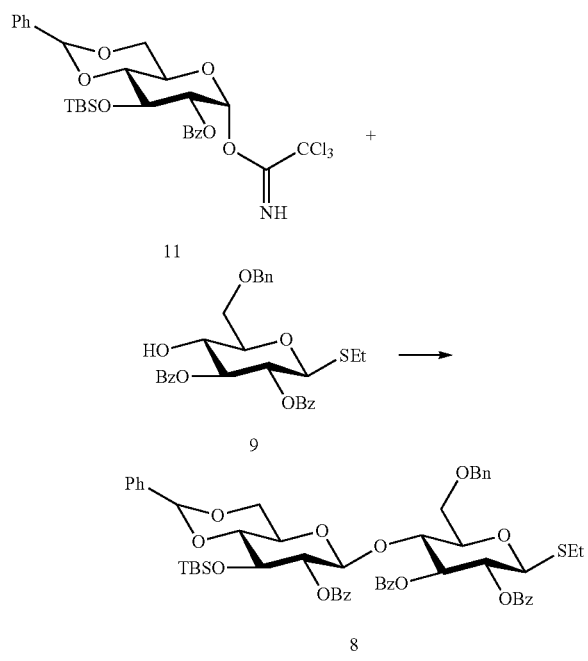

A mixture of (2S,3R,4S,5R,6R)-6-((benzyloxy)methyl)-2-(ethylthio)-5-hydroxytetrahydro-2H-pyran-3,4-diyl dibenzoate 9 (*J Carbohydrate Chemistry* 1993, 12, 309) (4.00 g, 7.654 mmol, 1.0 eq.) and (4aR,6R,7R,8aR)-8-((tert-butyldimethylsilyl)oxy)-2-phenyl-6-(2,2,2-trichloro-1-iminoethoxy)hexahydropyrano [3,2-d][1,3]dioxin-7-yl benzoate 11 (*Carbohydrate Res,* 2008, 344, 439.) (6.28 g, 9.95 mmol, 1.3 eq.) in DCM (140 mL) was stirred under an atmosphere of argon for 30 min. The reaction mixture was cooled (−20° C.) and TMSOTf (0.16 mL, 0.880 mmol, 0.115 eq.) was added. After stirring for 45 min, the reaction mixture was quenched by the addition of Et$_3$N (1.0 mL). The organic solution was concentrated under vacuo.

The resulting dark yellow oil was purified by flash chromatography over silica gel (EtOAc/hexanes, 1/3, v/v) to give (2S,3R,5R,6R)-5-(((4aR,6S,7R,8S,8aR)-7-(benzoyloxy)-8-((tert-butyldimethylsilyl)oxy)-2-phenylhexahydro pyrano-phenylhexahydropyrano[3,2-d][1,3]dioxin-6-yl)oxy)-6-((benzyloxy)methyl)-2-(ethylthio)tetrahydro-2H-pyran-3,4-diyl dibenzoate 8 (6 g, 79%) as a colorless solid: R$_f$=0.5 (EtOAc/hexanes, 3/7, v/v). $^1$H NMR (400 MHz, CDCl$_3$) δ=−0.19 (s, 3H), −0.11 (s, 3H), 0.63 (s, 9H), 1.20 (t, J=7.4 Hz, 3H), 2.67 (m, 2H), 3.15 (td, J=9.7 Hz, 4.9 Hz, 2H), 3.28 (t, J=9.2 Hz, 1H), 3.53-3.37 (m, 1H), 3.74-3.55 (m, 1H), 3.79 (t, J=9.0 Hz, 1H), 4.19 (t, J=9.5 Hz, 1H), 4.37 (d, J=12.2 Hz, 1H), 4.57 (d, J=10.0 Hz, 1H), 4.59 (dd, J=15.1, 9.0 Hz, 2H), 4.67 (d, J=12.2 Hz, 1H), 5.12 (dd, J=8.9, 8.2 Hz, 1H), 5.21 (s, 1H), 5.41 (t, J=9.8 Hz, 1H), 5.63 (t, J=9.3 Hz, 1H), 7.29-7.72 (m, 19H), 7.88-8.03 (m, 6H). $^{13}$C NMR (101 MHz, CDCl$_3$) δ=165.27, 165.07, 164.45, 138.16, 137.00, 133.14, 133.10, 132.97, 130.21, 129.79, 129.77, 129.75, 129.34, 128.99, 128.51, 128.38, 128.28, 128.22, 128.05, 128.02, 127.99, 126.21, 101.57, 101.06, 83.39, 81.05, 78.70, 77.43, 77.11, 76.80, 75.41, 74.93, 74.52, 73.49, 72.90, 70.59, 67.86, 67.45, 65.97, 25.43, 24.08, 17.80, 14.85, −4.20, −4.97.

Example 1-6

Synthesis of Compound 12

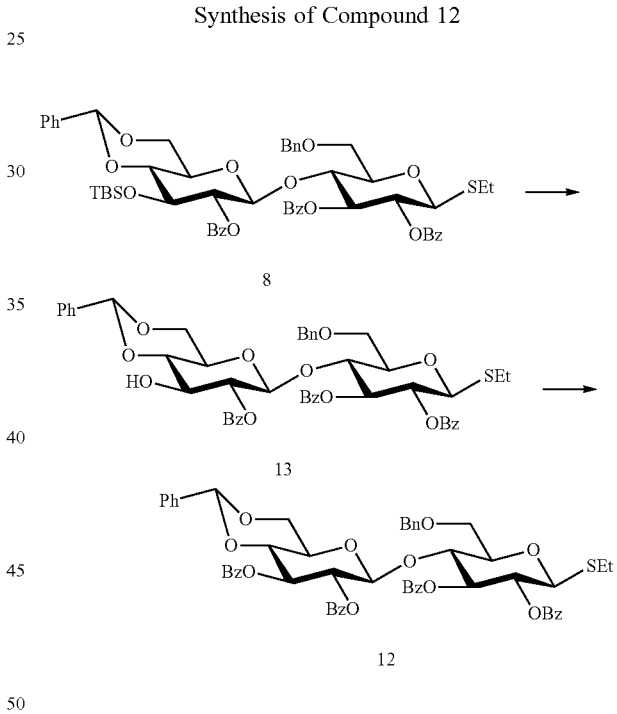

TBS substrate 8 (2.0g, 2.018 mmol, 1 equiv.) was taken in pyridine (10 mL) at 0° C. and added 70% HF-pyridine (5.45 mL, 60.5 mmo, 30 equiv.) to it and stirred at rt for 36 h.

RM was washed with water (50 mL) and extracted with DCM (50 mL×3). Combined organics were then washed with sat. NaHCO$_3$ solution (50 mL), brine (20 mL), dried over Na$_2$SO$_4$, filtered and concentrated in vacuum to get crude product which on purification using silica column chromatography using 35-40% EtOAc/Hexanes to yield white colored foam 13 (1.7g, 96%).

$^1$H NMR (400 MHz, CDCl$_3$) δ=8.08-7.85 (m, 6H), 7.69-7.28 (m, 19H), 5.62 (t, J=9.3 Hz, 1H), 5.41 (t, J=9.8 Hz, 1H), 5.22 (s, 1H), 5.08 (dd, J=9.2, 7.9 Hz, 1H), 4.70 (d, J=7.8 Hz, 1H), 4.63 (d, J=12.1 Hz, 1H), 4.58 (d, J=10.0 Hz, 1H), 4.40 (d, J=12.1 Hz, 1H), 4.19 (t, J=9.5 Hz, 1H), 3.82 (td, J=9.2, 3.6 Hz, 1H), 3.70 (dd, J=11.2, 3.4 Hz, 1H), 3.63 (dd, J=10.6, 5.0 Hz, 1H), 3.59-3.55 (m, 1H), 3.54-3.48 (m, 1H), 3.32 (t, J=9.3 Hz, 1H), 3.15 (td, J=9.7, 5.0 Hz, 1H), 2.78-2.60 (m, 3H), 2.50 (d, J=3.6 Hz, 1H), 1.22 (t, J=7.5 Hz, 3H). $^{13}$C NMR (101 MHz, CDCl$_3$) δ=165.38, 165.29, 165.13, 138.02, 136.70, 133.43, 133.14, 133.09, 130.08, 129.87, 129.81, 129.71, 129.30, 129.28, 129.23, 128.50, 128.48, 128.29, 127.95, 127.86, 126.19, 101.59, 100.88, 83.42, 80.42, 78.71, 75.71, 74.67, 74.51, 73.46, 72.42, 70.48, 67.70, 67.51, 65.76, 24.11, 14.85.

Substrate 13 (1.6g, 1.824 mmol, 1 equiv.) was taken in anhydrous DCM (10 mL) at 0° C. and added pyridine (10 mL) and BzCl (0.635 mL, 5.47 mmol, 3 equiv.) to it dropwise and RM was stirred for 16 h.

RM was then evaporated in vacuum to remove solvents and then taken again in DCM (25 mL) and washed with aq.NaHCO$_3$ solution(5 mL×2). Organic layer was then dried on Na$_2$SO$_4$, filtered and evaporated in vacuum. which was then triturated using methanol to get off-white solid (12), filtered, dried in vacuum (1.5g, 84%).

$^1$H NMR (400 MHz, CDCl$_{33}$) δ 7.95 (ddd, J=16.9, 12.1, 7.3 Hz, 8H), 7.60-7.12 (m, 22H), 5.66 (t, J=9.3 Hz, 1H), 5.58 (t, J=9.6 Hz, 1H), 5.43 (t, J=9.8 Hz, 1H), 5.36 (dd, J=9.5, 7.9 Hz, 1H), 5.20 (s, 1H), 4.77 (d, J=7.9 Hz, 1H), 4.60 (t, J=10.3 Hz, 2H), 4.39 (d, J=12.1 Hz, 1H), 4.23 (t, J=9.5 Hz, 1H), 3.74-3.43 (m, 5H), 3.29 (td, J=9.7, 4.9 Hz, 1H), 2.83-2.55 (m, 3H), 1.22 (t, J=7.4 Hz, 3H). $^{13}$C NMR (101 MHz, CDCl$_3$) δ 165.46, 165.25, 165.16, 164.72, 137.82, 136.62, 133.31, 133.12, 133.02, 130.05, 129.80, 129.73, 129.70, 129.27, 129.24, 128.99, 128.97, 128.63, 128.43, 128.29, 128.22, 128.17, 128.10, 127.98, 126.03, 101.12, 83.39, 78.65, 78.29, 75.85, 74.44, 73.44, 72.43, 71.96, 70.47, 67.71, 67.31, 66.16, 24.04, 14.84.

Example 1-7

Synthesis of 2,3-di-O-benzoyl-β-D-glucopyranosyl-(1→4)-2,3-di-O-benzoyl-6-O-benzyl-β-D-glucoyranosyl-(1→1)-(2-N-benzyl-N-benzyloxycarbonylamino)ethanol (14)

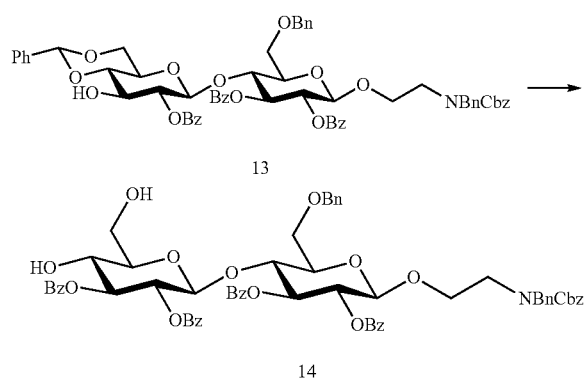

To a stirred solution of alcohol 13 (400 mg, 0.36 mmol) in pyridine (5.0 mL) was added at 0° C. benzoyl chloride (63 μL, 0.55 mmol). The reaction was slowly warmed to room temperature and stirred for 16 h at that temperature. An additional 0.5 equiv. BzCl were added to drive the reaction to completion. The mixture was stirred for 2 h at room temperature, quenched with water (30 ml) and diluted with EtOAc (50 mL). After separation, the organic fraction was washed with 0.1 M HCl (20 mL) and the aqueous fraction was re-extracted with EtOAc (30 mL). The combined organic fractions were washed with sat. aq. NaHCO$_3$ (20 mL) and brine (10 mL), dried over Na$_2$SO$_4$ and concentrated to give the intermediate tetrabenzoate as a yellow oil. To a stirred solution of the intermediate tetrabenzoate in CH$_2$Cl$_2$ (6.5 mL) were added at room temperature ethanethiol (0.36 mL, 4.9 mmol) and p-toluenesulfonic acid (12 mg, 0.06 mmol). The mixture was stirred for 2 h at that temperature, quenched with Et$_3$N (50 μL) and concentrated. The residue was purified by flash chromatography (EtOAc/hexanes 0:1 to 1:10 to 1:8) to give diol 14 (389 mg, 0.349 mmol) as a white foam. HRMS (ESI) calcd. for C$_{64}$H$_{61}$NO$_{17}$ (M+Na)$^+$ 1138.3837 found 1138.3850 m/z.

Example 1-8

Synthesis of methyl(2,3-di-O-benzoyl-β-D-glucopyranosyl)uronate-(1→4)-2,3-di-O-benzoyl-6-O-benzyl-β-D-glucoyranosyl-(1→1)-(2-N-benzyl-N-benzyloxycarbonylamino)ethanol (15)

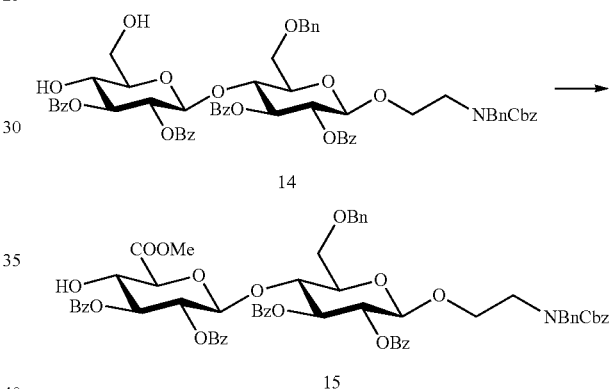

To a stirred solution of alcohol 14 (90 mg, 0.081 mmol) in CH$_2$Cl$_2$ (2.0 mL) and water (0.8 mL) were added at 0° C. TEMPO (2.5 mg, 0.016 mmol) and BAIB (55 mg, 0.170 mmol). The reaction was stirred for 20 min at that temperature and warmed to room temperature. The mixture was stirred for 2 h at that temperature and diluted with EtOAc (20 mL) and water (10 mL). After separation, the aqueous fraction was extracted with EtOAc (2×10 mL), the combined organic fractions were dried over Na$_2$SO$_4$ and concentrated. The residue was purified by flash chromatography (EtOAc/hexanes 1:2 to 1:1, then 1:1+5% AcOH) to give the intermediate carboxylic acid as a white foam.

To a stirred solution of the intermediate carboxylic acid in toluene (1.6 mL) and MeOH (0.8 mL) was added at room temperature TMS-diazomethane (0.04 mL, 0.081 mmol). The reaction was stirred for 2 h at that temperature. An additional 0.25 equiv. TMS-diazomethane was added to drive the reaction to completion. The mixture was stirred for 1 h at that temperature, quenched with AcOH (0.1mL) and concentrated. The residue was purified by flash chromatography (EtOAc/hexanes 0:1 to 1:1) to give methyl ester 15 (73 mg, 0.064 mmol, 79% over two steps) as a clear oil. HRMS (ESI) calcd. for C$_{65}$H$_{61}$NO$_{18}$ (M+Na)$^+$ 1166.3786 found 1166.3762 m/z.

Example 1-9

Synthesis of t-hexyl 2,3,6-tri-O-benzyl-β-D-galactopyranoside (17)

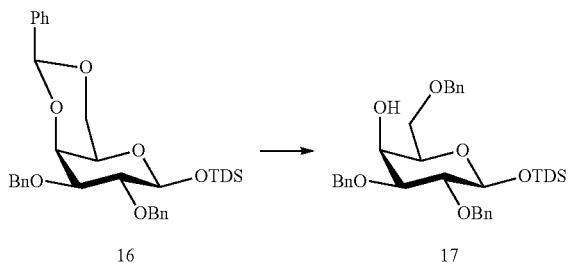

To a stirred solution of benzylidene acetal 16 (*J Carbohyd Chem* 1996, 15 (2), 241) (1.68 g, 2.84 mmol) in CH$_2$Cl$_2$ (60 mL) over activated MS (3 Å-AW) were added at 0° C. triethyl silane (2.72 mL, 17.06 mmol) and trifluoroacetic acid (1.81 mL, 17.06 mmol). The reaction was slowly warmed to room temperature and stirred for 16 h at that temperature. The reaction was quenched with Et$_3$N (2 mL), filtered through Celite and concentrated. The residue was purified by flash chromatography (EtOAc/hexanes 1:20 to 1:7) to give alcohol 17 (1.46 g, 2.46 mmol, 87%) as a clear oil. HRMS (ESI) calcd. for C$_{35}$H$_{48}$O$_6$Si (M+Na)$^+$ 615.3117 found 615.3104 m/z.

Example 1-10

Synthesis of tHexyl 4-O-benzoyl-2,3,6-tri-O-benzyl-α-D-glucopyranosyl-(1→4)-2,3,6-tri-O-benzyl-O-D-galactopyranoside (44)

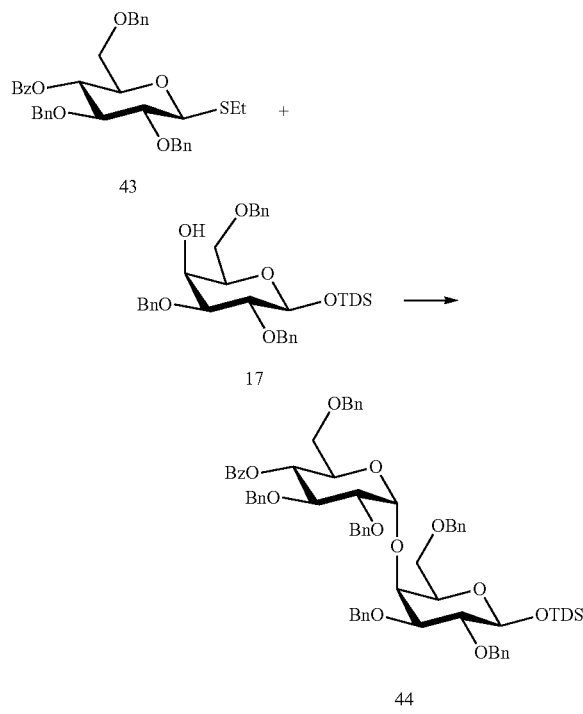

Thioglycoside 43 (*J. Org. Chem.* 2012, 77 (1), 291). (667 mg, 1.11 mmol) and alcohol 17 (550 mg, 0.93 mmol) were co-evaproated with dry toluene (3×10 mL) and kept under high vacuum for 30 min. The mixture was dissolved in Et$_2$O (14 mL) and CH$_2$Cl$_2$ (2.8 mL) and stirred over activated molecular sieves (3 Å-AW) for 30 min at room temperature. The solution was cooled to −20° C. and treated with NIS (250 mg, 1.11 mmol) and triflic acid (16 μL, 0.19 mmol). The mixture was stirred for 1 h and slowly warmed to −10° C. The reaction was quenched with Et$_3$N (0.05 mL), diluted with CH$_2$Cl$_2$ (20 mL), filtered through Celite and concentrated. The residue was purified by flash chromatography (EtOAc/hexanes 0:1 to 1:8 to 1:6) to give disaccharide 44 (553 mg, 0,490 mmol, 53%) along with the corresponding β-anomer (231 mg, 0.205 mmol, 22%). Analytical data for 7: Clear oil. HRMS (ESI) calcd. for C$_{69}$H$_{80}$O$_{12}$Si (M+Na)$^+$ 1151.5316 found 1151.5293 m/z.

Example 1-11

Synthesis of 4-O-benzoyl-2,3,6-tri-O-benzyl-α-D-glucopyranosyl-(1→4)-2,3,6-tri-O-benzyl-αβ-D-galactopyranosyl trifluoro-(N-phenyl)acetimidate (45)

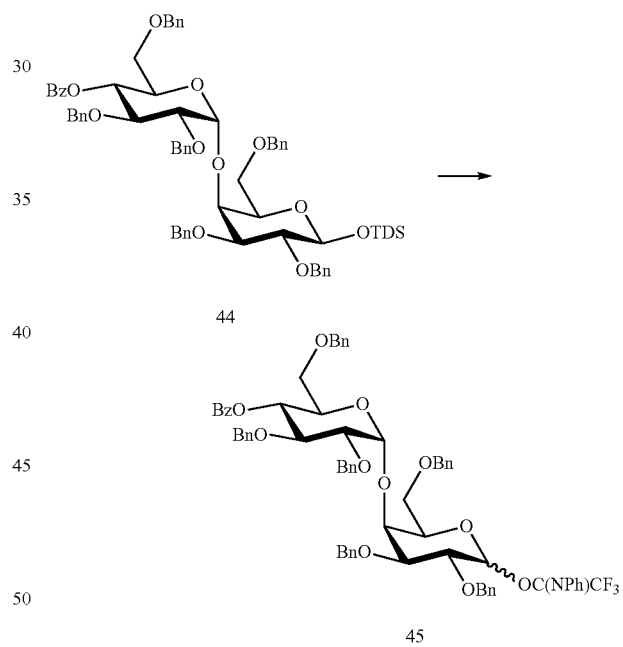

To a stirred solution of silyl ether 44 (470 mg, 0.416 mmol) in THF (8.3 mL) was added at 0° C. acetic acid (0.24 mL, 4.19 mmol) and TBAF (1.0 M solution in THF, 4.2 mL, 4.20 mmol). The reaction was slowly warmed to room temperature and stirred for 2 h at that temperature. Acetic acid (0.24 mL, 4.19 mmol) and TBAF (1.0 M solution in THF, 4.2 mL, 4.20 mmol) were added and the reaction was stirred for 16 h at room temperature. The mixture was diluted with Et$_2$O (50 mL), washed with water (3×30 mL) and the aqueous phase was re-extracted with Et$_2$O (2×20 mL). The combined organic fractions were dried over Na$_2$SO$_4$ and concentrated. The residue was filtered through a short plug of silica gel (EtOAc/hexanes 1:3 to 1:1) to give the intermediate lactol mixture as a clear oil.

To a stirred solution of the lactol mixture in CH$_2$Cl$_2$ (7.8 mL) were added at room temperature cesium carbonate (318 mg, 0.975 mmol) and F$_3$CC(NPh)Cl (202 mg, 0.975 mmol). The mixture was stirred for 2.5 h at that temperature, diluted with hexanes (0.5% (v/v) Et$_3$N, (10 mL) and filtered through Celite. The residue was purified by flash chromatography (EtOAc/hexanes 0:1+0.5% Et$_3$N to 1:3+0.5% Et$_3$N) to give imidate mixture 45 (404 mg, 0.349 mmol, 84% over two steps) as a clear oil. HRMS (ESI) calcd. for C$_{69}$H$_{66}$F$_3$NO$_{12}$ (M+Na)$^+$ 1180.4434 found 1180.4458 m/z.

Example 1-12

Synthesis of 4-O-benzoyl-2,3,6-tri-O-benzyl-α-D-glucopyranosyl-(1→4)-2,3,6-tri-O-benzyl-α-D-galactopyranosyl-(1→4)-methyl [2,3-Di-O-benzoyl-β-D-glucopyranosyl]uronate-(1→4)-2,3-di-O-benzoyl-6-O-benzyl-β-D-glucoyranosyl-(1→1)-(2-N-benzyl-N-benzyloxycarbonylamino)ethanol (46)

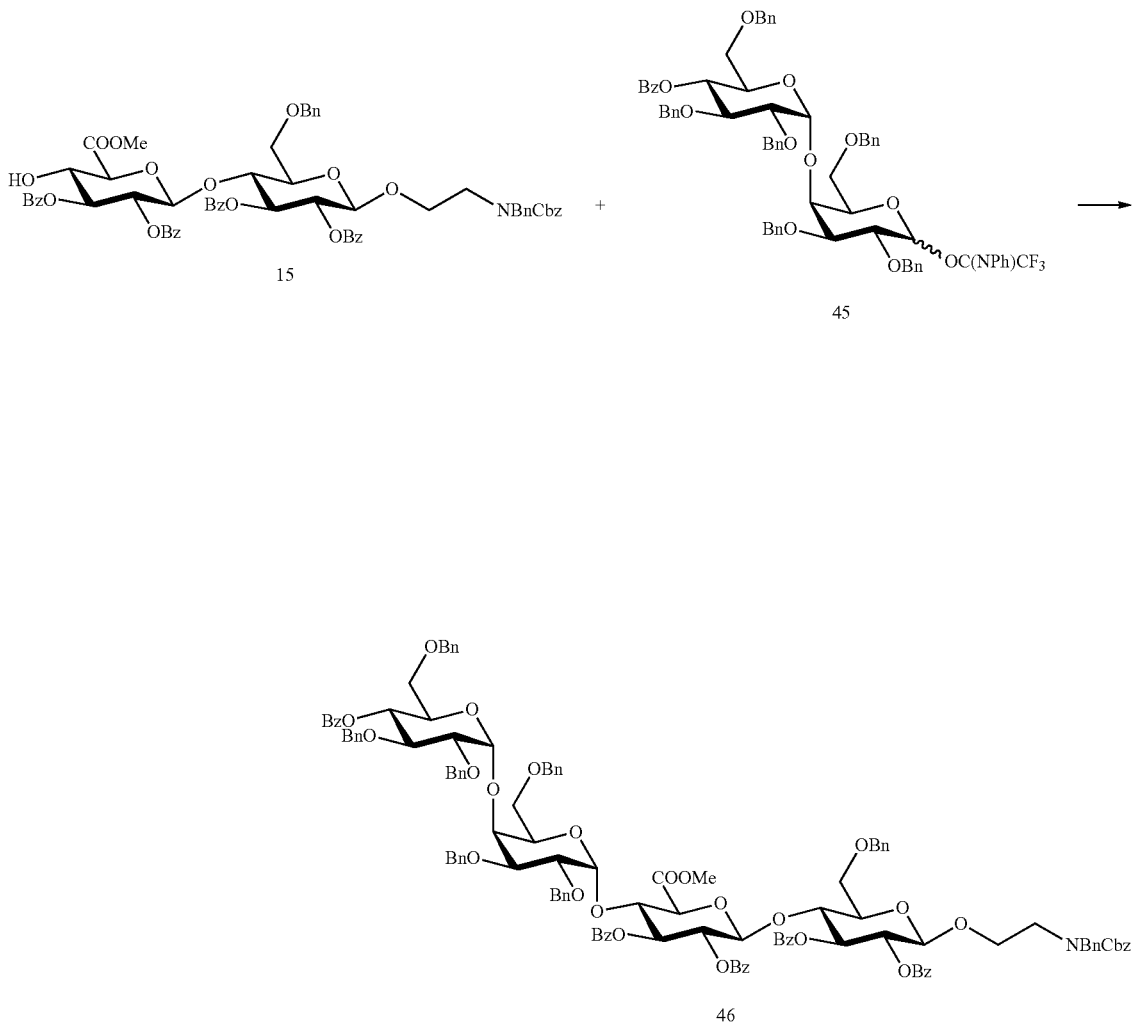

Alcohol 15 (100 mg, 87 μmol) and imidate 45 (121 mg, 105 μmol) were co-evaporated with dry toluene (3×10 mL) and kept under high vacuum for 30 min. The mixture was dissolved in Et$_2$O (3.3 mL) and CH$_2$Cl$_2$ (1.1 mL) and stirred over activated molecular sieves (3 Å-AW) for 30 min at room temperature. The solution was cooled to −20° C. and treated with TMSOTf (3.2 μL, 17 μmol). The mixture was stirred for 1 h and slowly warmed to 0° C. The reaction was quenched with sat. aq. NaHCO$_3$ (10 mL), extracted with CH$_2$Cl$_2$ (3×20 mL) and the combined organic fractions were dried over Na$_2$SO$_4$ and concentrated. The residue was purified by flash chromatography (EtOAc/hexanes/toluene 1:3:3 to 1:2:2) to give tetrasaccharide 46 (130 mg, 62 μmol, 71%) as a clear oil. HRMS (ESI) calcd. for C$_{126}$H$_{121}$NO$_{29}$ (M+Na)$^+$ 2134.7921 found 2134.7879 m/z.

Example 1-13

Synthesis of α-D-glucopyranosyl-(1→4)-α-D-galactopyranosyl-(1→4)-β-D-glucopyranosyluronic acid-(1→4)-β-D-glucoyranosyl-(1→1)-(2-amino)ethanol (10)

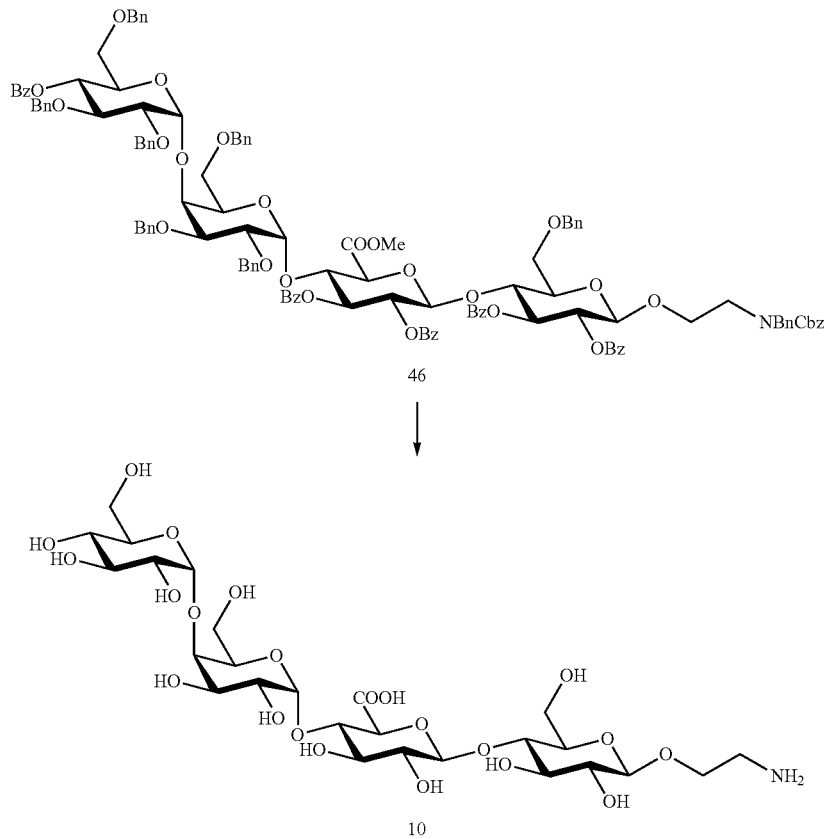

To a stirred solution of ester 46 (56 mg, 26 μmol) in THF (5 mL) and MeOH (1 mL) were added at 0° C. hydrogen peroxide (6% aq. solution, 265 μL, 530 μmol) and LiOH (1 M aq. solution, 265 μL, 132 mol). The reaction was stirred for 1 h and warmed to room temperature. The reaction was kept at that temperature and treated after 2 h with hydrogen peroxide (6% aq. solution, 265 μL, 530 μmol) and LiOH (1 M aq. solution, 265 μL, 132 mol). After 2 h, NaOH (15% aq. solution, 1 mL) was added and the mixture was stirred for 72 h at room temperature. The solvents were evaporated under reduced pressure, the residue was co-evaporated with toluene (2μ5 mL) and dissolved in MeOH (5 mL). The solution was treated at room temperature with sodium methoxide (143 mg, 2.65 mmol) and stirred for 96 h at that temperature. The solvent was evaporated and the residue was dissolved in water (5 mL). The solution was neutralized at 0° C. with 0.5 M aq. NaHSO$_4$ and extracted with EtOAc (5×5 mL). The combined organic fractions were dried over Na$_2$SO$_4$ and concentrated to give the intermediate acid as a white foam.

The intermediate acid in MeOH (2 mL) was added at room temperature to a suspension of Pd/C (50 mg) in MeOH (1 mL), water (0.1 mL) and AcOH (5 drops). The reaction was stirred under an atmosphere of H$_2$ for 48 h, filtered and concentrated. The residue was purified by solid phase extraction (Chromabond C18, Macherey-Nagel) and lyophilized to give tetrasaccharide 10 (acetate salt, 13.6 mg, 18 μmol, 69% over 3 steps) as a white solid. HRMS (MALDI) calcd. for $C_{26}H_{45}NO_{22}$ (M+Na)$^+$ 746.2330 found 746.2323 m/z.

Example 1-14

Synthesis of 4-O-Benzoyl-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (47)

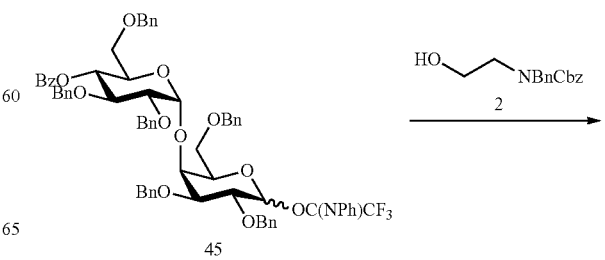

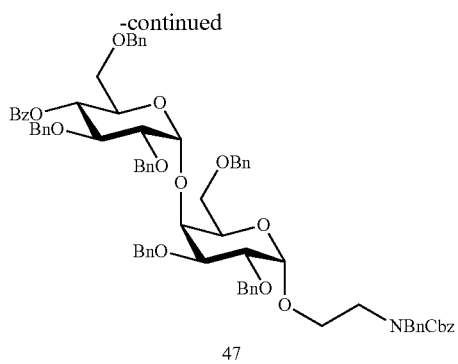

47

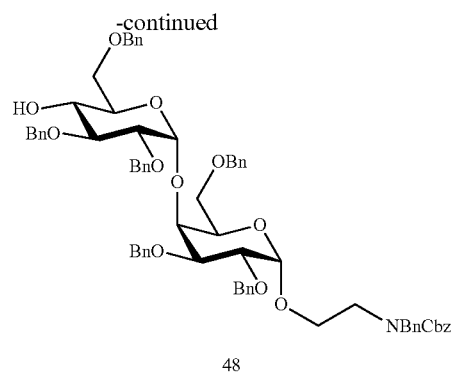

48

Imidate 45 (200 mg, 0.173 mmol) and alcohol 2 (74 mg, 0.259 mmol) were co-evaproated with dry toluene (2×5 mL) and kept under high vacuum for 30 min. The mixture was dissolved in Et$_2$O (2.8 mL) and CH$_2$Cl$_2$ (0.7 mL) and stirred over activated molecular sieves (3 Å-AW) for 30 min at room temperature. The solution was cooled to −40° C. and treated with TMSOTf (6.2 μL, 35 μmol). The mixture was stirred for 10 min at that temperature and then slowly warmed to −10° C. The reaction was quenched with sat. aq. NaHCO$_3$ (5 mL), extracted with CH$_2$Cl$_2$ (3×20 mL) and the combined organic fractions were dried over Na$_2$SO$_4$ and concentrated. The residue was purified by flash chromatography (EtOAc/hexanes 0:1 to 1:6 to 1:4) to give carbamate 47 (160 mg, 0.128 mmol, 74%) along with the corresponding β-anomer (32 mg, 0.026 mmol, 15%). Analytical data for 47: Clear oil. HRMS (ESI) calcd. for C$_{78}$H$_{79}$NO$_{14}$ (M+Na)$^+$ 1276.5398 found 1276.5405 m/z.

To a stirred solution of ester 47 (126 mg, 0.100 mmol) in THF (5 mL) and MeOH (5 mL) was added at 0° C. sodium methoxide (0.5 M in MeOH, 1 mL, 0.500 mmol). The reaction was slowly warmed to room temperature and kept at that temperature for 24 h. Sodium methoxide (0.5 M in MeOH, 1 mL, 0.500 mmol) was added and the reaction was warmed to 37° C. The mixture was stirred for 7 h at that temperature, neutralized with Amberlite IR120 (H$^+$form), filtered and concentrated. The residue was purified by flash chromatography (EtOAc/hexanes 0:1 to 1:6 to 1:4) to give alcohol 48 (98 mg, 85 μmol, 85%) as a clear oil. HRMS (ESI) calcd. for C$_{71}$H$_{75}$NO$_{13}$ (M+Na)$^+$ 1172.5136 found 1172.5103 m/z.

Example 1-16

Syntheis of α-D-glucopyranosyl-(1→4)-α-D-galactopyranosyl-(1→1)-(2-amino)ethanol (49)

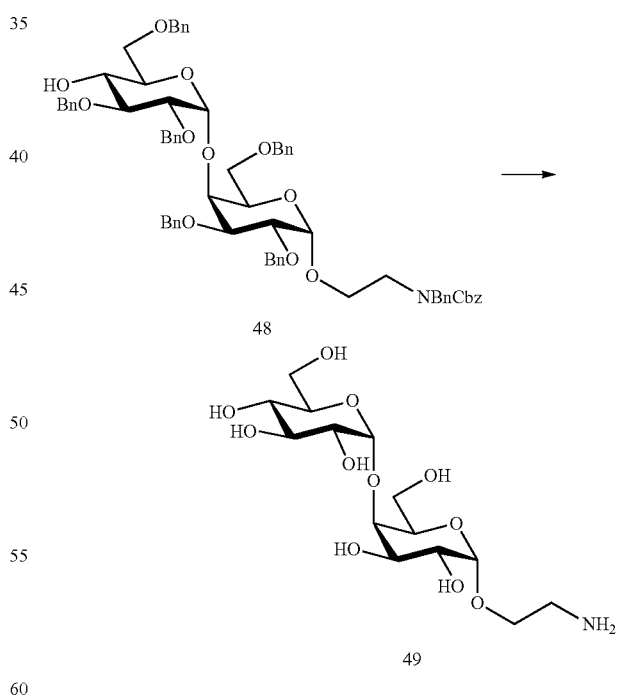

Example 1-15

Synthesis of 2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (48)

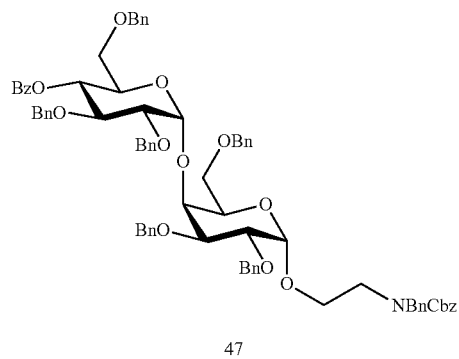

47

Benzyl ether 48 in EtOAc (1 mL) was added at room temperature to a suspension of Pd/C (30 mg) in MeOH (3 mL), water (0.5 mL) and AcOH (3 drops). The reaction was stirred under an atmosphere of H$_2$ for 24 h, filtered and concentrated to give disaccharide 49 (2.9 mg, 18 μmol, 87%) as a white solid. HRMS (ESI) calcd. for C$_{14}$H$_{27}$NO$_{11}$ (M+Na)$^+$ 408.1481 found 408.1499 m/z.

Example 1-17

Synthesis of 2,3-di-O-benzoyl-β-D-glucopyranosyl-(1→4)-2,3-di-O-benzoyl-6-O-benzyl-β-D-glucoyra-nosyl-(1→4)-2,3,6-tri-O-benzyl-α-D-glucopyrano-syl-(1→4)-2,3,6-tri-O-benzyl-α-D-galactopyranosyl-(1→1)-(2-N-benzyl-N-benzyloxycarbonylamino) ethanol (50)

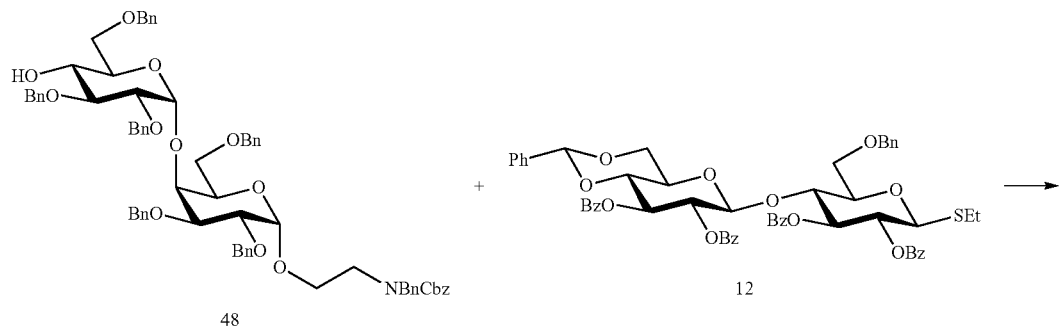

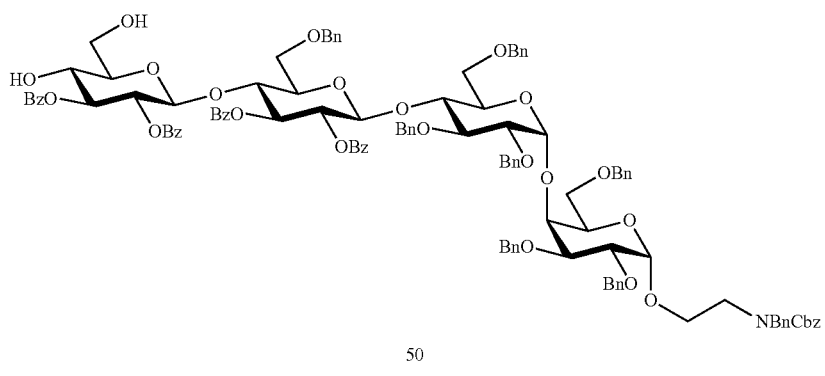

Alcohol 48 (47 mg, 41 µmol) and thioglycoside 12 (60 mg, 61 µmol) were co-evaporated with dry toluene (2×5 mL) and kept under high vacuum for 30 min. The mixture was dissolved in $CH_2Cl_2$ (2 mL) and stirred over activated molecular sieves (3 Å-AW) for 30 min at room temperature. The solution was cooled to −10° C. and treated with NIS (13.8 mg, 61 µmol) and triflic acid (1 µL, 11 µmol). The mixture was kept for 1 h at that temperature and slowly warmed to 0° C. The reaction was quenched with $Et_3N$ (50 µL), filtered and concentrated to give the intermediate benzylidene acetal as a yellow oil.

To a stirred solution of the intermediate benzylidene acetal in $CH_2Cl_2$ (2 mL) were added at room temperature ethanethiol (0.3 mL, 4.06 mmol) and p-toluenesulfonic acid (10 mg, 0.053 mmol). The mixture was stirred for 1 h at that temperature, quenched with $Et_3N$ (20 µL) and concentrated. The residue was purified by flash chromatography (EtOAc/hexanes 0:1 to 1:3 to 1:2) to give diol 50 (78 mg, 39 µmol, 96%) as a clear oil. HRMS (ESI) calcd. for $C_{118}H_{117}NO_{27}$ $(M+Na)^+$ 2002.7710 found 2002.7731 m/z.

Example 1-18

Synthesis of 2,3-di-O-benzoyl-β-D-glucopyranosyluronate-(1→4)-2,3-di-O-benzoyl-6-O-benzyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (51)

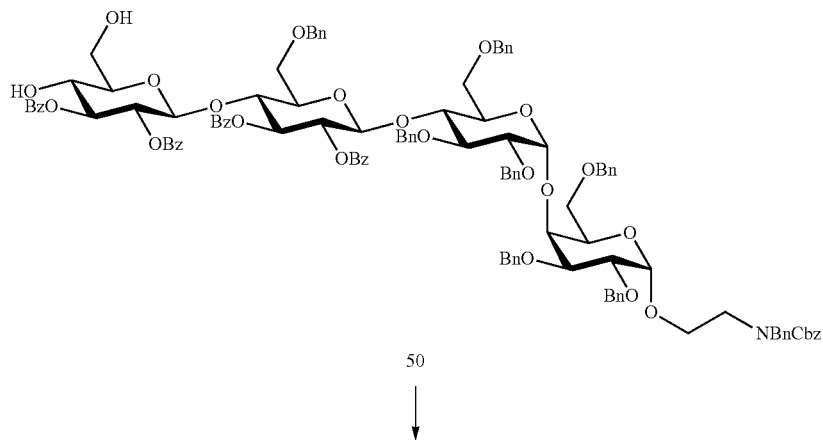

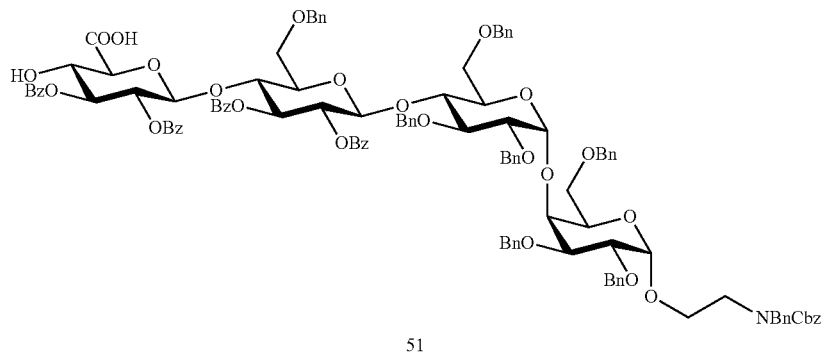

To a vigorously stirred solution of alcohol 50 (45 mg, 23 μmol, 73%) in $CH_2Cl_2$ (2 mL) and water (0.8 mL) were added at 0° C. TEMPO (3 crystals) and BAIB (15.4 mg, 48 μmol). The reaction was stirred for 20 min at that temperature and slowly warmed to room temperature. After 1 h, TEMPO (2 crystals) and BAIB (10 mg, 31 μmol) were added and the mixture was stirred for 2 h at room temperature. The reaction was diluted with $CH_2Cl_2$ (5 mL) and quenched with 10% aq. $Na_2S_2O_3$ (5 mL). Following separation, the aqueous phase was extracted with EtOAc (2×10 mL), the combined organic fractions were dried over $Na_2SO_4$ and concentrated. The residue was purified by flash chromatography twice (EtOAc/hexanes 0:1 to 1:2 to 8:1, then EtOAc/hexanes 1:1+1% AcOH) and co-evaporated with heptane repeatedly to give acid 51 (33 mg, 17 μmol, 74%) as a clear oil. HRMS (ESI) calcd. for $C_{118}H_{115}NO_{28}$ $(M+Na)^+$ 2016.7503 found 2016.7558 m/z.

Example 1-19

Synthesis of β-D-Glucopyranosyluronic acid-(1→4)-β-D-glucoyranosyl-(1→4)-α-D-glucopyranosyl-(1→4)-α-D-galactopyranosyl-(1→1)-(2-amino)ethanol (18)

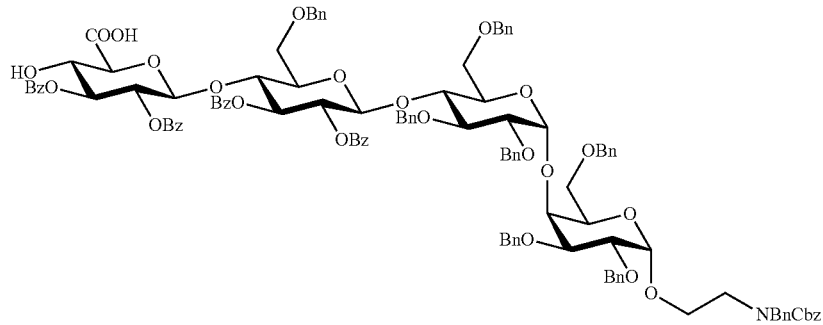

51

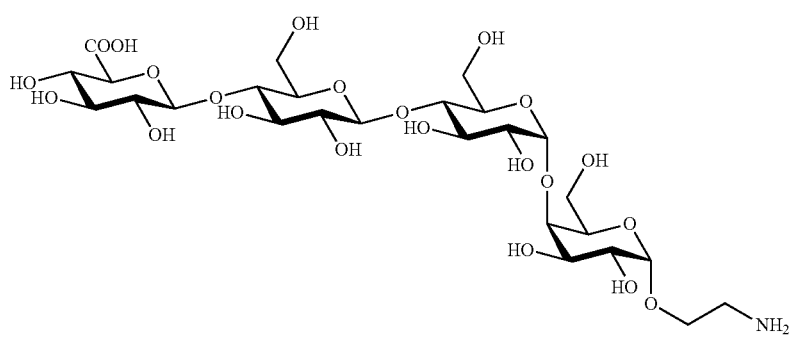

18

To a stirred solution of ester 51 (45 mg, 23 μmol) in THF (4 mL) and MeOH (0.5 mL) were added at 0° C. NaOH (1 M aq. solution, 1 mL). The reaction was slowly warmed to room temperature and stirred for 16 h at that temperature. The solution was neutralized at 0° C. with 0.5 M aq. NaHSO$_4$ and extracted with EtOAc (5×5 mL). The combined organic fractions were dried over Na$_2$SO$_4$ and concentrated to give the intermediate alcohol as a white foam.

The intermediate alcohol in MeOH (3 mL) was added at room temperature to a suspension of Pd/C (20 mg) in MeOH (6 mL), water (6 drops) and AcOH (3 drops). The reaction was stirred under an atmosphere of H$_2$ for 96 h, filtered and concentrated. Since the reaction had not proceeded to completion, the residue was subjected to the same conditions again and stirred for 72 h at room temperature. The reaction was filtered and concentrated, the residue was purified by solid phase extraction (Chromabond C18, Macherey-Nagel) and lyophilized to give tetrasaccharide 18 (11.3 mg, 16 μmol, 68% over 2 steps) as a white solid. HRMS (MALDI) calcd. for C$_{26}$H$_{45}$NO$_{22}$ (M+Na)$^+$ 746.2330 found 746.2416 m/z.

Example 1-20

Synthesis of methyl[2,3-di-O-benzoyl-β-D-glucopy-ranosyl]uronate-(1→4)-2,3-di-O-benzoyl-6-O-ben-zyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (52)

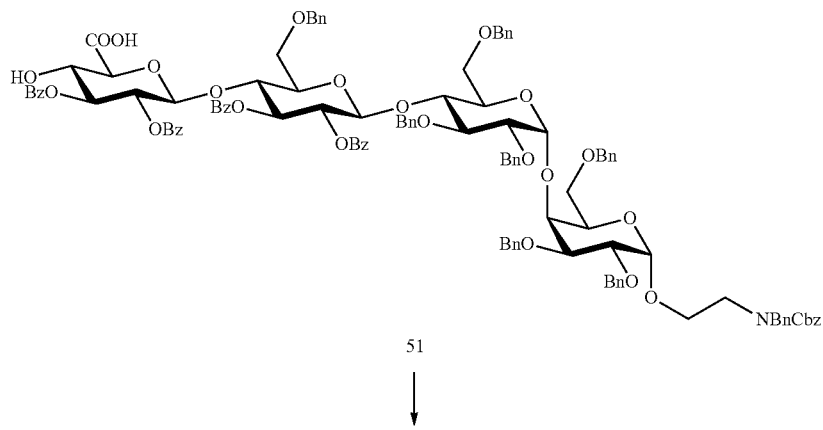

51

↓

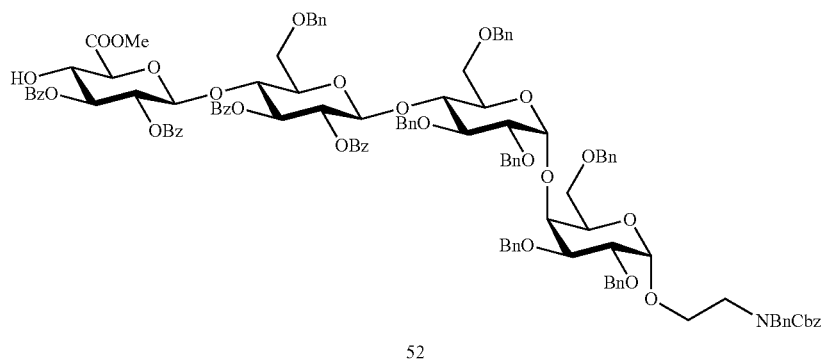

52

To a stirred solution of carboxylic acid 51 (100 mg, 50 μmol) in DMF (2.5 mL) were added at room temperature Cs$_2$CO$_3$ (24.5 mg, 75 μmol) and methyl iodide (10.7 mg, 75 μmol) and the reaction was stirred at that temperature. After 2 h, methyl iodide (10.7 mg, 75 μmol) was added and the mixture was stirred for another 2 h at room temperature. The reaction was quenched with sat. aq. NH4Cl (5 mL), extracted with EtOAc (4×10 mL), the combined organic extracts were dried over Na2SO4 and concentrated. The residue was purified by flash chromatography (EtOAc/hexanes 0:1 to 2:3) to give methyl ester 52 (81 mg, 40 μmol, 80%) as a white foam. HRMS (MALDI) calcd. for C119H117NO28 (M+Na)+2030.7659 found 2030.7660 m/z.

Example 1-21

Synthesis of 2,3,4,6-tetra-O-benzyl-α-D-galactopyranosyl-(1→4)-methyl[2,3-di-O-benzoyl-β-D-glucopyranosyl]uronate-(1→4)-2,3-di-O-benzoyl-6-O-benzyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (53)

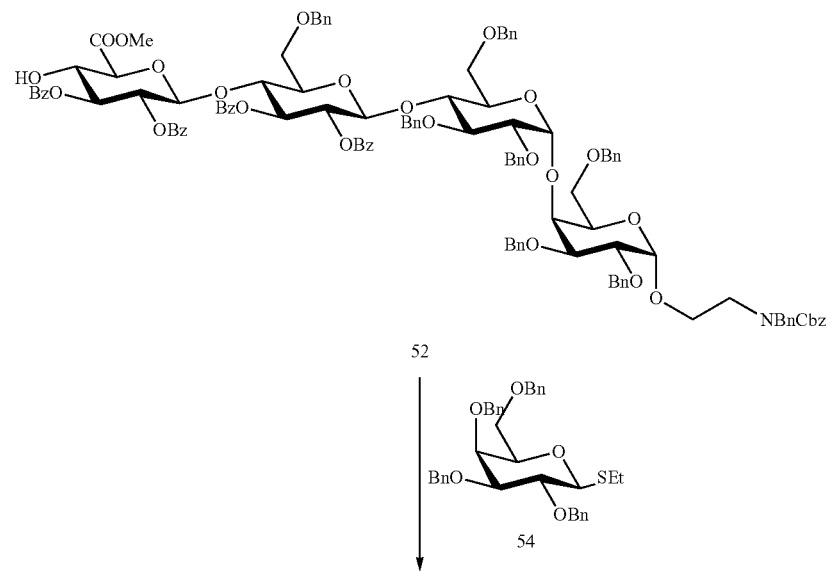

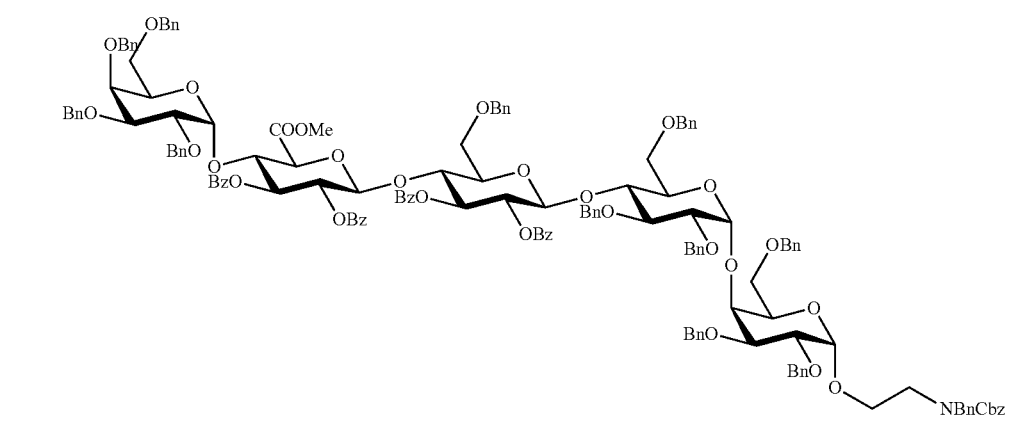

Alcohol 52 (14 mg, 7 μmol) and thioglycoside 54 (*J Org Chem* 1990, 55, 2860.) (16.3 mg, 28 μmol) were co-evaporated with dry toluene (3×10 mL) and kept under high vacuum for 30 min. The mixture was dissolved in Et$_2$O (1.05 mL) and CH$_2$Cl$_2$ (0.35 mL) and stirred over activated molecular sieves (3 Å-AW) for 30 min at room temperature. The solution was cooled to −20° C. and treated with NIS (6.3 mg, 28 pmol) and TMSOTf (1 μL, 5.5 μmol). The mixture was stirred for 1 h and slowly warmed to 0° C. The reaction was quenched with a 1:1 (v/v) mixture of sat. aq. NaHCO$_3$ (10 mL) and 10% (w/v) Na$_2$SO$_3$ (5 mL) and extracted with CH$_2$Cl$_2$ (4×10 mL). The combined organic fractions were dried over Na$_2$SO$_4$ and concentrated. The residue was purified by flash chromatography (EtOAc/hexanes 0:1 to 1:4 to 1:3) to give pentasaccharide 53 (12.5 mg, 4.9 μmol, 71%) as a clear oil. HRMS (MALDI) calcd. for C$_{126}$H$_{121}$NO$_{29}$ (M+Na)$^+$ 2553.0066 found 2553.0066 m/z.

Example 1-22

Synthesis of α-D-galactopyranosyl-(1→4)-β-D-glucopyranosyluronate-(1→4)-β-D-glucoyranosyl-α-D-glucopyranosyl-(1→4)-α-D-galactopyranosyl-(1→1)-(2-amino)ethanol (55)

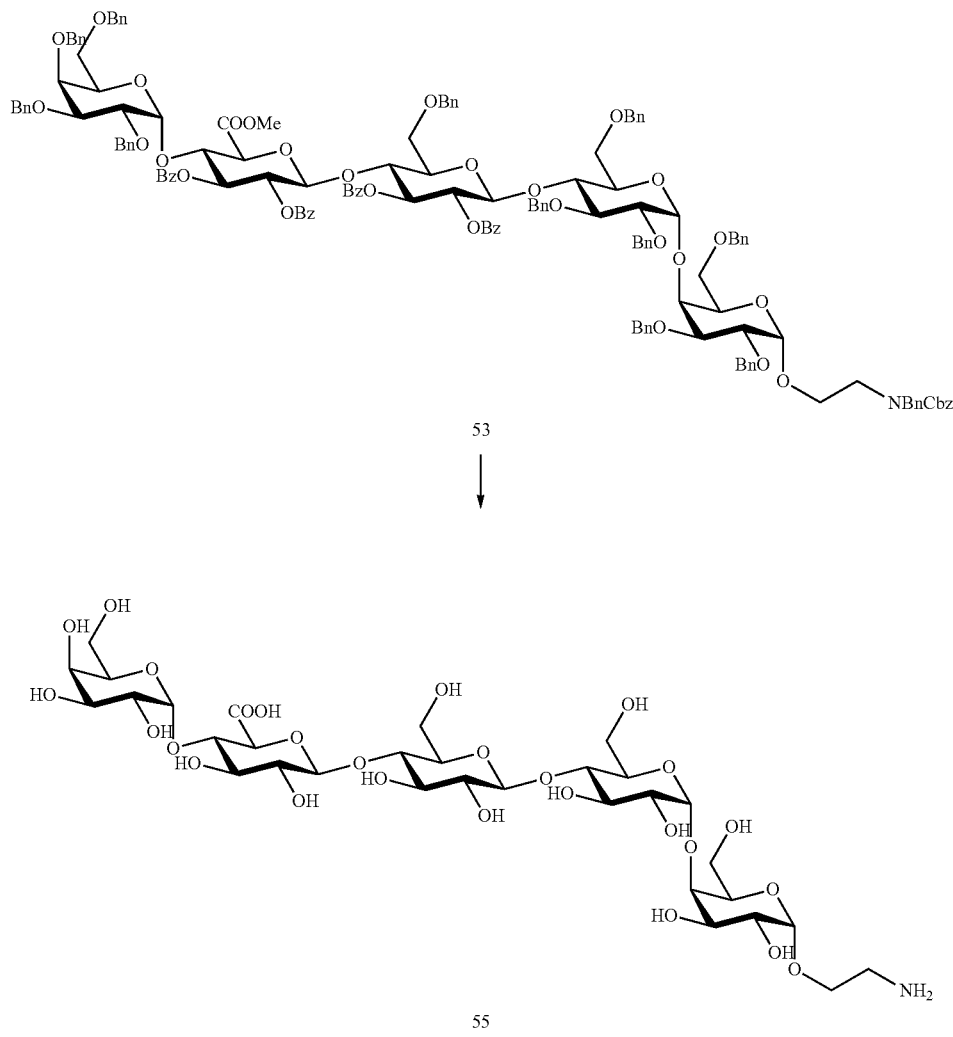

To a stirred solution of ester 53 (26 mg, 10.3 μmol) in THF (1 mL) and MeOH (1 mL) was added at 0° C. a 1:1 (v/v) mixture (450 μL) of hydrogen peroxide (6% (v/v) aq. solution, 397 μmol) and LiOH (0.5 M aq. solution, 113 μmol). The reaction was warmed to room temperature and stirred for 1 h at that temperature. The reaction was treated with NaOH (0.5 M aq. solution, 1 mL) and stirred for 16 h at room temperature. The solvents were evaporated under reduced pressure, the residue was co-evaporated with toluene (2×5 mL) and dissolved in MeOH (1 mL). The solution was treated at room temperature with NaOMe (0.5 M in MeOH, 1 mL) and stirred for 16 h at that temperature. The reaction was diluted with water (0.5 mL) and CH$_2$Cl$_2$ (0.5 mL), neutralized at 0° C. with Amberlite IR-120 (H$^+$form), filtered and concentrated. The residue was purified by flash chromatography (EtOAc/hexanes 0:1 to 1:4 to 1:2 to 1:2+1% (v/v) AcOH to 1:1+1% (v/v) AcOH) to give the intermediate carboxylic acid as a clear oil.

The intermediate carboxylic acid in CH$_2$Cl$_2$/tBuOH/water (1:16:8, 1 mL) was purged with argon and treated at 0° C. with a suspension of Pd(OH)$_2$ on carbon (20% (w/w) loading, 20 mg) in the same solvent mixture (0.5 mL). The suspension was purged with hydrogen, stirred under hydrogen atmosphere for 16 h, filtered and concentrated. Since the reaction had not proceeded to completion, the residue was subjected to the same conditions again and stirred for 24 h at room temperature. The mixture was filtered and concentrated, the residue was purified by solid phase extraction (Chromabond C18, Macherey-Nagel) and lyophilized to give pentasaccharide 55 (8.1 mg, 9.1 μmol, 88% over two steps) as a white solid. HRMS (MALDI) calcd. for C$_{32}$H$_{55}$NO$_{27}$ (M+Na)$^+$ 884.2883 found 884.2942 m/z. $^1$H NMR (400 MHz, D$_2$O) δ 5.48 (d, J=3.5 Hz, 1H), 5.02 (d, J=3.2 Hz, 1H), 4.88 (d, J=3.9 Hz, 1H), 4.51 (m, 2H), 4.20 (d, J=9.9 Hz, 1H), 4.04 (m, 1H), 4.02-3.52 (m, 26H), 3.43-3.19 (m, 4H).

Example 1-23

Synthesis of 4-O-benzoyl-2,3,6-tri-O-benzyl-α-D-glucopyranosyl-(1→4)-2,3,6-tri-O-benzyl-α-D-galactopyranosyl-(1→4)-methyl[2,3-di-O-benzoyl-β-D-glucopyranosyl]uronate-(1→4)-2,3-di-O-benzoyl-6-O-benzyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol 56)

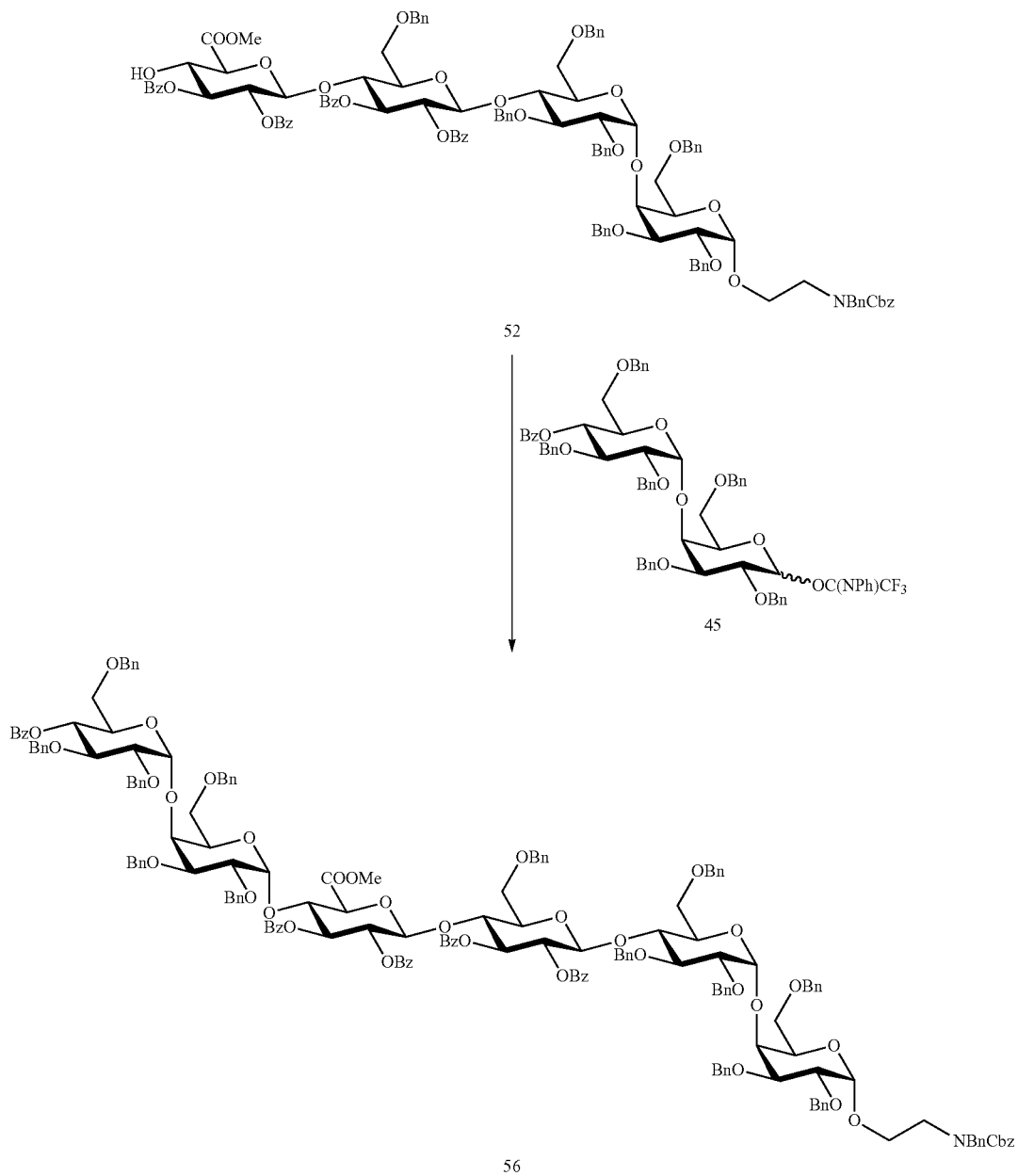

Alcohol 52 (50 mg, 25 μmol) and imidate 45 (72.1 mg, 62 μmol) were co-evaproated with dry toluene (3×10 mL) and kept under high vacuum for 30 min. The mixture was dissolved in Et₂O (2 mL) and CH₂Cl₂ (0.67 mL) and stirred over activated molecular sieves (3 Å-AW) for 30 min at room temperature. The solution was cooled to −20° C. and treated with TMSOTf (2 μL, 11 μmol). The mixture was stirred for 1 h and slowly warmed to 0° C. The reaction was quenched with sat. aq. NaHCO₃ (10 mL) and extracted with CH₂Cl₂ (4×10 mL). The combined organic fractions were dried over Na₂SO₄ and concentrated. The residue was purified by flash chromatography (EtOAc/hexanes 0:1 to 1:3 to 3:7 to 1:2) to give hexasaccharide 56 (51 mg, 17 µmol, 69%) as a clear oil. HRMS (MALDI) calcd. for $C_{180}H_{177}NO_{39}$ $(M+2Na)^{2+}$ 1511.0847 found 1511.0576 m/z.

Example 1-24

Synthesis of α-D-glucopyranosyl-(1→4)-α-D-galactopyranosyl-(1→4)-β-D-glucopyranosyluronate-(1→4)-β-D-glucoyranosyl-(1→4)-α-D-glucopyranosyl-(1→4)-α-D-galactopyranosyl-(1→1)-(2-amino) ethanol (57)

solution, respectively. The mixture was stirred for 16 h at room temperature and treated with NaOH (1 M aq. solution, 0.5 mL) and MeOH (0.5 mL). The reaction was stirred for 20 h at that temperature, quenched with 10% aq. $Na_2SO_3$ (0.8 mL) and concentrated under reduced pressure. The residue was dissolved in water (4 mL), neutralized with $NaHSO_4$ (0.5 M aq. solution) and extracted with EtOAc (4×10 mL). The combined organic fractions were dried over $Na_2SO_4$ and concentrated. The residue was treated with NaOMe (0.5 M solution in MeOH, 1 mL), warmed to 40° C. and stirred for 5 h at that temperature. The reaction was cooled to room temperature, stirred for another 16 h at that

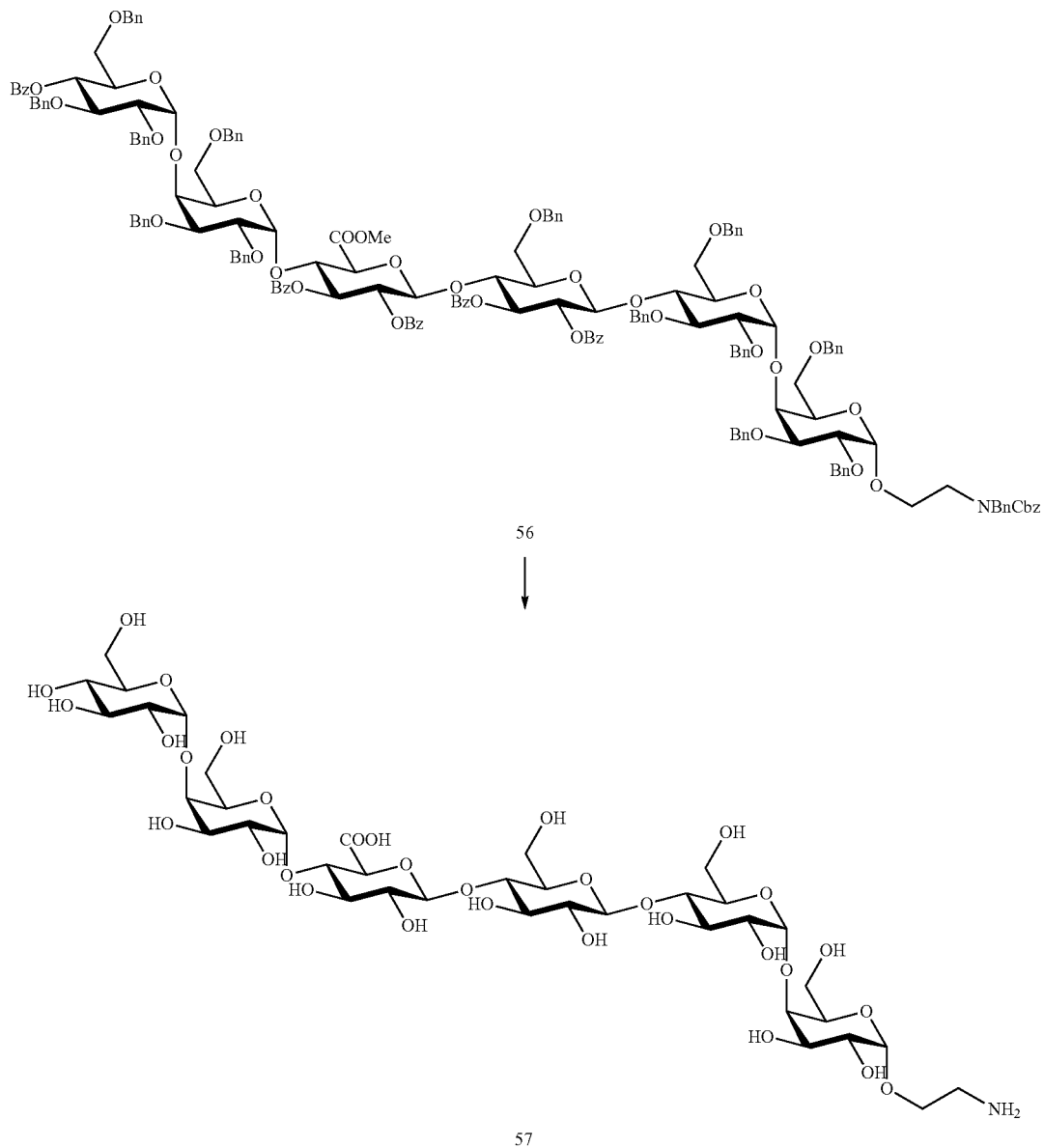

To a stirred solution of ester 56 (22 mg, 7.4 µmol) in THF (1 mL) and MeOH (1 mL) was added at 0° C. a 1:1 (v/v) mixture (296 µL) of hydrogen peroxide (6% (v/v) aq. solution, 295 µmol) and LiOH (0.5 M aq. solution, 74 µmol). The reaction was warmed to room temperature and treated after 2 h and 4 h with another 294 µL of the same LiOOH temperature and treated with water (0.5 mL). The mixture was neutralized with Amberlite IR-120 ($H^+$form), filtered and concentrated. The residue was purified by flash chromatography (EtOAc/hexanes 0:1:0 to 1:4+2% (v/v) AcOH to 1:1+2% (v/v) AcOH) to give the intermediate carboxylic acid as a clear oil.

The intermediate carboxylic acid in CH₂Cl₂/tBuOH/water (1.5:16:8, 3 mL) was purged with argon and treated at 0° C. with a suspension of Pd(OH)₂ on carbon (20% (w/w) loading, 30 mg) in the same solvent mixture (1 mL). The suspension was purged with hydrogen, stirred under hydrogen atmosphere for 18 h, filtered and concentrated. The residue was purified by solid phase extraction (Chromabond C18, Macherey-Nagel) and lyophilized to give hexasaccharide 57 (7 mg, 6.7 μmol, 86% over three steps) as a white solid. HRMS (ESI) calcd. for $C_{38}H_{65}NO_{32}$ (M+Na)⁺ 1070.3387 found 1070.3391 m/z.

Example 1-25

Synthesis of β-D-Glucopyranosyl-(1→4)β-D-glucoyranosyl-(1→4)-α-D-glucopyranosyl-(1→4)-α-D-galactopyranosyl-(1→1)-(2-amino)ethanol (60)

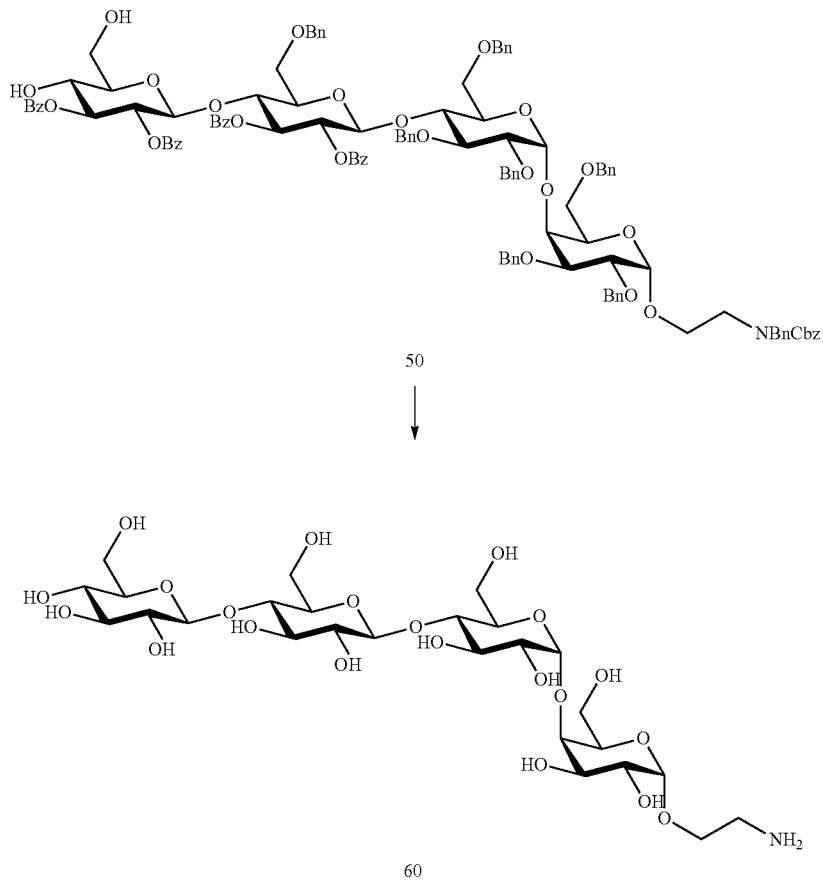

To a stirred solution of ester 50 (20 mg, 10.1 μmol) in THF (1 mL) and MeOH (0.33 mL) was added at room temperature NaOMe (0.5 M solution in MeOH, 0.5 mL). The reaction was warmed to 40° C. and stirred for 5 h at that temperature. The mixture was cooled to room temperature and stirred for 16 h at that temperature. The reaction was neutralized with Amberlite IR-120 (H⁺form), filtered and concentrated. The residue was purified by size exclusion chromatography (Sephadex LH-20, CH₂Cl₂/MeOH 2:1) to give the intermediate hexaol as a white foam.

The intermediate hexaol in CH₂Cl₂/tBuOH/water (1:16:8, 1 mL) was purged with argon and treated at 0° C. with a suspension of Pd(OH)₂ on carbon (20% (w/w) loading, 20 mg) in the same solvent mixture (1 mL). The suspension was purged with hydrogen, stirred under hydrogen atmosphere for 18 h, filtered and concentrated. The residue was purified by solid phase extraction (Chromabond C18, Macherey-Nagel) and lyophilized to give tetrasaccharide 60 (6.8 mg, 9.0 μmol, 89% over two steps) as a white solid. HRMS (ESI) calcd. for $C_{26}H_{47}NO_{21}$ (M+Na)⁺ 732.2538 found 732.2504 m/z.

Example 1-26

Synthesis of 2,3-di-O-benzoyl-β-D-glucoyranosyl-(1→4)-2,3,6-tri-O-benzyl-α-D-glucopyranosyl-(1→4)-2,3,6-tri-O-benzyl-α-D-galactopyranosyl-(1→1)-(2-N-benzyl-N-benzyloxycarbonylamino)ethanol (61)

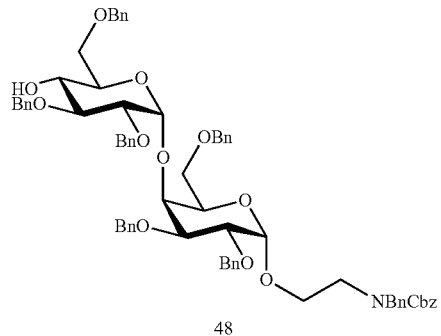
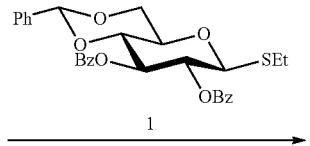
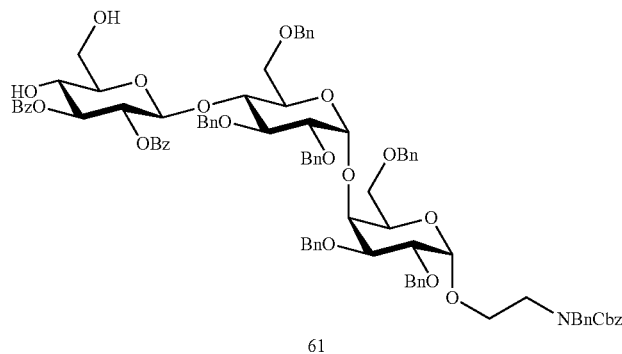

Alcohol 48 (15 mg, 13 μmol) and thioglycoside 1 (20.4 mg, 39 μmol) were co-evaporated with dry toluene (2×5 mL) and kept under high vacuum for 10 min. The mixture was dissolved in $CH_2Cl_2$ (1.3 mL) and stirred over activated molecular sieves (3 Å-AW) for 30 min at room temperature. The solution was cooled to −20° C. and treated with NIS (8.8 mg, 39 μmol) and TfOH (1 μL, 11 μmol). The mixture was stirred for 1 h at that temperature and slowly warmed to 0° C. The reaction was quenched with a 1:1 (v/v) mixture of sat. aq. $NaHCO_3$ (10 mL) and 10% (w/v) $Na_2SO_3$ (5 mL) and extracted with $CH_2Cl_2$ (4×10 mL). The combined organic extracts were dried over $Na_2SO_4$ and concentrated. The residue was purified by flash chromatography (EtOAc/hexanes 1:5 to 1:4 to 1:3) to give the intermediate benzylidene acetal as a yellow oil.

To a stirred solution of the intermediate benzylidene acetal in $CH_2Cl_2$ (2 mL) were added at room temperature ethanethiol (0.2 mL, 2.8 mmol) and p-toluenesulfonic acid (6 mg, 32 μmol). The mixture was stirred for 1 h at that temperature, quenched with $Et_3N$ (100 μL) and concentrated. The residue was purified by flash chromatography (EtOAc/hexanes 0:1 to 1:3 to 2:3) to give diol 61 (14.7 mg, 9.7 μmol, 75%) as a clear oil. HRMS (MALDI) calcd. for $C_{26}H_{47}NO_{21}$ $(M+Na)^+$ 1542.6188 found 1542.6145 m/z.

Example 1-27

Synthesis of β-D-Glucoyranosyl-(1→4)-α-D-glucopyranosyl-(1→4)-α-D-galactopyranosyl-(1→1)-(2-amino)ethanol (62)

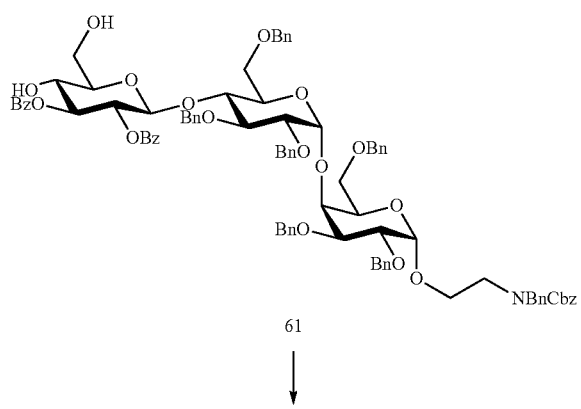

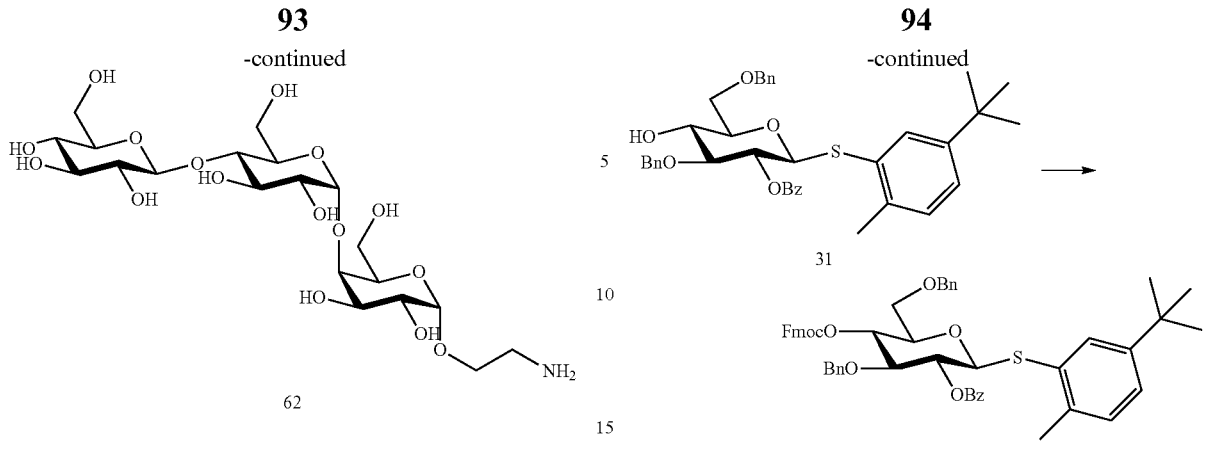

To a stirred solution of ester 61 (26 mg, 17 μmol) in CH₂Cl₂ (1 mL) and MeOH (1 mL) was added at room temperature NaOMe (0.5 M solution in MeOH, 0.5 mL). The reaction was stirred for 2 h at that temperature, neutralized at 0° C. with Amberlite IR-120 (H⁺ form), filtered and concentrated. The residue was purified by flash chromatography (EtOAc/hexanes 1:3 to 2:1) to give the intermediate tetraol as a white foam.

The intermediate tetraol in CH₂Cl₂/tBuOH/water (1:6:2, 5 mL) was purged with argon and treated at 0° C. with a suspension of Pd(OH)₂ on carbon (20% (w/w) loading, 30 mg) in the same solvent mixture (1 mL). The suspension was purged with hydrogen, stirred under hydrogen atmosphere for 24 h, filtered and concentrated. Since the reaction had not proceeded to completion, the residue was subjected to the same conditions again and stirred for 48 h at room temperature. The mixture was filtered and concentrated, the residue was purified by solid phase extraction (Chromabond C18, Macherey-Nagel) and lyophilized to give trisaccharide 62 (7.3 mg, 13 μmol, 79% over two steps) as a white solid. HRMS (ESI) calcd. for $C_{26}H_{47}NO_{21}$ (M+Na)⁺ 570.2010 found 570.2000 m/z.

Synthesis of Saccharide by Stepwise Automated Glycosylation

Example 1-28

Synthesis of Glucose Building Block 32

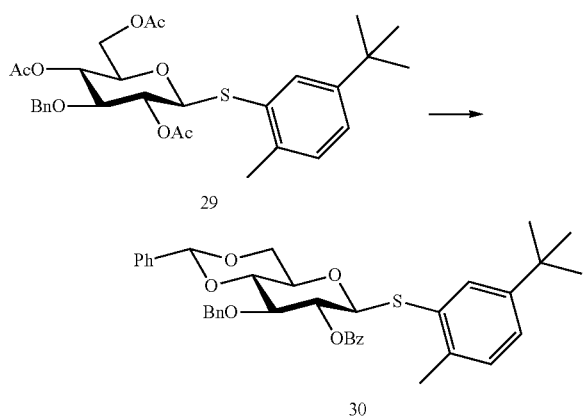

(2-Methyl-5-tert-butylphenyl) 2-O-benzoyl-3-O-benzyl-4,6-O-benzylidene-1-thio-β-D-glucopyranose (30)

(2-Methyl-5-tert-butylphenyl) 2,4,6-tri-O-acetyl-β-O-benzyl-1-thio-β-D glucopyranose (29) was dissolved in MeOH, NaOMe (1.0 eq) was added and the reaction mixture was stirred overnight. The mixture was neutralized with IR-120-H⁺ amberlite resin, filtered off, concentrated and co-evaporated with toluene. The crude triol was dissolved in DMF. Benzaldehyde dimethyl acetal (2.0 eq) and a catalytic amount of para-toluene sulfonic acid were added and the mixture was stirred at 80° C. for 2 h. After the mixture was cooled to room temperature, saturated aqueous NaHCO₃ was added. After phase separation, the organic phase was extracted three times with ethyl acetate. The combined organic layers were washed with brine, dried over MgSO₄, filtered and concentrated. The crude was dissolved in DCM, cooled to 0° C. and Bz₂O (2.0 eq), DMAP (0.5 eq) and triethylamine (4.0 eq) were added. After complete conversion, the reaction was quenched with saturated aqueous NaHCO₃ and the combined organic layers were washed with brine, dried over MgSO₄, filtered and concentrated. The residue was purified by flash column chromatography on silica gel to provide compound (88% over three steps). Rf: 0.25 (Hexane:EtOAc=9:1). [β]D=68.96 (c=3.18, CHCl₃).); IR (thin film, chloroform): u=2962, 1729, 1265, 1093 cm-1; 1H-NMR (400 MHz, CDCl₃) δ=8.01 (ddd, J=5.8, 5.3, 0.8 Hz, 2H, H Ar), 7.60 (ddd, J=7.1, 2.6, 1.3 Hz, 1H, H Ar), 7.51 (ddd, J=6.0, 5.6, 2.3 Hz, 3H, H Ar), 7.49-7.43 (m, 2H, H Ar), 7.43-7.35 (m, 3H, H Ar), 7.19 (dt, J=6.3, 3.1 Hz, 1H, H Ar), 7.13 (dd, J=6.7, 4.0 Hz, 3H, H Ar), 7.10-7.04 (m, 3H, H Ar), 5.63 (s, 1H CHO2Ph), 5.42-5.32 (m, 1H, H-2), 4.82 (d, J=11.9 Hz, 1H, CHHPh), 4.81 (d, J=10.2 Hz, 1H, H-1), 4.69 (d, J=12.0 Hz, 1H, CHHPh), 4.39 (dd, J=10.5, 5.0 Hz, 1H, H-6'), 3.94-3.86 (m, 3H, H-3, H-4, H-6), 3.56 (dt, J=14.6, 4.9 Hz, 1H, H-5), 2.19 (s, 3H), 1.27 (s, 9H). 13C-NMR (100 MHz, CDCl₃) δ 165.23 (C=O), 149.66, 137.84, 137.28, 137.03, 133.34, 132.37, 130.07, 130.04, 129.93, 129.90, 129.19, 128.51, 128.43, 128.29, 128.22, 127.71, 126.13, 125.38 (Ar), 101.44 (CHO₂Ph), 88.03 (C-1), 81.64 (C-3), 79.43 (C-4), 74.36 (CH2Ph), 72.25 (C-2), 70.66 (C-5), 68.81 (C-6), 34.56 (Cq tBu thio), 31.36 (tBu), 20.36 (CH3 thio); MS ESI+-HRMS m/z [M+Na]+calcd for $C_{38}H_{40}O_6SNa$ 647.2462, found 647.

(2-Methyl-5-tert-butylphenyl) 2-O-benzoyl-3,6-di-O-benzyl-1-thio-β-D-glucopyranose (31)

To a solution of compound 1 was co-evaporated with toluene, and dissolved in DCM (6.5 mL) under an argon atmosphere. Triethylsilane (0.62 mL, 3.88 mmol) and trifluoroacetic anhydride (0.27 mL, 1.94 mmol) were added and the solution was cooled to 0° C. Trifluoroacetic acid (0.30 mL, 3.88 mmol) were added dropwise, and the reaction was stirred and allowed to warm to room temperature. After complete conversion of the starting material, the solution was diluted with DCM, and quenched with saturated aqueous NaHCO$_3$. The combined organic layer was dried over MgSO$_4$ and the solvent was removed in vacuo. The residue was purified by column chromatography on silica gel (hexane/ethyl acetate, 9:1 to 7:3) to give a white foam (92%). MS ESI+-HRMS m/z [M+Na]+ calcd for C$_{38}$H$_{42}$O$_6$SNa 649.2600 found 649.2585.

(2-Methyl-5-tert-butylphenyl) 2-O-benzoyl-3,6-di-O-benzyl-4-O-fluorenylmethoxycarbonyl-1-thio-β-D-glucopyranoside (32)

Compound 31 was dissolved in DCM (6.5 mL) under an argon atmosphere. 9-fluorenylmethyl chloroformate (8.3 g, 31.9 mmol) and pyridine (3.44 mL, 42.5 mmol) were added into the solution at 0° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound
MS ESI+-HRMS m/z [M+Na]+ calcd for C$_{53}$H$_{52}$O$_8$SNa 871.3281 found 871.3311.

Example 1-29

Synthesis of Glucose Building Block 35

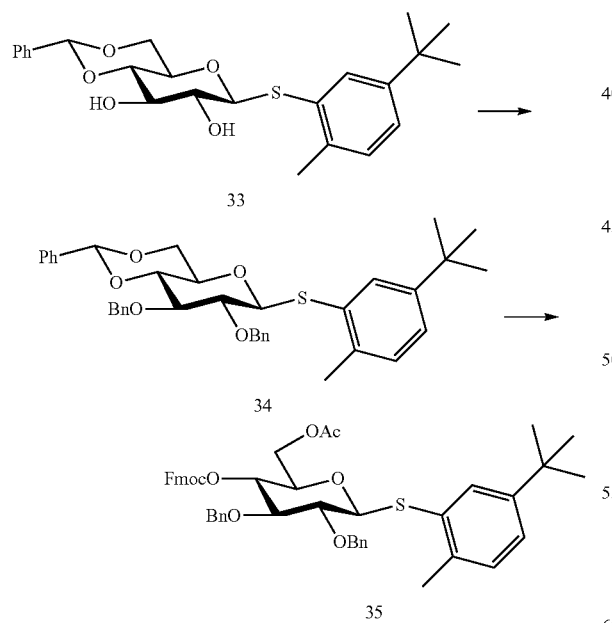

(2-Methyl-5-tert-butylphenyl) 2,3-di-O-benzyl-4,6-O-benzylidene-1-thio-β-D-glucopyranoside (34)

(2-Methyl-5-tert-butylphenyl) 4,6-O-benzylidene-1-thio-β-D-glucopyranoside (33) was dissolved in DCM (6.5 mL) under an argon atmosphere. Benzyl bromide, and NaH were added into the solution at 0° C. After complete conversion of the starting material, the reaction mixture was quenched with methanol, and diluted with ether, extracted with saturated NH$_4$Cl. The combined organic phase was dried over MgSO$_4$ and the solvent was removed in vacuo. The crude product was purified by silica gel flash column chromatography affording the title compound.
MS ESI+-HRMS m/z [M+Na]+ calcd for C$_{38}$H$_{42}$O$_5$SNa 633.2651 found 633.2644.

(2-Methyl-5-tert-butylphenyl) 6-O-acetyl-2,3-di-O-benzyl-4-O-fluorenylmethoxycarbonyl-1-thio-β-D-galactopyranoside (35)

To the solution of (2-Methyl-5-tert-butylphenyl) 2,3-di-O-benzyl-4,6-O-benzylidene-1-thio-β-D-glucopyranoside (34) in DCM (6.5 mL) were added TFA and water. After completion, the crude was decanted with hexane to remove byproduct. The crude was used to the next reaction. To the solution of the crude was added acetic acid, 2-chloro-1-methylpyridium iodide, and DABCO at −15° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound. The crude was dissolved in DCM (6.5 mL) under an argon atmosphere. 9-fluorenylmethyl chloroformate (8.3 g, 31.9 mmol) and pyridine (3.44 mL, 42.5 mmol) were added into the solution at 0° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound.
MS ESI+-HRMS m/z [M+Na]+ calcd for C$_{48}$H$_{50}$O$_8$SNa 809.3124 found 809.3137.

Example 1-30

Synthesis of (2-methyl-5-Cert-butylphenyl) 3,6-di-O-acetyl-2,4-di-O-benzyl-1-thio-β-D-galactopyranoside (37)

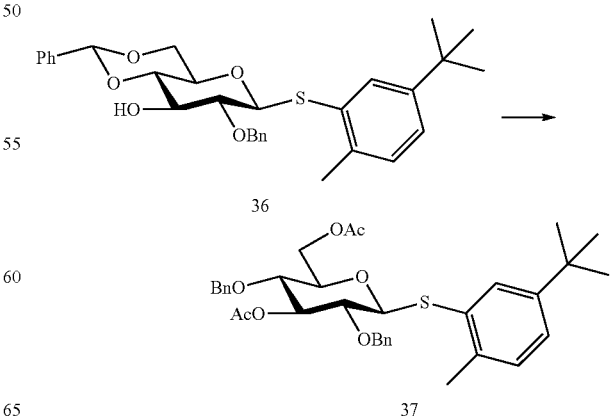

(2-Methyl-5-tert-butylphenyl)4,6-O-benzylidene-2-O-benzyl-1-thio-β-D-glucopyranoside (36) (*Tetrahedron Letter,* 1999, 40, 6523) was co-evaporated toluene and dissolved under an Ar atmosphere in DCM (170 mL). A 1 M solution of BH$_3$ in THF (108 mL, 108 mmol) was added and the solution was cooled to 0° C. After 10 min, trimethylsilyl triflate (1.66 mL, 9.2 mmol) was added and the reaction was stirred. After completion, the solution was diluted with DCM, and quenched with saturated aqueous NaHCO$_3$ dropwise. The organic phase was dried over MgSO$_4$ and the solvent was removed in vacuo. The crude product was used without further purification for the next step.

To a solution of the crude in DCM was added acetic anhydride (8.3 g, 31.9 mmol) and pyridine (3.44 mL, 42.5 mmol). After complete conversion of the starting material, the solution was diluted with DCM, extracted with saturated aqueous NaHCO$_3$. The combined organic phase was dried over MgSO$_4$ and the solvent was removed in vacuo. The crude product was purified by silica gel flash column chromatography affording the title compound (37).

MS ESI+-HRMS m/z [M+Na]+ calcd for C$_{35}$H$_{42}$O$_7$SNa 629.2546 found 629.2522.

Example 1-31

Synthesis of Protected Galactose Building Blocks

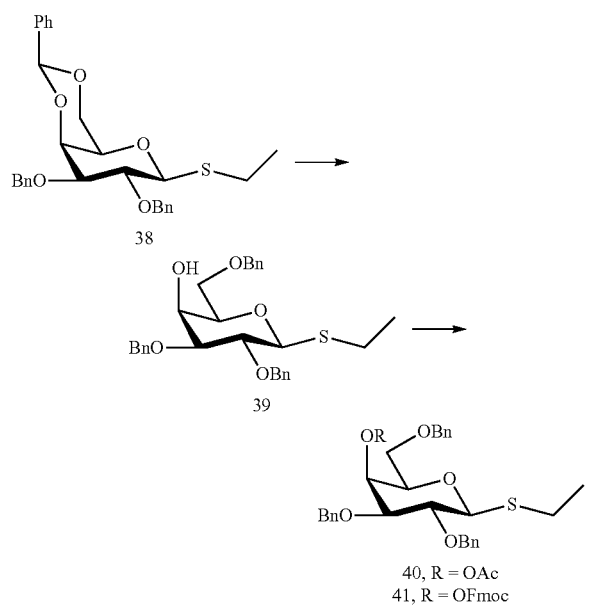

Ethyl 2,3-di-O-benzyl-4,6-O-benzylidene-1-thio-β-D-galactopyranoside (38) was co-evaporated with toluene, and dissolved in DCM (6.5 mL) under an Ar atmosphere. Triethylsilane (0.62 mL, 3.88 mmol) and trifluoroacetic anhydride (0.27 mL, 1.94 mmol) were added and the solution was cooled to 0° C. Trifluoroacetic acid (0.30 mL, 3.88 mmol) were added dropwise, and the reaction was stirred and allowed to warm to room temperature. After complete conversion of the starting material, the solution was diluted with DCM, and quenched with saturated aqueous NaHCO$_3$. The combined organic layer was dried over MgSO$_4$ and the solvent was removed in vacuo. The residue was purified by column chromatography on silica gel (hexane/ethyl acetate, 9:1 to 7:3) to give a white foam (94%). [Christopher E. Martin, Markus W. Weishaupt, and Peter H. Seeberger, *Chem. Commun.,* 2011, 47, 10260-10262.]

Ethyl 2,3,6-tri-O-benzyl-1-thio-β-D-galactopyranoside was dissolved in DCM (6.5 mL) under an argon atmosphere. Acetic anhydride (8.3 g, 31.9 mmol) and pyridine (3.44 mL, 42.5 mmol) were added into the solution at 0° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound (40). (*Chem. Commun.,* 2011, 47, 10260)

Ethyl 2,3,6-tri-O-benzyl-4-O-fluorenylmethoxycarbonyl-1-thio-β-D-galactopyranoside (41)

To a solution of compound 39 were added 9-fluorenylmethyl chloroformate (8.3 g, 31.9 mmol) and pyridine (3.44 mL, 42.5 mmol) at 0° C. After complete conversion of the starting material, the solution was diluted with DCM, extracted with 1 M aqueous HCl and saturated aqueous NaHCO$_3$. The combined organic phase was dried over MgSO$_4$ and the solvent was removed in vacuo. The crude product was purified by silica gel flash column chromatography affording the title compound. MS ESI-F-HRMS m/z [M+Na]+ calcd for C$_{44}$H$_{44}$O$_7$SNa 739.2705 found 739.2673.

Example 1-32

Preparation of Glucuronic Acid Building Block 42

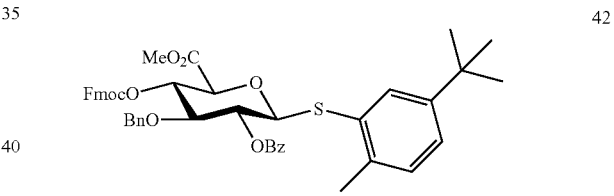

Methyl (2-methyl-5-tert-butyl-phenyl)-2-O-benzoyl-3-O-benzyl-4-O-fluorenylmethoxycarbonyl-1-thio-β-D-glucopyranosyluronate (42) was synthesized according to the procedure described in *Angew. Chem. Int. Ed.* 2013, 52, 5858.

Example 1-33

Synthesis of the Functionalized Solid Support

Functionalized resin was synthesized according to the procedure described in *Angew. Chem. Int. Ed.* 2013, 52, 5858.

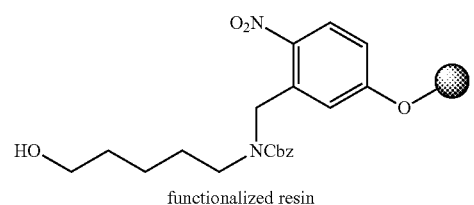 [SMILES: COc1ccc([N+](=O)[O-])c(CN(CCCCCO)C(=O)OCc2ccccc2)c1]

functionalized resin

Example 1-34

General Procedure 1: Automation Module

Preparation of Stock Solutions

Activator Solution: N-Iodosuccinimide (1.48 g, 6.66 mmol) and TfOH (60 µL, 0.66 mmol) was dissolved in a mixture of DCM (20 mL) and dioxane (20 mL).

Fmoc Deprotection Solution: A solution of 20% triethylamine in DMF (v/v) was prepared.

Thioglycoside Building Block Solution: 0.25 mmol of building block was dissolved in 2 ml of DCM.

Module 1: Glycosylation: The resin is swollen in 2 mL DCM and the temperature of the reaction vessel is adjusted to T1. For the glycosylation reaction, the DCM is drained and a solution of building block (5 eq in 1.0 mL DCM) is delivered to the reaction vessel. After the set temperature is reached, the reaction is started by the addition of activator (5 eq in 1.0 mL of solution). The glycosylation is performed for 5 min at temperature T1 and for 45 min at T2. This procedure is repeated twice. After the reaction was complete, the solution is drained and the resin is washed with DCM (six times each with 2 mL for 25 s). This procedure is repeated two times more.

Module 2: Fmoc Deprotection: The resin is washed with DMF (six time), swollen in 2 mL DMF and the temperature of the reaction vessel is adjusted to 25° C. For Fmoc deprotection the DMF is drained and 2 mL of a solution of 20% triethylamine in DMF is delivered to the reaction vessel. After 5 min the reaction solution is collected in the fraction collector of the oligosaccharide synthesizer and 2 mL of a solution of 20% triethylamine in DMF is delivered to the resin. This procedure is repeated three times. For the next glycosylation the resin is washed with DMF, THF, DCM (six times each). For Fmoc quantification the reaction solutions are combined and a 100 µL aliquot is taken. This aliquot is diluted with a solution of 20% triethylamine in DMF to 5 mL and the UV absorption at $\lambda=294$ nm is determined.

Cleavage from Solid Support (*Angew. Chem. Int. Ed.* 2013, 52, 5858-5861):

Continuous photocleavage flow reactor-general procedure: The flow reactor set-up consists of a medium pressure Hg lamp (Hanovia) with arc lengths of 27.9 cm and power of 450 W surrounded by a UV filter (Pyrex, 50% transmittance at 305 nm) in a quartz glass cooling system connected to a chiller to maintain a reaction temperature of 25° C. A fluorinated ethylene propylene (FEP) tubing (inner diameter: 0.03 inch; volume: 12 mL) is wrapped around the cooling system. A syringe pump is connected to the FEP tubing and is used to flush solvents and resin via the inlet through the reactor. The solid support is filtered off by a frit and the product solution is pooled and the solvents are removed in vacuo. The UV lamp is located in a box that is additionally cooled by a fan.

To finish the automated synthesis process, the resin is washed with DCM (six times), swollen in 2 mL DCM and transferred into a disposable syringe (20 mL). To prepare the photoreactor, the FEP tubing is washed with 15 mL MeOH, then subsequently with 15 mL DCM using a flow rate of 4 mL·min-1. For the cleavage, the resin is slowly injected from the disposable syringe (20 mL) into the reactor and pushed through the tubing with 15 mL DCM (flow rate: 500 µL·min-1). To wash out remaining resin, the tubing is washed with 20 mL DCM (flow rate: 500 µL·min-1). The suspension leaving the reactor is directed into a filter where the resin is filtered off and washed with DCM. The tubing is re-equilibrated with 15 mL DCM using a flow rate of 4 mL·min-1. The entire procedure is performed twice. The resulting solution is evaporated in vacuo and the crude product is purified by HPLC (column: Luna silica; flow rate: 5 mL·min-1).

General Procedure 2: Global Deprotection

To a solution of purified saccharide in a mixture of THF and MeOH (1.2 ml, v/v=4:1) were added 1 M LiOH-35% $H_2O_2$ (150 µL, v/v=2:1) at 0° C. The reaction was warmed up to room temperature, kept. After 4hr, 1M KOH (0.5 mL) was added and the mixture was stirred. After completion, the mixture was neutralized with IR-120-$H^+$ amberlite resin, filtered off, concentrated. The crude was dissolved in MeOH, ethyl acetate, and acetic acid (5 mL: 0.75 mL: 0.25 mL), followed by Pd/C (20mg). The mixture was bubbled under an atmosphere of argon for 30 min, then at atmosphere of $H_2$ for 12 hr, filtered and concentrated. The residue was purified by HPLC (Hyper-carbon) and lyophilized to give saccharide (formic acid salt) as a white solid.

General Procedure to Run Automation:

The functionalized resin of Example 1-33 (65 mg; loading 0.385 mmol/g; 0.025 mmol) was loaded into the reaction vessel of the synthesizer and swollen in 2 mL DCM. To start the synthesis sequence, the resin was washed consecutively with DMF, THF, then DCM (three times each with 2 mL for 25 s). Module 1 for each building block and module 2 for Fmoc deprotection were performed to produce each saccharide structure.

Purification on HPLC

After synthesis of the desired compound, the resin was cleaved from the solid support. The crude product was purified by semi-preparative HPLC (column: Luna-Silica (21×250 mm; 5 µm); flow rate: 5 mL/min; eluents: Hexane/Ethyl acetate; gradient: 20% (5 min) →60% (in 45 min) →100% (in 5 min); detection: 210 and 280 nm) affording the target oligosaccharide.

After global deprotection of the desired compound, the crude product was purified by semi-preparative HPLC (column: Luna-Hyper-Carbon (21×250 mm; 5 µm); flow rate: 5 mL/min; eluents: 0.1% formic acid in Water/0.1% formic acid in acetonitrile; gradient: 10% (5 min)→40% (in 30 min)→100% (in 5 min); detection: ELSD) affording the target oligosaccharide.

Example 1-34

Synthesis of N-benzyloxycarbonyl-5-amino-pentanyl methyl 2-O-benzoyl-3-O-benzyl-β-D-glucopyranosyluronate-(1→4)-2-O-benzoyl-3,6-di-O-benzyl-β-D-glucopyranosyl-(1→4)-6-O-acetyl-2,3-di-O-benzyl-α-D-glucopyranosyl-(1→4)-2,3,6-tri-O-benzyl-α-D-galactopyranoside (19a)

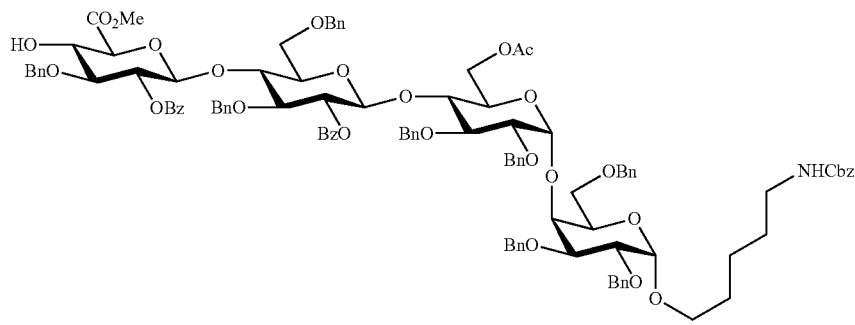

Tetrasaccharide 21a was prepared according to the reactions sequence:

| Sequence | Module | Details | Condition |
|---|---|---|---|
| I | 1 | Building block 41 | T1 = −30° C., T2 = −10° C. |
|  | 2 | Fmoc Removal | r.t for 5 min |
| II | 1 | Building block 35 | T1 = −30° C., T2 = 0° C. |
|  | 2 | Fmoc Removal | r.t for 5 min |
| III | 1 | Building block 32 | T1 = −40° C., T2 = −20° C. |
|  | 2 | Fmoc Removal | r.t for 5 min |
| IV | 1 | Building block 42 | T1 = −30° C., T2 = 0° C. |
|  | 2 | Fmoc Removal | r.t for 5 min |

8% from the resin, MS ESI+-HRMS m/z [M+Na]+ calcd for $C_{110}H_{117}NO_{27}Na$ 1906.7711, found 1906.7590.

Example 1-35

Preparation of 5-amino pentanyl β-D-glucopyranosyl uronic acid-(1→4)-β-D-glucopyranosyl-(1→4)-α-D-glucopyranosyl-(1→4)-α-D-galactopyranoside (19)

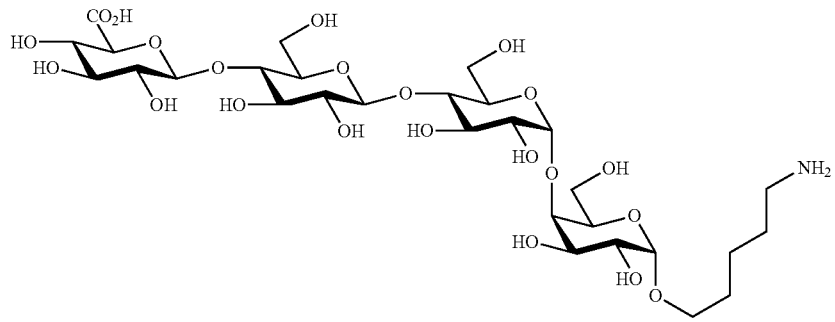

Tetrasaccharide 19a was subjected to the general deprotection procedure to afford tetrasaccharide 19: 36%; MS ESI+-HRMS m/z [M+H]+ calcd for $C_{29}H_{52}NO_{22}$ 766.2975, found 766.2988.

Example 1-36

Synthesis of N-benzyloxycarbonyl-5-amino-pentanyl 4-O-acetyl-2,3,6-tri-O-benzyl-α-D-galactopyranosyl-(1→4)-methyl 2-O-benzoyl-3-O-benzyl-β-D-glucopyranosyluronate-(1→4)-2-O-benzoyl-3,6-di-O-benzyl-β-D-glucopyranosyl-(1→4)-6-O-acetyl-2,3-di-O-benzyl-α-D-glucopyranoside (20a)

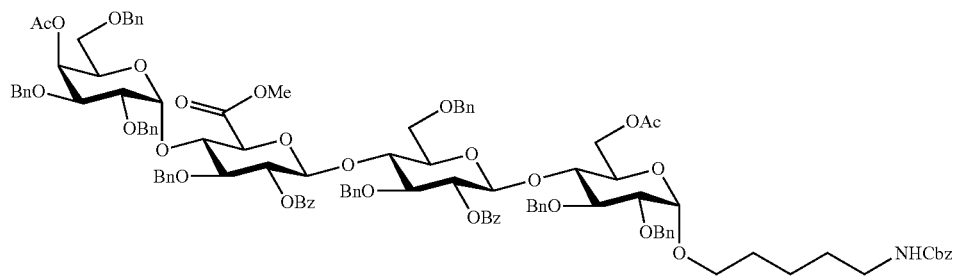

Tetrasaccharide 20a was prepared according to the following reactions sequence:

| Sequence | Module | Details | Condition |
|---|---|---|---|
| I | 1 | Building block 35 | T1 = −30° C., T2 = 0° C. |
|  | 2 | Fmoc Removal | r.t for 5 min |
| II | 1 | Building block 32 | T1 = −30° C., T2 = −10° C. |
|  | 2 | Fmoc Removal | r.t for 5 min |
| III | 1 | Building block 42 | T1 = −30° C., T2 = 0° C. |
|  | 2 | Fmoc Removal | r.t for 5 min |
| IV | 1 | Building block 40 | T1 = −40° C., T2 = −20° C. |
|  | 2 | Fmoc Removal | r.t for 5 min |

16% from the resin, MS ESI+-HRMS m/z [M+Na]$^+$ calcd for $C_{112}H_{119}NO_{28}Na$ 1948.7816, found 1948.7796.

Example 1-37

Preparation of 5-amino pentanyl α-D-galactopyranosyl-(1→4)-β-D-glucopyranosyluronic acid-(1→4)-β-D-glucopyranosyl-(1→4)-α-D-glucopyranoside (20)

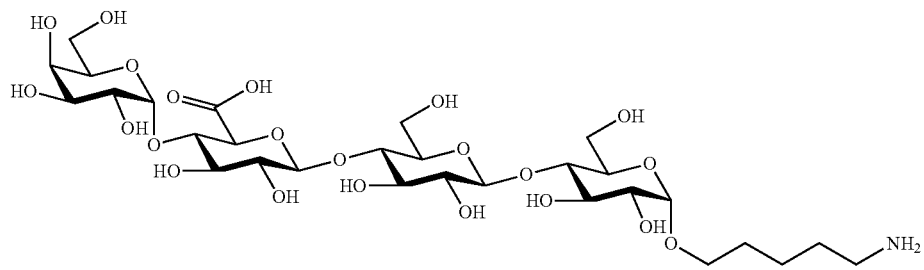

Tetrasaccharide 20a was subjected to the general deprotection procedure to afford tetrasaccharide 20: 40% MS ESI+-HRMS m/z [M+H]+ calcd for $C_{29}H_{52}NO_{22}$ 766.2975, found 766.2964.

Example 1-38

Preparation of N-benzyloxycarbonyl-5-amino-pentanyl 3,6-di-O-acetyl-2,4-di-O-benzyl-α-D-glucopyranosyl-(1→4)-2,3,6-tri-O-benzyl-α-D-galactopyranosyl-(1→4)-methyl 2-O-benzoyl-3-O-benzyl-β-D-glucopyranosyluronate-(1→4)-2-O-benzoyl-3,6-di-O-benzyl-β-D-glucopyranoside (21a):

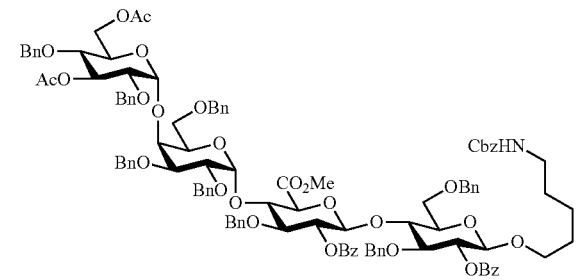

| Sequence | Module | Details | Condition |
|---|---|---|---|
| I | 1 | Building block 32 | T1 = −30° C., T2 = −10° C. |
| | 2 | Fmoc Removal | r.t for 5 min |
| II | 1 | Building block 42 | T1 = −30° C., T2 = 0° C. |
| | 2 | Fmoc Removal | r.t for 5 min |
| III | 1 | Building block 41 | T1 = −40° C., T2 = −20° C. |
| | 2 | Fmoc Removal | r.t for 5 min |
| IV | 1 | Building block 37 | T1 = −30° C., T2 = 0° C. |
| | 2 | Fmoc Removal | r.t for 5 min |

20% from the resin, MS ESI+-HRMS m/z [M+Na]+ calcd for $C_{112}H_{119}NO_{25}Na$ 1948.7816, found 1950.7906

Example 1-39

Preparation of 5-Amino pentanyl α-D-glucopyranosyl-(1→4)-α-D-galactopyranosyl-(1→4)-β-D-glucopyranosyluronic acid-(1→4)-β-D-glucopyranoside (21)

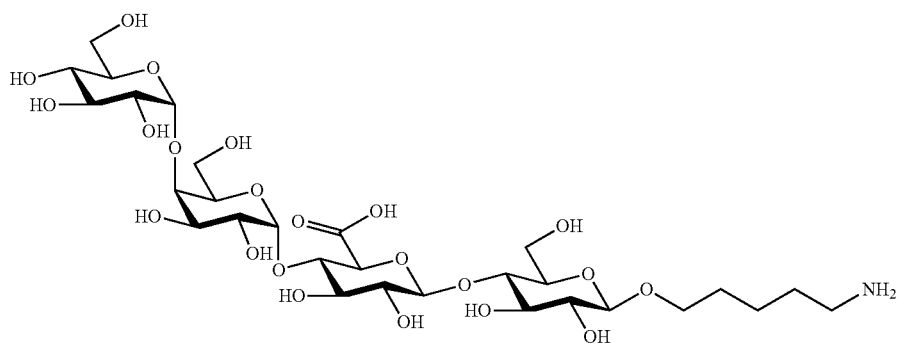

Tetrasaccharide 21a was subjected to the general deprotection procedure to afford tetrasaccharide 21: 42% MS ESI+-HRMS m/z [M+H]+ calcd for $C_{29}H_{52}NO_{22}$ 766.2975, found 766.2977.

Example 1-40

Synthesis of N-benzyloxycarbonyl-5-amino-pentanyl 2-O-benzoyl-3,6-di-O-benzyl-β-D-glucopyranosyl-(1→4)-6-O-acetyl-3,4-di-O-benzyl-α-D-glucopyranosyl-(1→4)-2,3,6-tri-O-benzyl-α-D-galactopyranosyl-(1→4)-methyl 2-O-benzoyl-3-O-benzyl-β-D-glucopyranosyl uronate (22a)

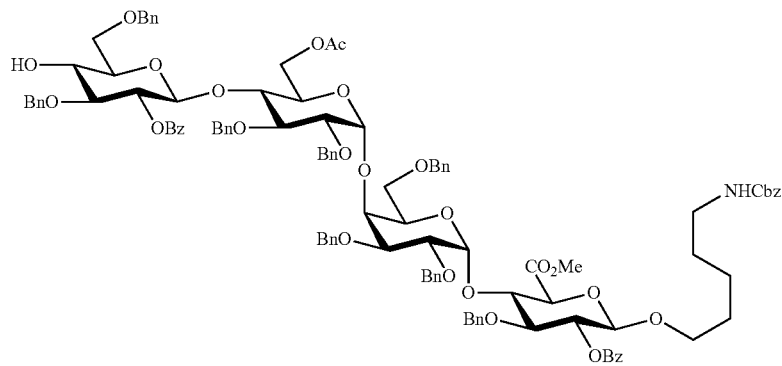

Tetrasaccharide 22a was synthesized according to the following reactions sequence:

| Sequence | Module | Details | Condition |
|---|---|---|---|
| I | 1 | Building block 42 | T1 = −30° C., T2 = 0° C. |
|  | 2 | Fmoc Removal | r.t for 5 min |
| II | 1 | Building block 41 | T1 = −40° C., T2 = −20° C. |
|  | 2 | Fmoc Removal | r.t for 5 min |
| III | 1 | Building block 35 | T1 = −30° C., T2 = 0° C. |
|  | 2 | Fmoc Removal | r.t for 5 min |
| IV | 1 | Building block 32 | T1 = −30° C., T2 = −10° C. |
|  | 2 | Fmoc Removal | r.t for 5 min |

21% from the resin, MS ESI+-HRMS m/z [M+Na]+ calcd for $C_{110}N_{117}NO_{27}Na$ 1906.7711, found 1906.7624.

Example 1-41

Synthesis of 5-amino pentanyl 13-D-glucopyranosyl-(1→4)-α-D-glucopyranosyl-(1→4)-α-D-galactopyranosyl-(1→4)-β-D-glucopyranosyl uronic acid (22)

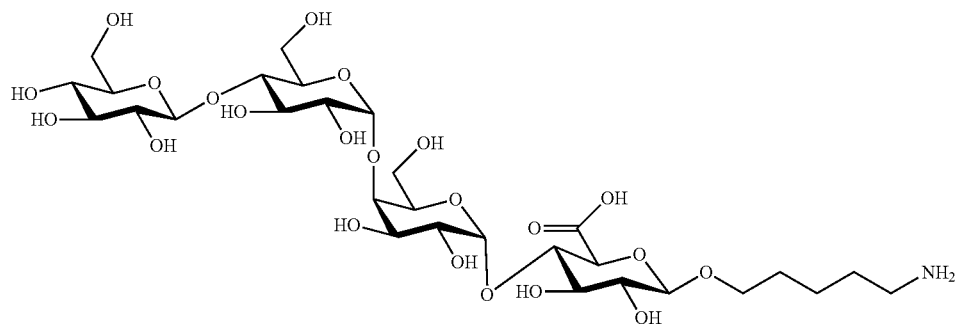

Tetrasaccharide 22a was subjected to the general deprotection procedure to afford tetrasaccharide 22: 52% MS ESI+-HRMS m/z [M+H]+ calcd for $C_{29}H_{52}NO_{22}$ 766.2975, found 766.2988.

Further examples of inventive saccharides according to the procedures described in Examples 1-28 to 1-34

63

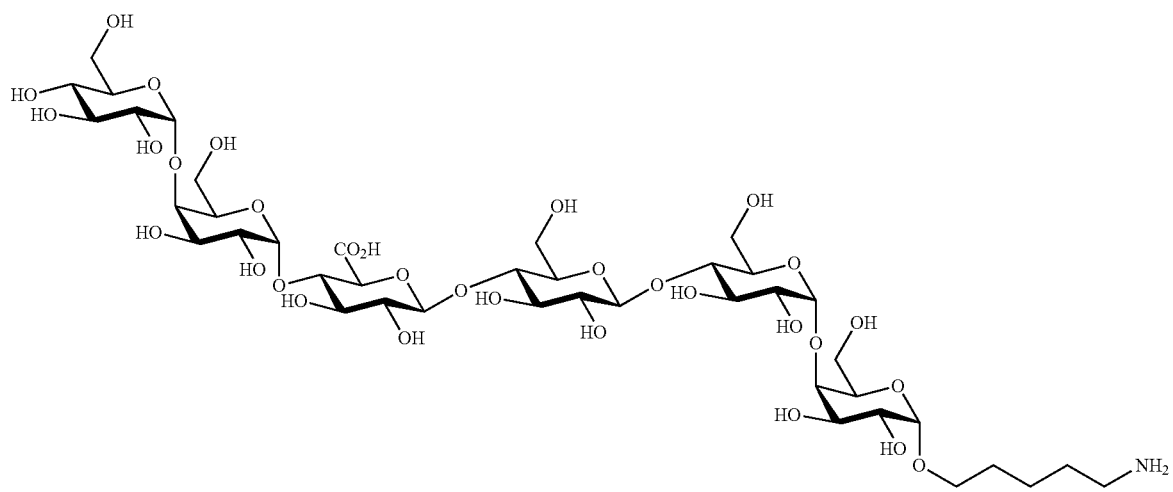

MS ESI+-HRMS m/z [M+H]+ calcd for: $C_{41}Fl_{71}NO_{32}$ 1090.3959;

5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranosyl-(1→4-α-D-galactopyranoside;

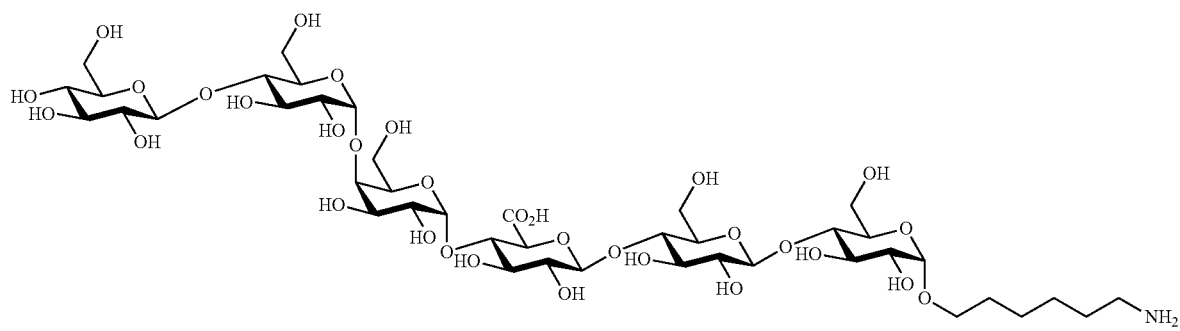

64

MS ESI+-HRMS m/z [M+H]$^+$ calcd for: $C_{42}H_{73}NO_{32}$ 1104.4116;

5-amino pentanyl galactopyranosyl-(1→4)-α-D-glucopyranosyl-(1→4)-α-D-galactopyranosyl-(1→4)-β-D-glucopyranosyluronic acid-(1→4)-β-D-glucopyranosyl-(1→4)-α-D-glucopyranoside;

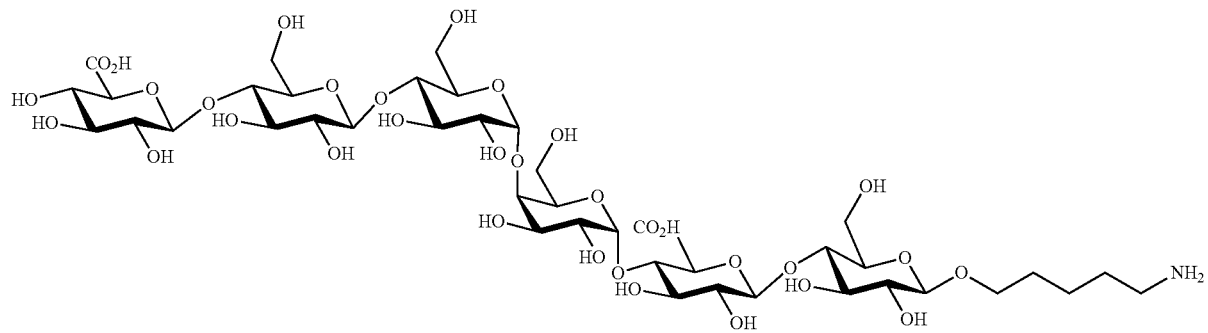

65

MS ESI+-HRMS m/z [M+H]$^+$ calcd for: $C_{41}H_{69}NO_{33}$ 1104.3752;

5-amino pentanyl β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid-(1→4)- β-D-glucopyranoside;

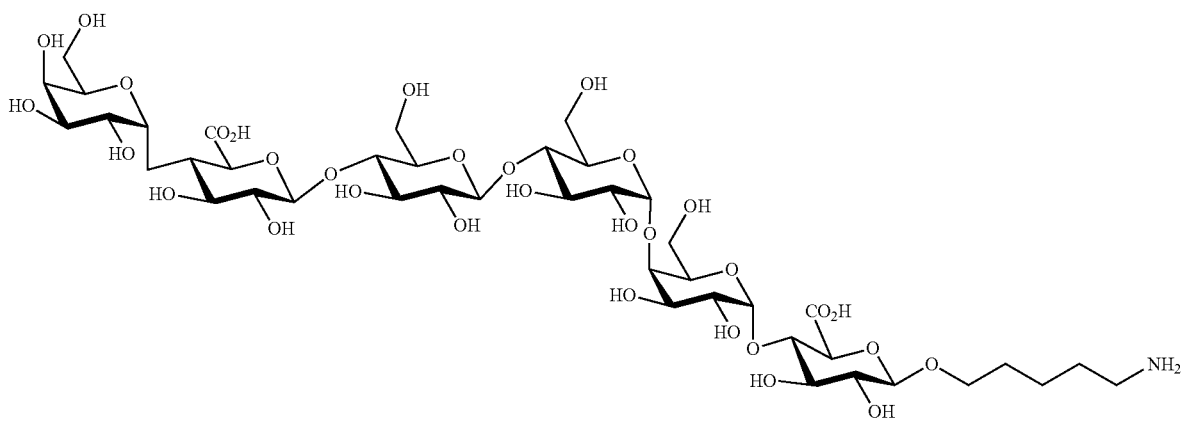

66

MS ESI+-HRMS m/z [M+H]$^+$ calcd for: $C_{41}H_{69}NO_{33}$ 1104.3752;

5-amino pentanyl α-D-galactopyranosyl-(1→4)-β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid;

67

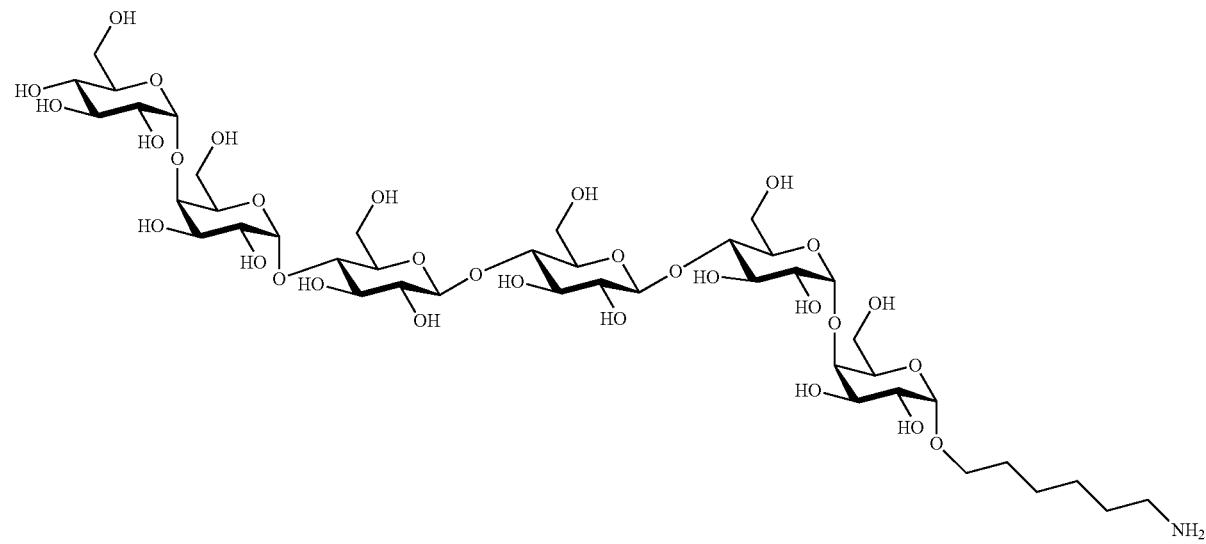

MS ESI+-HRMS m/z [M+H]+ calcd for: $C_{42}H_{75}NO_{31}$ 1090.4323;

5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranosyl-(1→4-α-D-galactopyranoside;

68

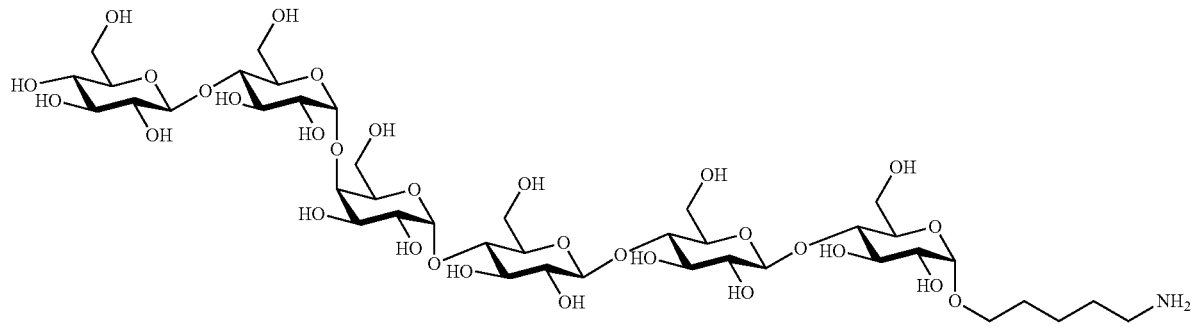

MS ESI+-HRMS m/z [M+H]$^+$ calcd for: $C_{41}H_{73}NO_{31}$ 1076,4167.

5-amino pentanyl β-D-glucopyranosyl-(1→4)-α-D-glucopyranosyl-(1→4)-α-D-galactopyranosyl-(1→4)-β-D-glucopyranosyl-(1→4)-β-D-glucopyranosyl-(1→4)-α-D-glucopyranoside

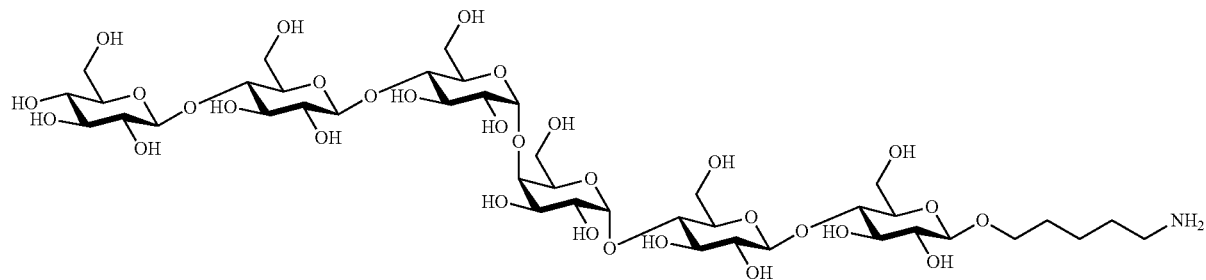

69

MS ESI+-HRMS m/z [M+H]$^+$ calcd for: $C_{41}H_{73}NO_{31}$ 1076.4167.

5-amino pentanyl β-D-glucopyranosyl-(1→4)-β-D-glucopyranosyl-(1→4)-α-D-glucopyranosyl-(1→4)-α-D-galactopyranosyl-(1→4)-β-D-glucopyranosyl-(1→4)-β-D-glucopyranoside;

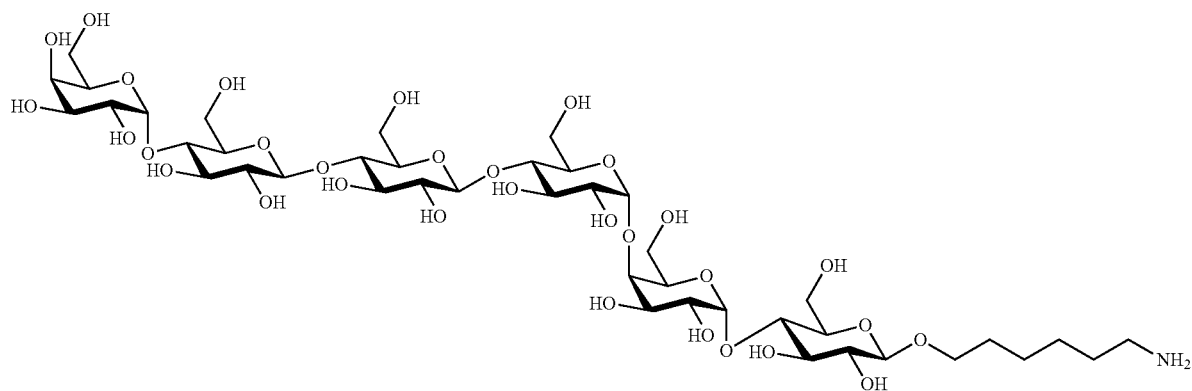

70

MS ESI+-HRMS m/z [M+H]$^+$ calcd for: $C_{42}H_{75}NO_{31}$ 1090.4323;

5-amino pentanyl α-D-galactopyranosyl-(1→4)-β-D-glucopyranosyl-(1-4)-β-D-glucopyranosyl-(1→4)-α-D-glucopyranosyl-(1→4)-α-D-galactopyranosyl-(1→4)-β-D-glucopyranoside (70);

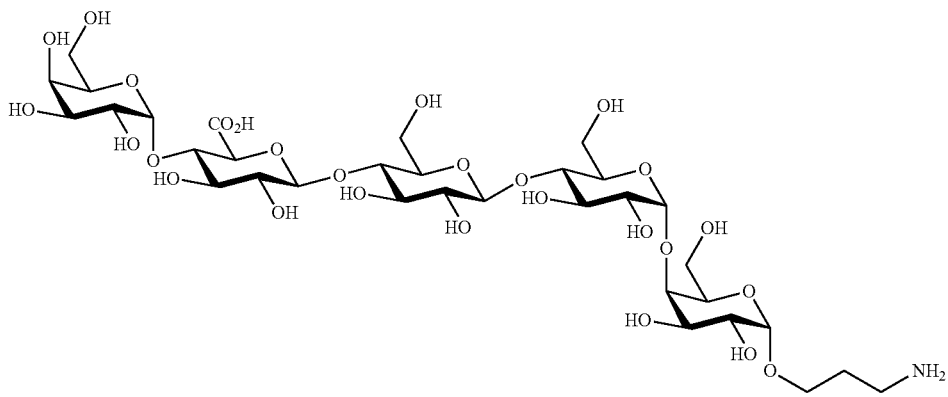

71

MS ESI+-HRMS m/z [M+H]+ calcd for: $C_{33}H_{57}NO_{27}$ 890.3118;

3-aminopropyl α-D-galactopyranosyl-(1→4)-β-D-glucopyranosyluronic acid-(1→4)-β-D-glucopyranosyl-(1→4)-α-D-glucopyranosyl-(1→4)-α-D-galactopyranoside;

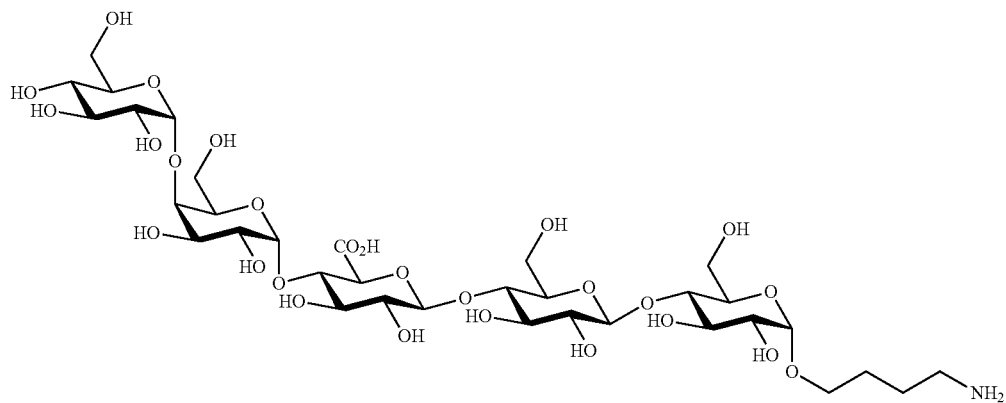

72

MS ESI+-HRMS m/z [M+H]+ calcd for: $C_{34}H_{59}NO_{27}$ 914.3274;

5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranoside;

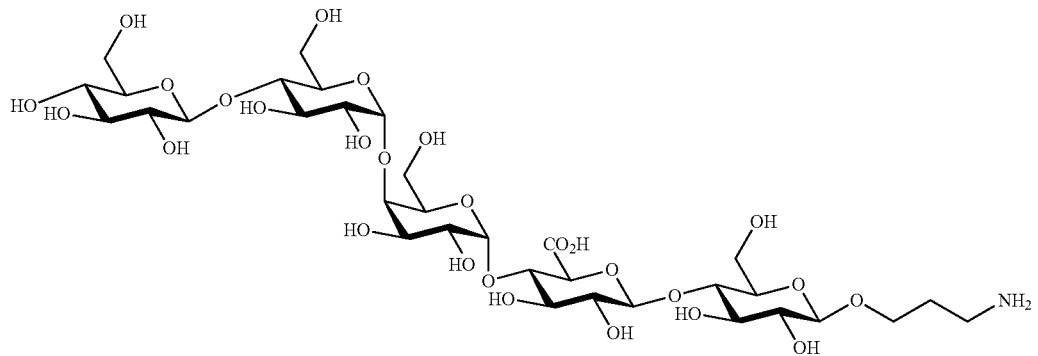

73

MS ESI+-HRMS m/z [M+H]+ calcd for: $C_{33}H_{57}NO_{27}$ 890.3118;

3-aminopropyl β-D-glucopyranosyl-(1→4)-α-D-glucopyranosyl-(1→4)-α-D-galactopyranosyl-(1→4)-β-D-glucopyranosyluronic acid-(1→4)-β-D-glucopyranoside;

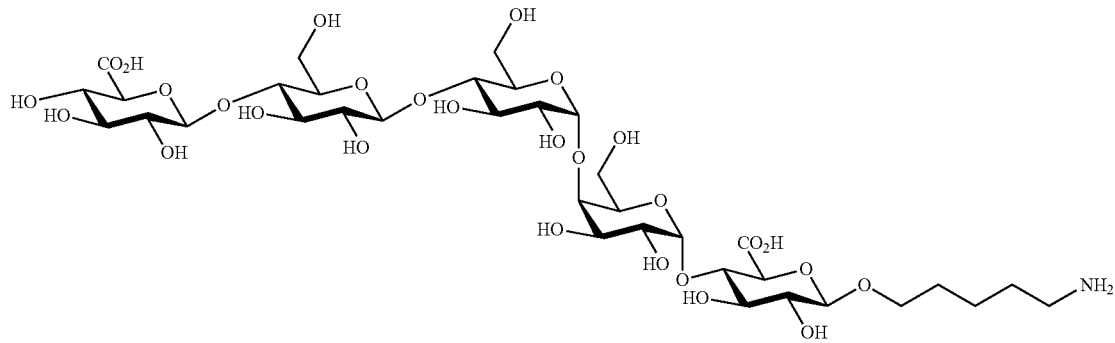

74

MS ESI+-HRMS m/z [M+H]+ calcd for: $C_{35}H_{59}NO_{28}$ 942.3224;

5-amino pentanyl β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid;

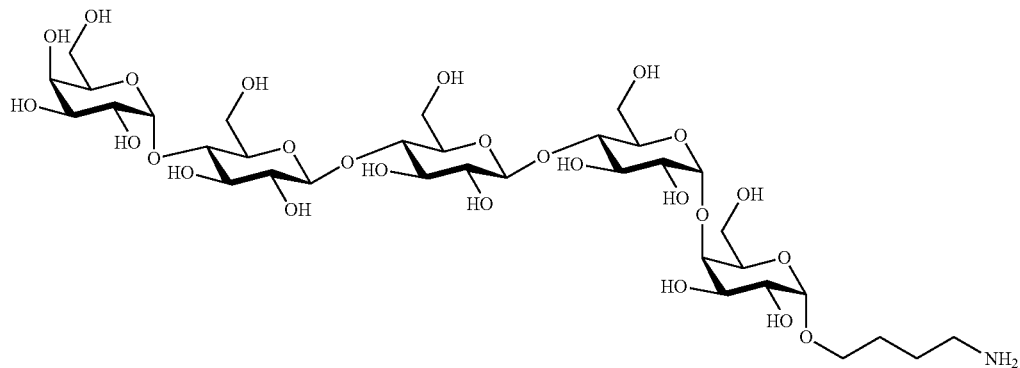

75

MS ESI+-HRMS m/z [M+H]+ calcd for: $C_{34}H_{61}NO_{26}$ 890.3482;

4-aminobutyl α-D-galactopyranosyl-(1→4)-β-D-glucopyranosyl-(1→4)-β-D-glucopyranosyl-(1→4)- α-D-glucopyranosyl-(1→4-α-D-galactopyranoside;

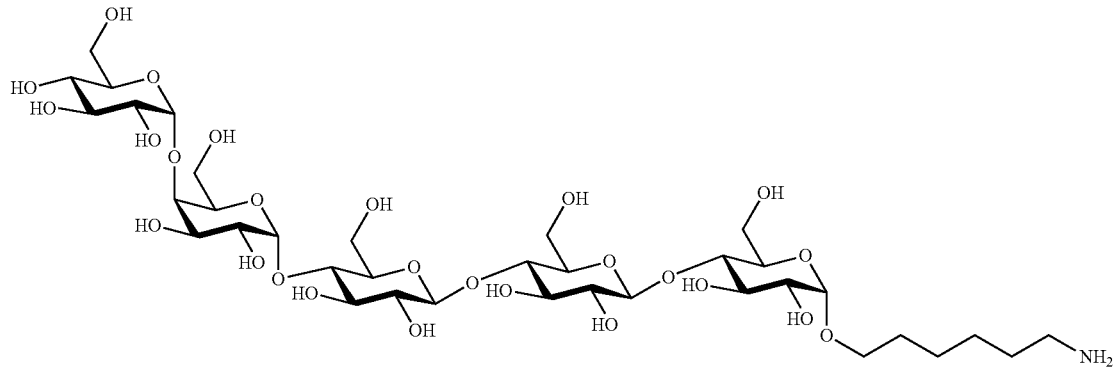

76

MS ESI+-HRMS m/z [M+H]+ calcd for: $C_{36}H_{65}NO_{26}$ 928.3795;

6-amino hexanyl α-D-glucopyranosyl-(1→4)-α-D-galactopyranosyl-(1→4)-β-D-glucopyranosyl-(1→4)-β-D-glucopyranosyl-(1→4)-α-D-glucopyranoside;

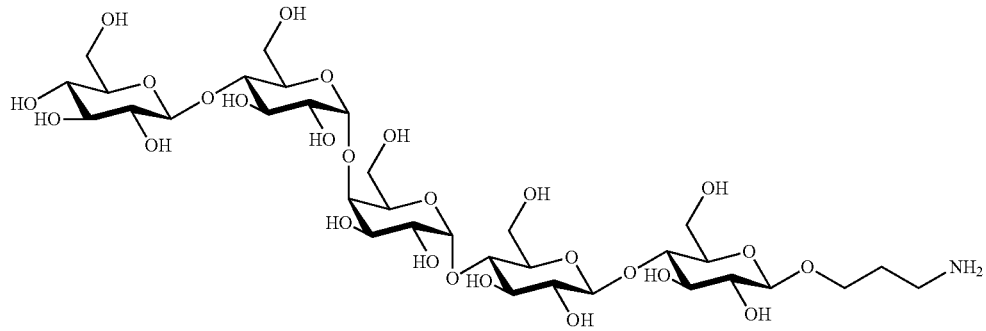

77

MS ESI+-HRMS m/z [M+H]+ calcd for: $C_{33}H_{59}NO_{26}$ 886.3325;

3-aminopropyl β-D-glucopyranosyl-(1→4)-α-D-glucopyranosyl-(1→4)-α-D-galactopyranosyl-(1→4)-β-D-glucopyranosyl-(1→4)-β-D-glucopyranoside;

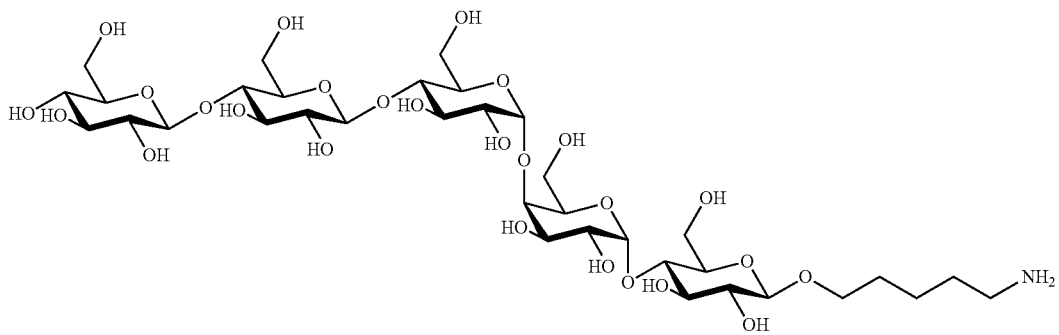

78

MS ESI+-HRMS m/z [M+H]+ calcd for: $C_{35}H_{63}NO_{26}$ 914.3638;

5-amino pentanyl β-D-glucopyranosyl-(1→4)-β-D-glucopyranosyl-(1→4)-α-D-glucopyranosyl-(1→4)-α-D-galactopyranosyl-(1→4)-β-D-glucopyranoside;

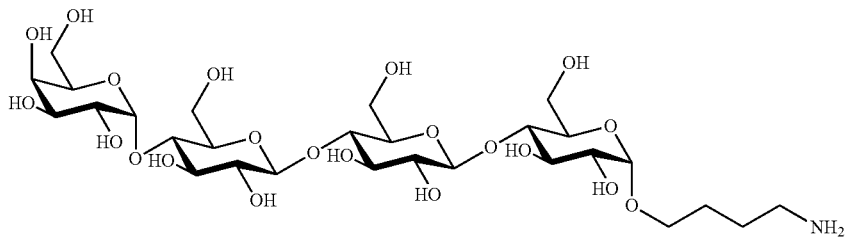

79

MS ESI+-HRMS m/z [M+H]+ calcd for: $C_{28}H_{51}NO_{21}$ 738.2954;

4-aminobutyl α-D-galactopyranosyl-(1→4)-β-D-glucopyranosyl-(1→4)-β-D-glucopyranosyl-(1→4)-α-D-glucopyranoside;

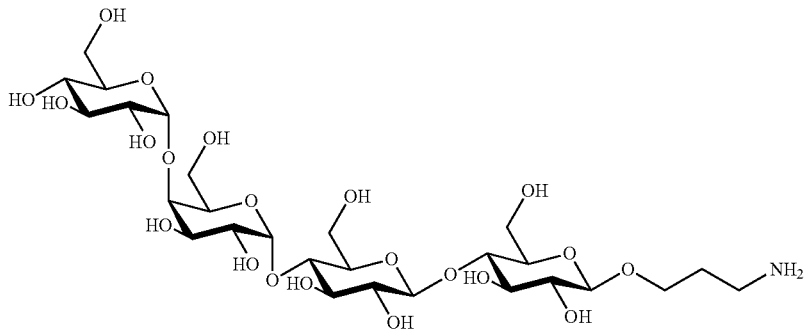

80

MS ESI+-HRMS m/z [M+H]+ calcd for: $C_{27}H_{49}NO_{21}$ 724.2797;

3-aminopropyl α-D-glucopyranosyl-(1→4)-α-D-galactopyranosyl-(1→4)-β-D-glucopyranosyl-(1→4)-β-D-glucopyranoside;

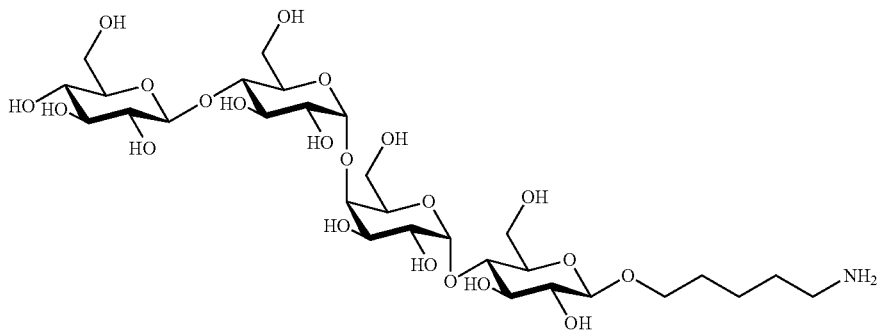
81
MS ESI+-HRMS m/z [M+H]+ calcd for: $C_{29}H_{53}NO_{21}$ 752.3110;
6-amino hexanyl β-D-glucopyranosyl-(1→4)-α-D-glucopyranosyl-(1→4)-α-D-galactopyranosyl-(1→4)-β-D-glucopyranoside;
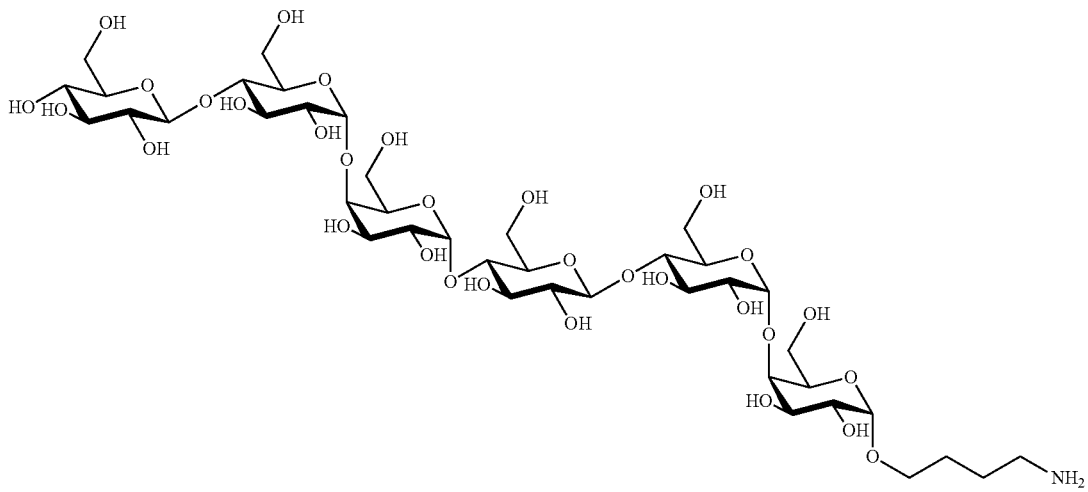
82
MS ESI+-HRMS m/z [M+H]+ calcd for: $C_{40}1-1_{71}NO_{31}$ 1062.4010;
4-amino butyl β-D-glucopyranosyl-(1→4)-α-D-glucopyranosyl-(1→4)-α-D-galactopyranosyl-(1→4)-β-D-glucopyranosyl -(1→4)-α-D-glucopyranosyl-(1→4)-α-D-galactopyranoside;
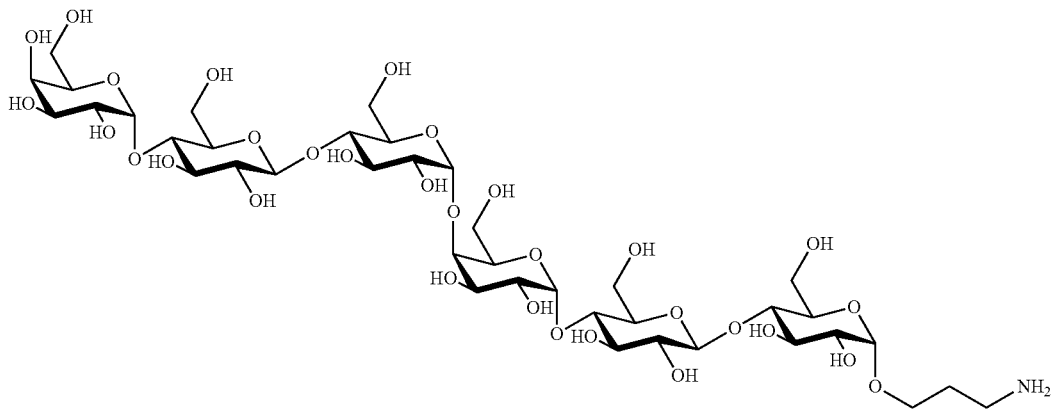
83

MS ESI+-HRMS m/z [M+H]+ calcd for: $C_{39}H_{69}NO_{31}$ 1048.3854;

3-aminopropyl α-D-galactopyranosyl-(1→4)-β-D-glucopyranosyl-(1→4)-α-D-glucopyranosyl-(1→4)-α-D-galactopyranosyl-(1→4)-β-D-glucopyranosyl-(1→4)-α-D-glucopyranoside;

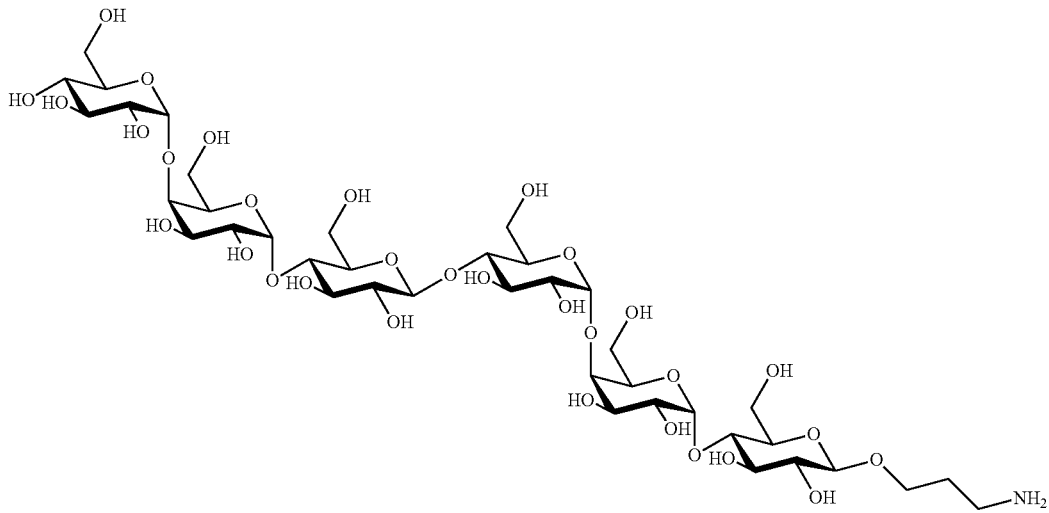

84

MS ESI+-HRMS m/z [M+H]+ calcd for: $C_{39}H_{69}NO_{31}$ 1048.3854;

3-aminopropyl α-D-glucopyranosyl-(1→4)-α-D-galactopyranosyl-(1→4)-α-D-glucopyranosyl-(1→4)-α-D-glucopyranosyl-(1→4)-α-D-galactopyranosyl-(1→4)-β-D-glucopyranoside;

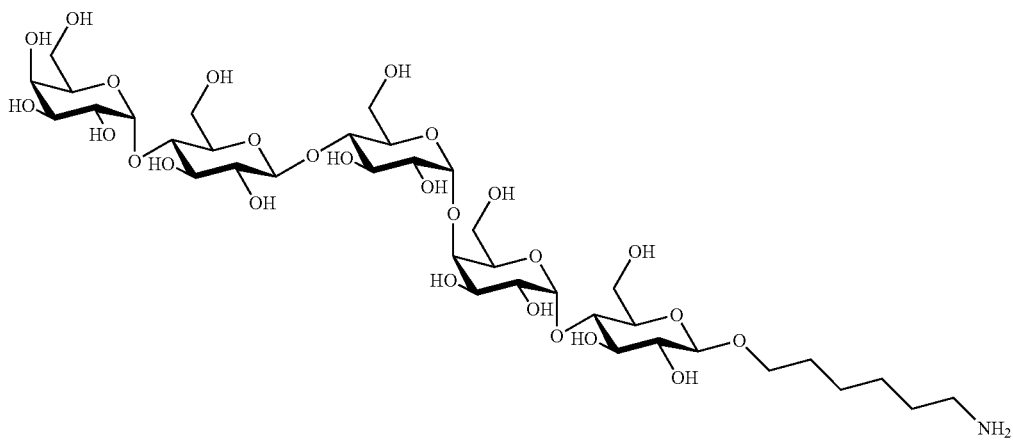

85

MS ESI+-HRMS m/z [M+H]+ calcd for: $C_{36}H_{65}NO_{26}$ 928.3795;

6-amino hexanyl α-D-galactopyranosyl-(1→4)-β-D-glucopyranosyl-(1→4)-α-D-glucopyranosyl-(1→4)-α-D-galactopyranosyl-(1→4)-β-D-glucopyranoside;

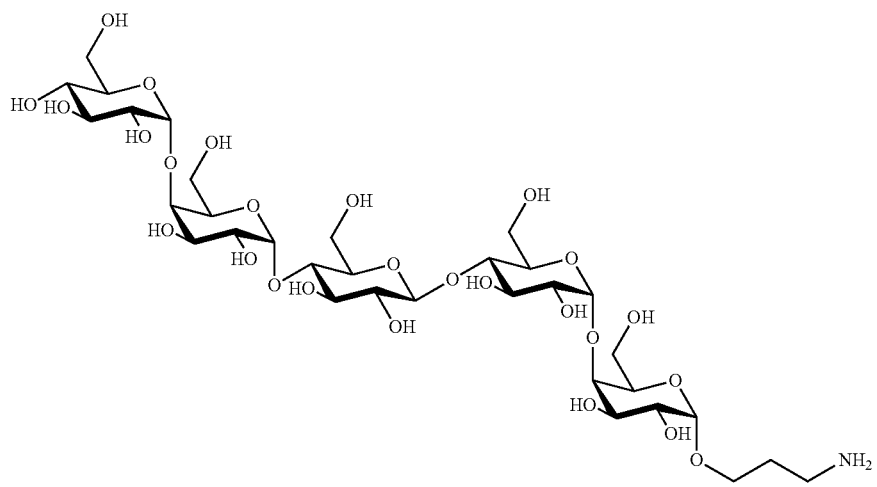
86
MS ESI+-HRMS m/z [M+H]+ calcd for: $C_{33}H_{59}NO_{26}$ 886.3325;
3-aminopropyl α-D-glucopyranosyl-(1→4)-α-D-galactopyranosyl-(1→4)-β-D-glucopyranosyl-(1→4)-α-D-glucopyranosyl-(1→4-α-D-galactopyranoside;
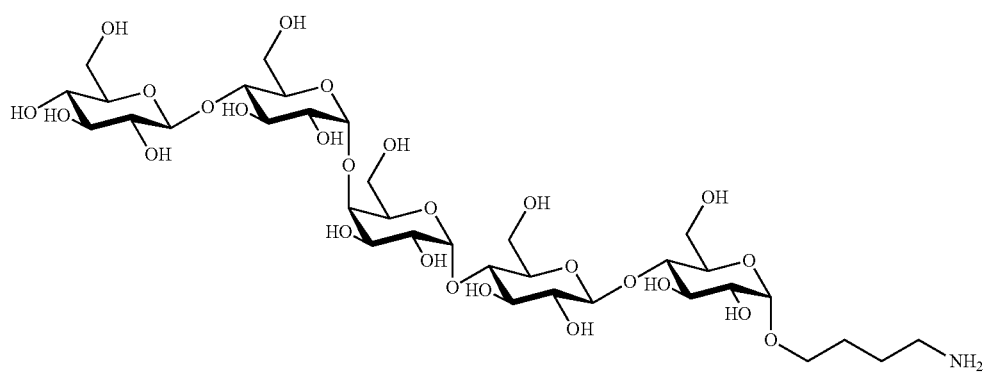
87
MS ESI+-HRMS m/z [M+H]+ calcd for: $C_{34}H_{61}NO_{26}$ 900.3482;
4-aminobutyl β-D-glucopyranosyl-(1→4)-α-D-glucopyranosyl-(1→4)-α-D-galactopyranosyl-(1→4)-β-D-glucopyranosyl-(1→4)-α-D-glucopyranoside;
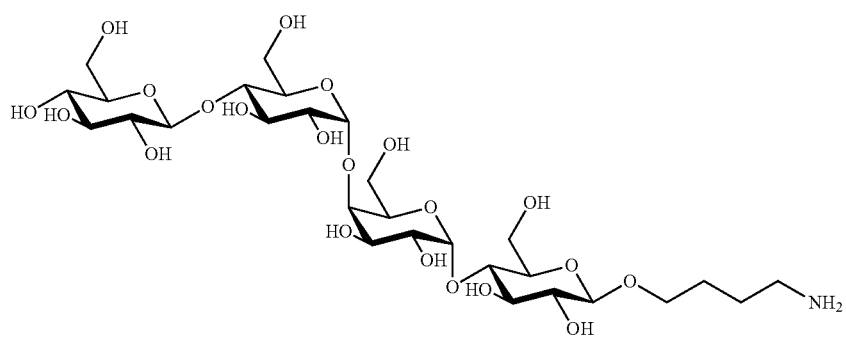
88
MS ESI+-HRMS m/z [M+H]+ calcd for: $C_{28}H5_1NO_{21}$ 738.2954;

4-aminobutyl β-D-glucopyranosyl-(1→4)-α-D-glucopyranosyl-(1→4)-α-D-galactopyranosyl-(1→4)-β-D-glucopyranoside;

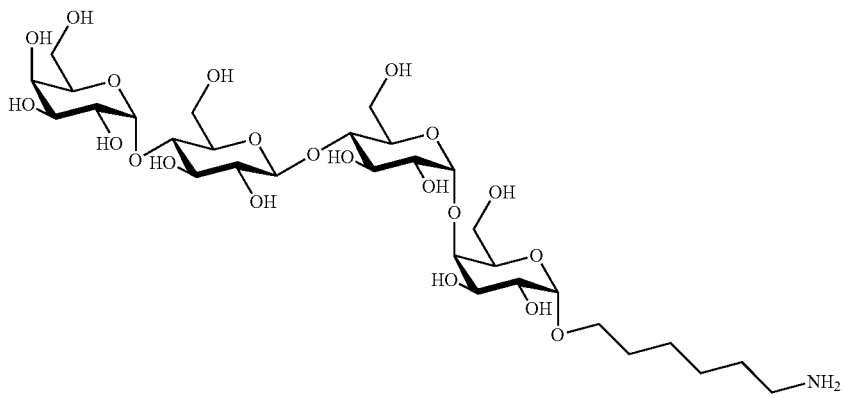

89

MS ESI+-HRMS m/z [M+H]+ calcd for: $C_{30}H_{55}NO_{21}$ 766.3267;

6-aminohexanyl α-D-galactopyranosyl-(1→4)-β-D-glucopyranosyl-(1→4)-α-D-glucopyranosyl-(1→4)-α-D-glucopyranoside.

Biological Experiments

Example 2-1

Synthesis of Microarrays using CodeLink NHS Slides

The indicated glycans were spotted onto CodeLink NHS slides using an automatic piezoelectric arraying robot (Scienion, Berlin, Germany) and incubated for 24 h (1% w/v in PBS) at room temperature. Slides were incubated in blocking buffer (100 mM ethanolamine in 50 mM NaPi pH>9) for 30 min at room temperature, washed three times each with water and ethanol, and dried. Slides were then blocked with 1% (w/v) bovine serum albumin in phosphate buffered saline for 1 h at 37° C., washed with water three times and dried.

Example 2-2

Binding Experiments using the Microarrays Synthesized According to the Procedure Described at Example 2.1

Binding experiments were performed by incubating microarray slides coated with the saccharides of general formula (I) with either a rabbit anti-SP8 typing serum or human pneumococcal reference serum 007sp (pooled sera of 287 humans immunized with Pneumovax® vaccine purchase from National Institute for Biological Standards and Control) in the dilutions indicated in the presence or absence of native SP8 polysaccharide, and using fluorescently labeled anti-rabbit (goat anti-rabbit IgG-FITC, abcam ab6717) or anti-human secondary antibodies (Alexa Fluor 488 goat anti-human IgM, Invitrogen A21215; Alexa Fluor 647 goat anti-human IgG, Invitrogen A21445).

Example 2-3
Conjugation of Synthetic Tetrasaccharides 10 and 18 to CRM$_{197}$ using Disuccinimidyl Adipate:
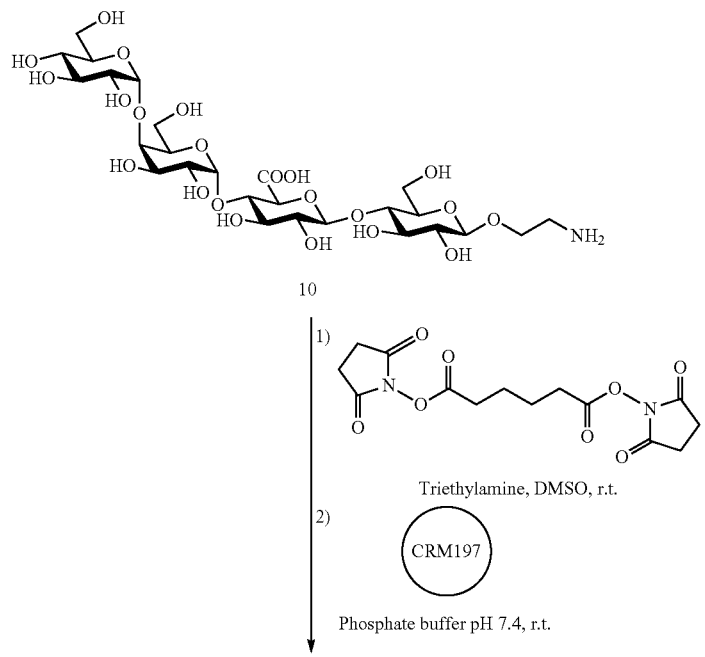
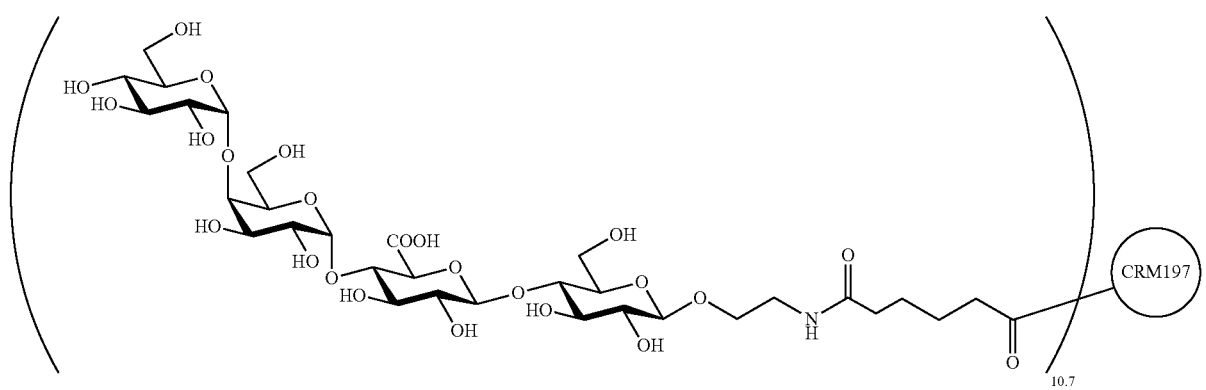

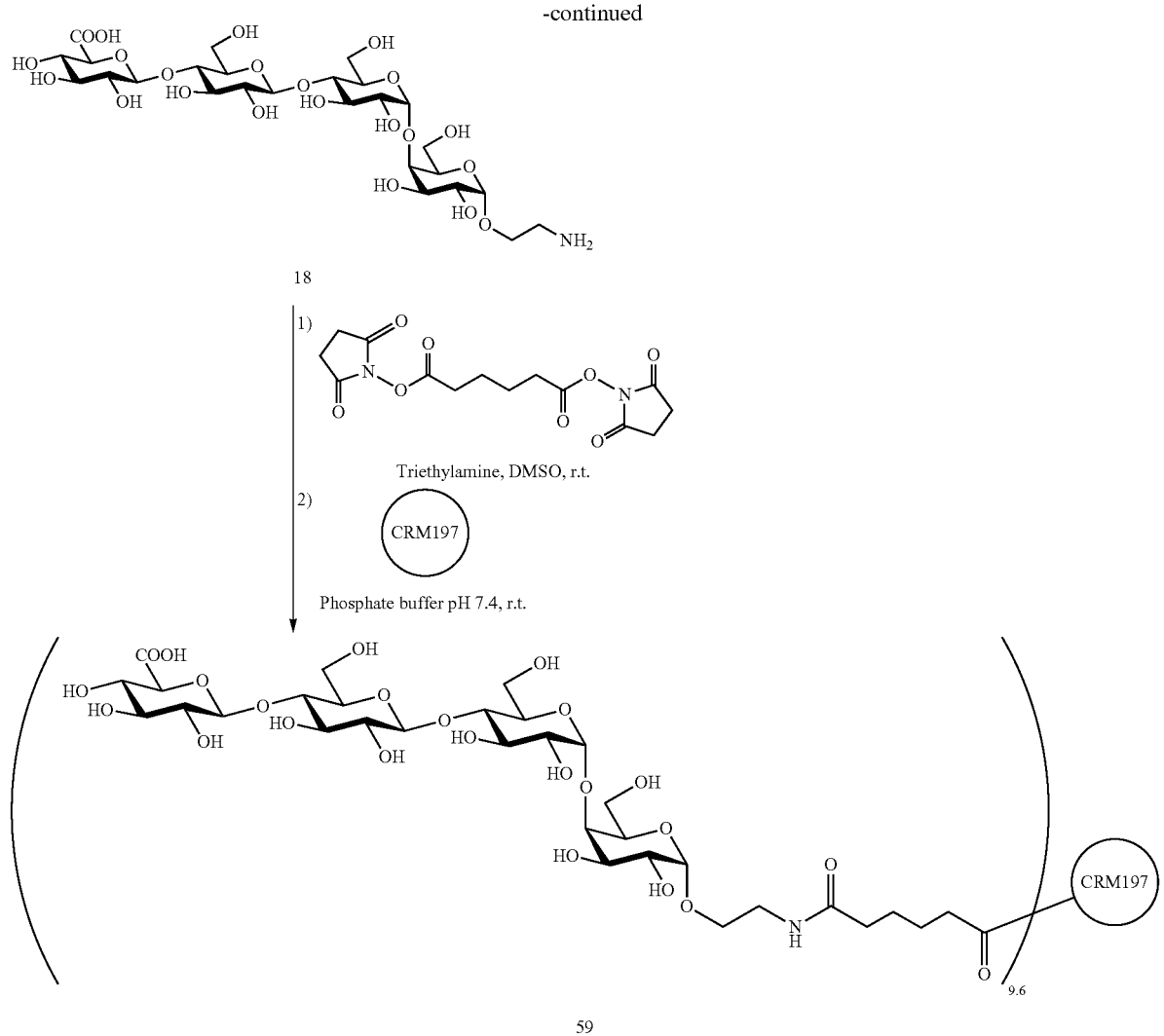

59

To a stirred solution of disuccinimidyl adipate (10 mg, 29 μmol) and triethylamine (10 μL, 72 μmol) in anhydrous DMSO (150 μL) was added at room temperature dropwise a suspension of tetrasaccharide 10 or 18 (approx. 2 mg, 2.8 μmol) in anhydrous DMSO (150 μL). The reaction was stirred for 2 h at that temperature under an Argon atmosphere and treated with a 100 mM sodium phosphate buffer pH 7.4 (NaPi, 200 μL). The mixture was extracted with chloroform (10 mL) and the phases separated by centrifugation (2 min, 1800 g, room temperature). The organic phase was discarded and the extraction step was repeated two times. The aqueous layer was clarified by centrifugation in a 1.5 mL reaction tube (1 min, 14500 g, room temperature) and added to a stirring solution of CRM$_{197}$ (1 mg, 17.3 nmol) in NaPi (1 mL). The mixture was stirred for 16 h at room temperature and dialyzed using a centrifugal filter (10 kDa MWCO, Millipore, Darmstadt, Germany). The conjugate was characterized by MALDI-MS:

Conjugate 58: ca. 67000 m/z (incorporation of 10.7 tetrasaccharide molecules on average)

Conjugate 59: ca. 66000 m/z (incorporation of 9.6 tetrasaccharide molecules on average)

Example 2-4

Immunization Procedure

Figure 1:
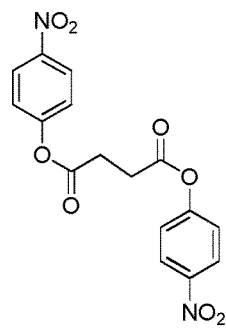
FIG. 1: Commercially available interconnecting molecules according to the present invention.
Figure 1:
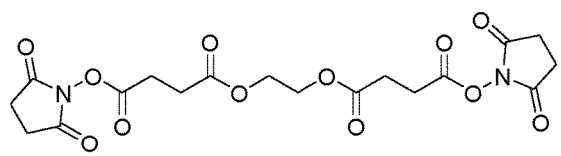
Figure 2:
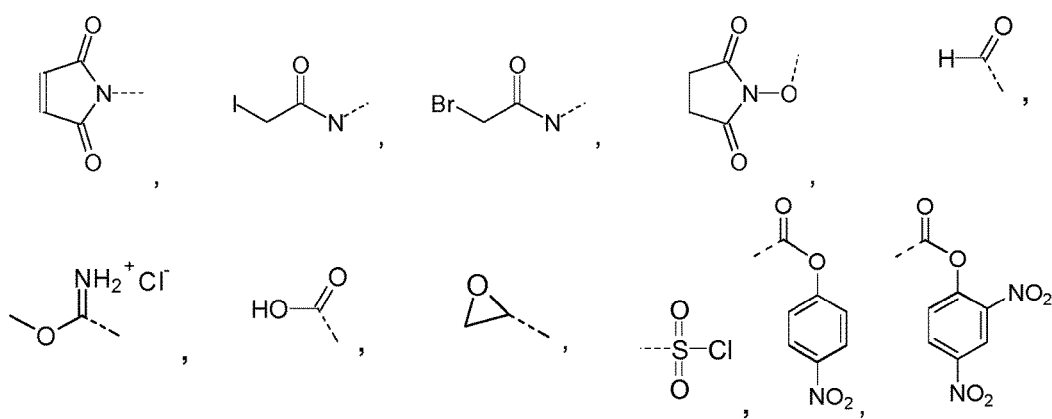
FIG. 2: Examples of functional group X of the interconnecting molecule according to the present invention.
Figure 3:
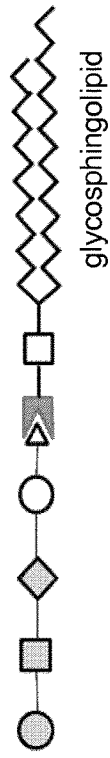
FIG. 3: Example of a (A) tetrasaccharide conjugated with a carrier protein. (B) tetrasaccharide conjugated with a glycosphingolipid. (C) tetrasaccharide conjugated on a solid support. The tetrasaccharide serves only as example and can be replaced by any saccharide of general formula (I).
Figure 3:
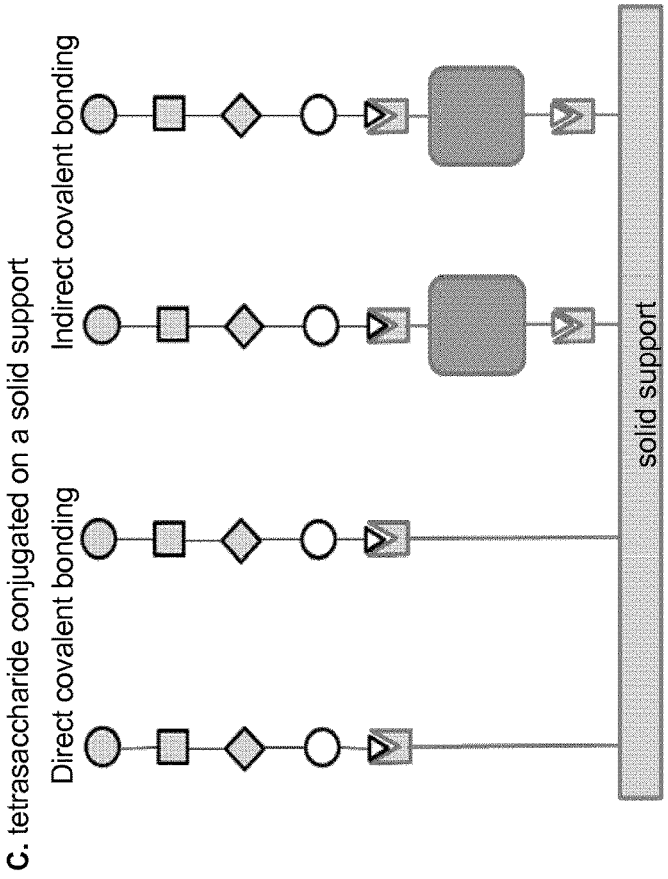
Figure 3:
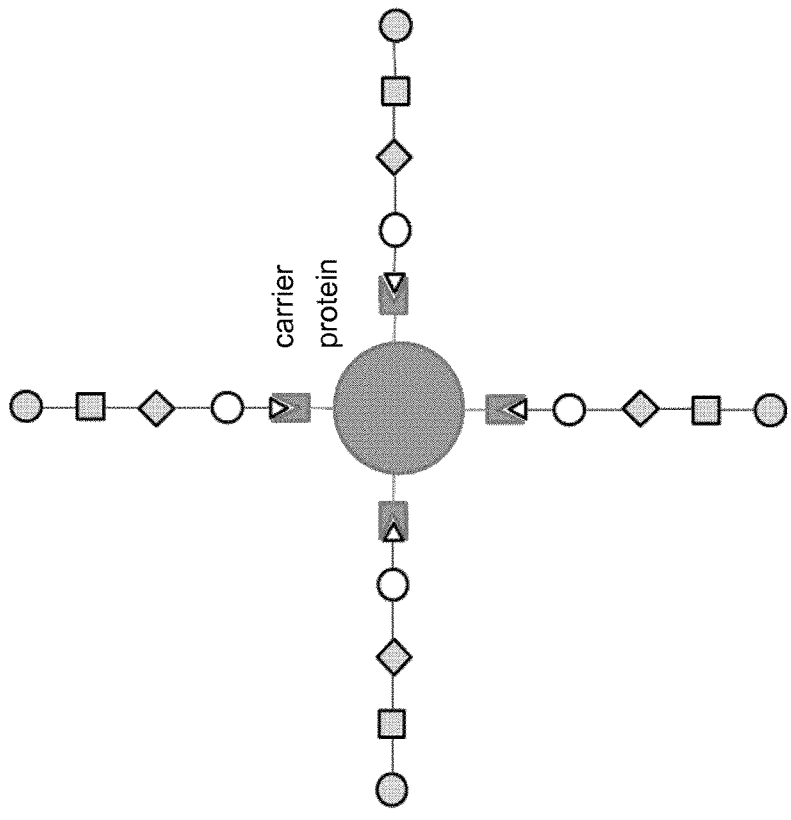
Figure 4:
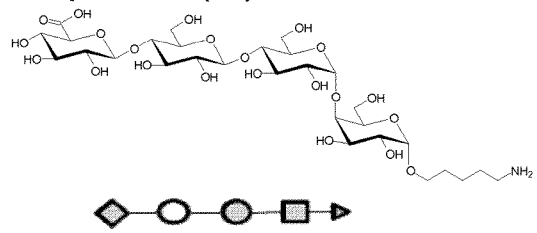
FIG. 4: (A) Saccharide symbols. (B) Glycan array analysis using commercially available serum 007sp: detection was performed using a fluorescently labelled anti-human IgM secondary antibody (Alexa Fluor 488 goat anti-human IgM, Invitrogen A21215) (C) Glycan array analysis using commercially available serum 007sp: detection was performed using a fluorescently labelled anti-human IgG secondary antibody (Alexa Fluor 647 goat anti-human IgG, Invitrogen A21445); (D) Glycan array analysis using a SP-8 specific rabbit typing serum: detection was performed using a fluorescently labelled anti-rabbit IgG secondary antibody (goat anti-rabbit IgG-FITC, abcam ab6717).
Figure 4:
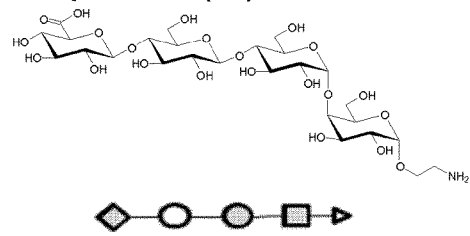
Figure 4:
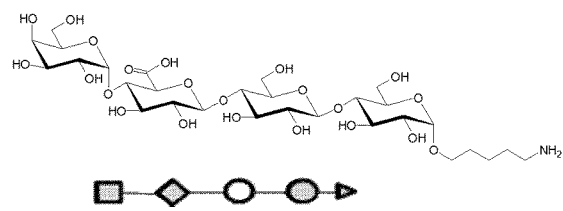
Figure 4:
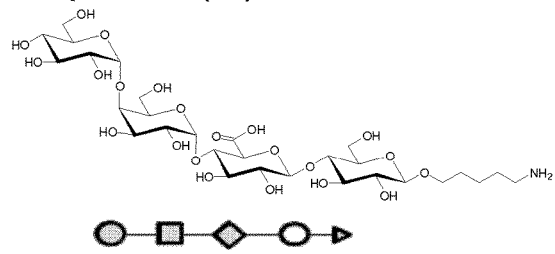
Figure 4:
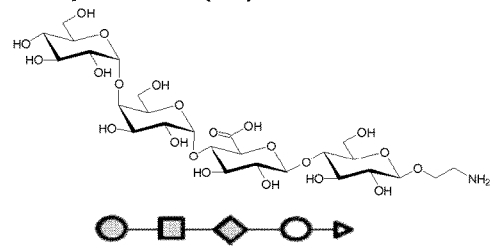
Figure 4:
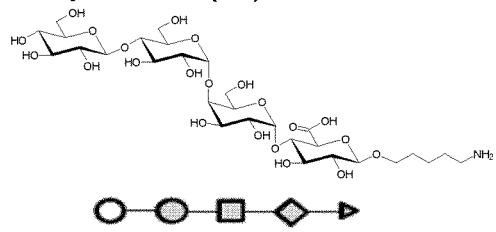
Figure 4:
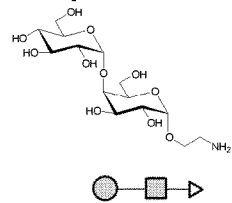
Figure 4:
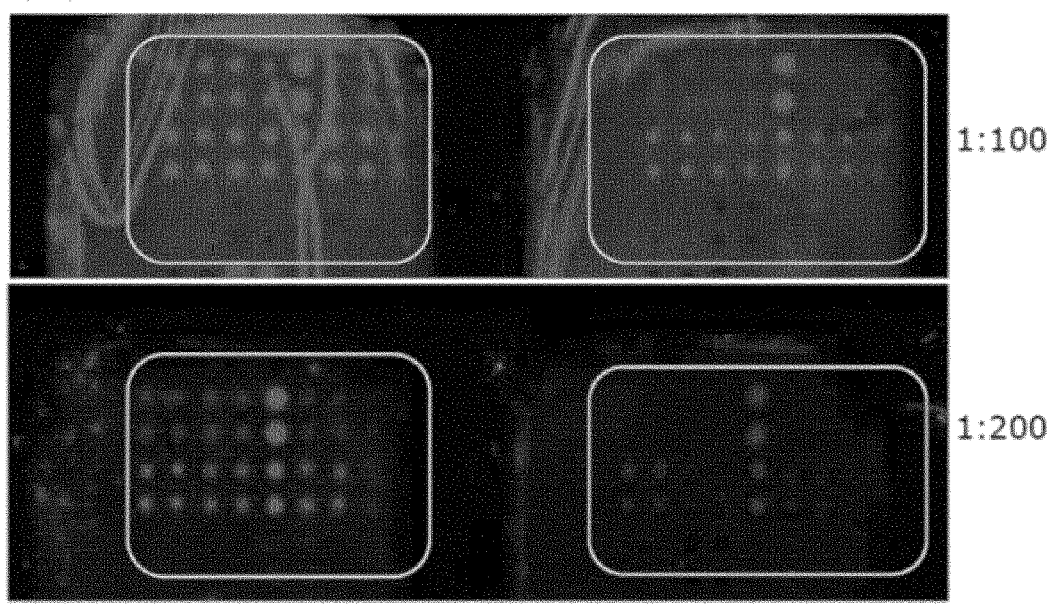
Figure 4:
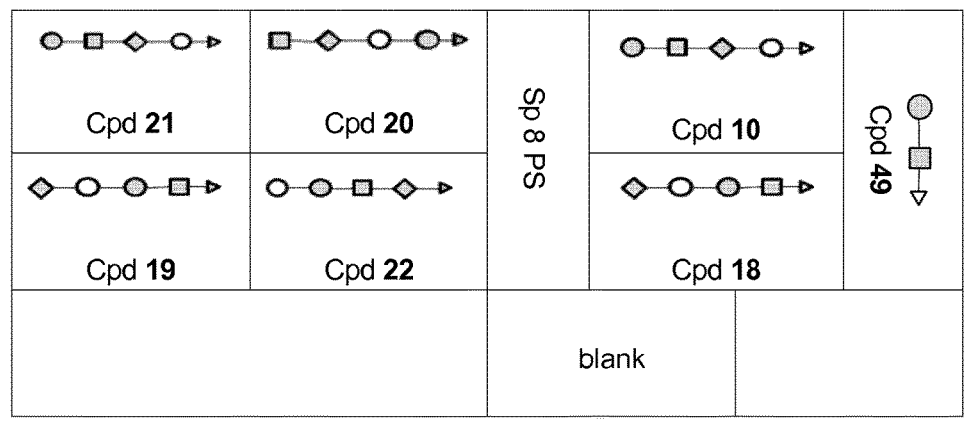
Figure 4:
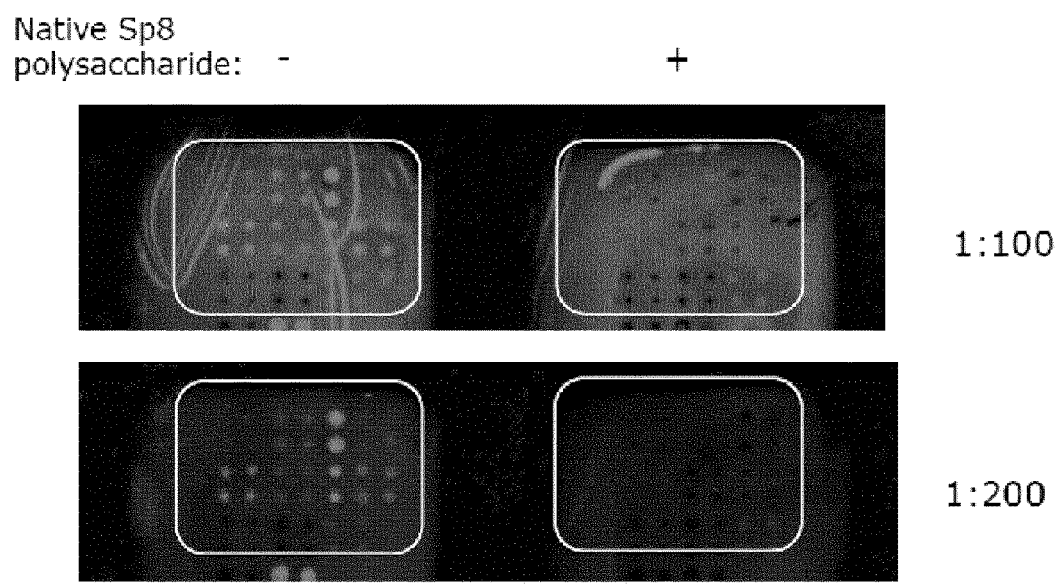
Figure 4:
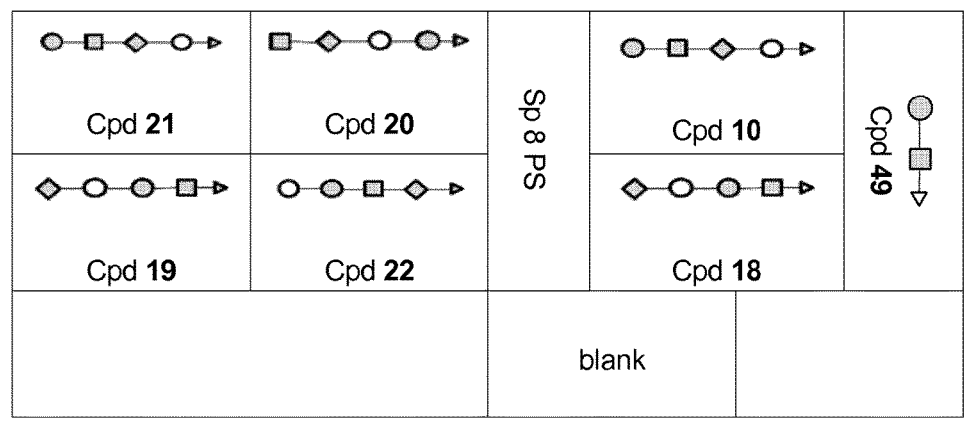
Figure 4:
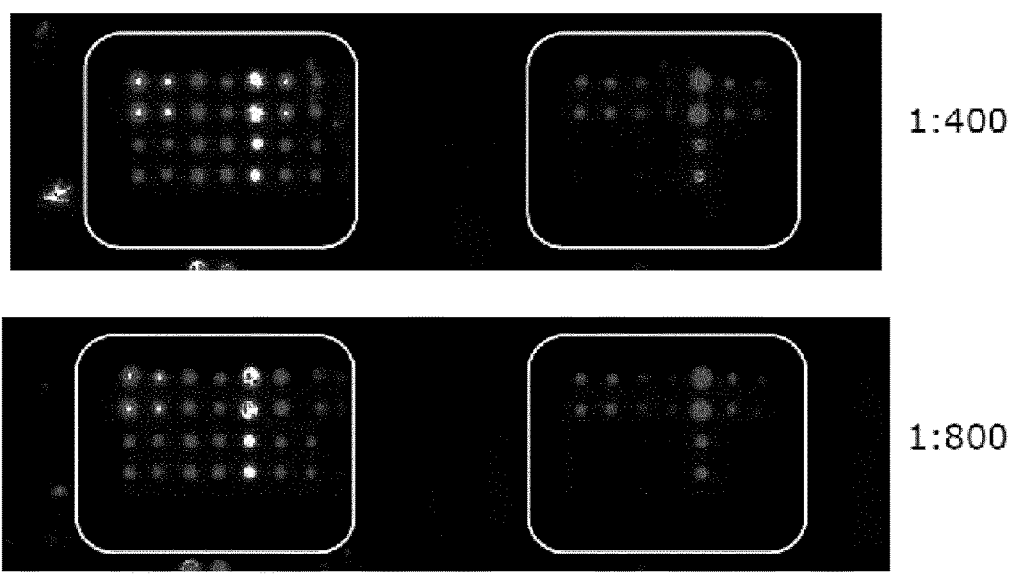
Figure 4:
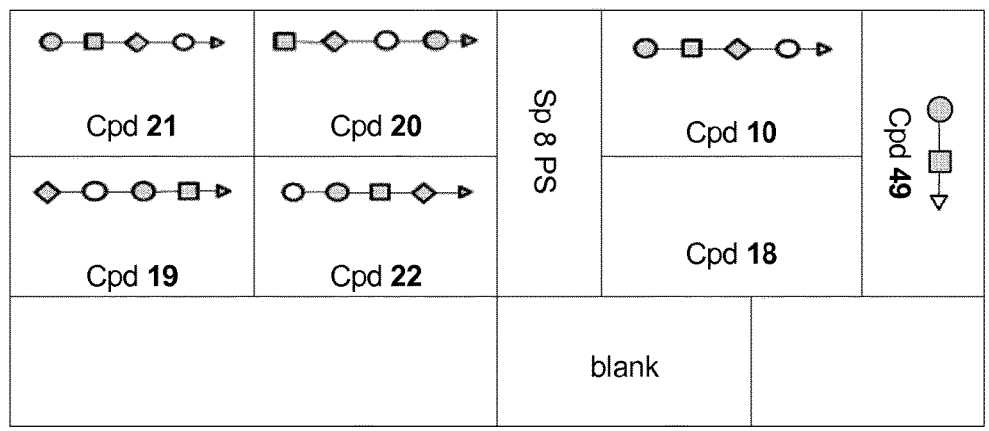
Figure 5:
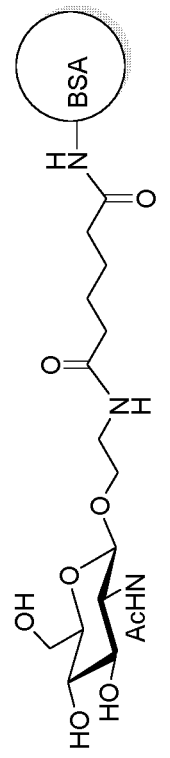
FIG. 5: Immune response of mouse 1160: (A) microarray printing pattern; (B) immune response of mouse 1160 (timeframe day 0 to day 35): detection was performed using a fluorescently labelled anti-mouse IgG secondary antibody (rabbit anti-mouse IgG-FITC, F9137, Sigma).
Figure 5:
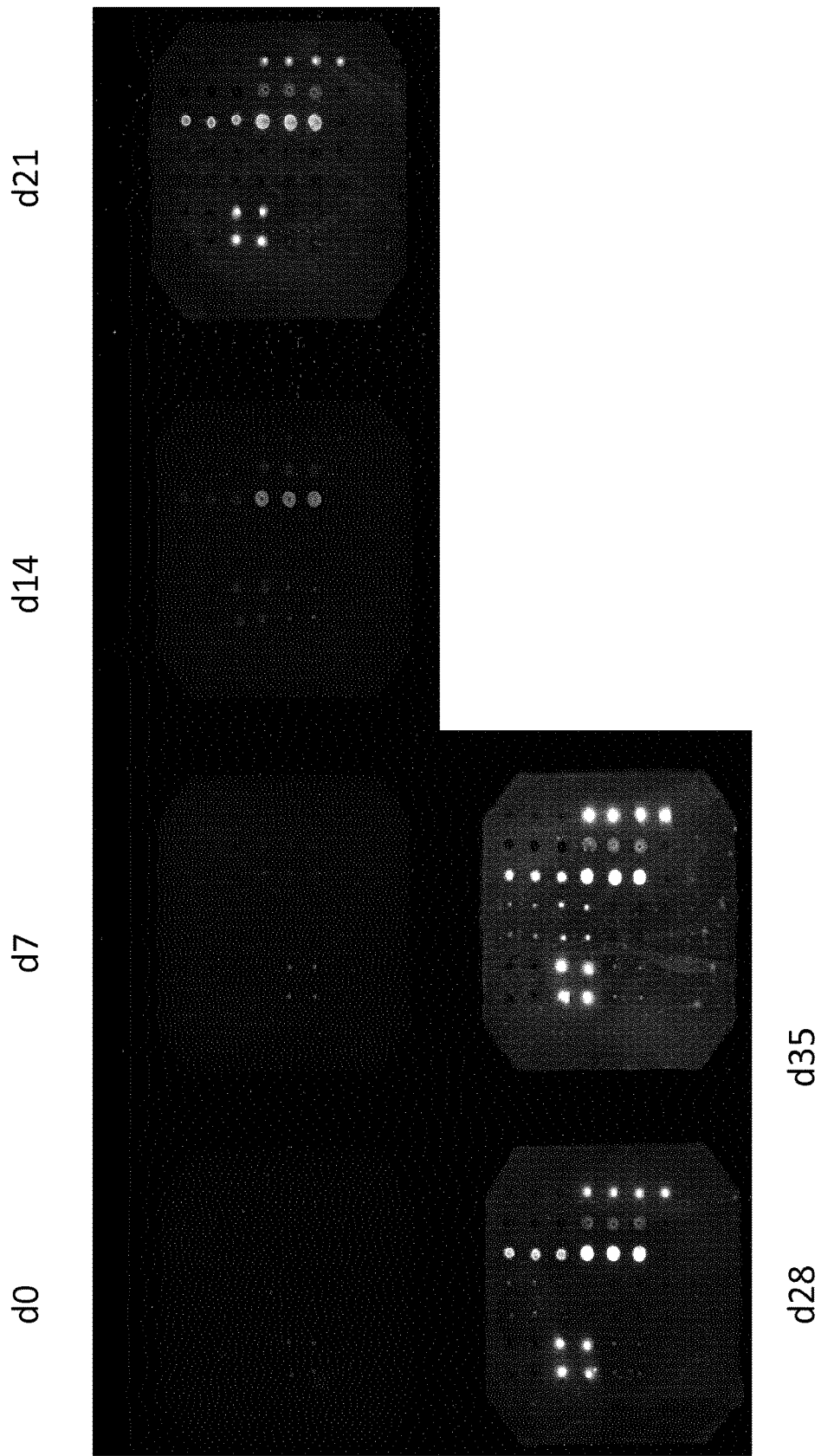

Mice (6-8 week old female Balb/c mice, Charles River) were immunized s. c. with CRM-Sp8 conjugates obtained at example 2.3 (corresponding to 4 pg synthetic glycan) formulated either with Freund's adjuvant (Sigma-Aldrich, St. Louis, US), Alum (Alhydrogel, Brenntag) or without adjuvant at a total volume of 100 μL at days 0, 14 and 28. The immune response was monitored by glycan array. The conjugate 59 induced an oligosaccharide-specific immune response in mouse #1160 receiving the said conjugate formulated with Freund's adjuvant. Importantly, a robust immune response was observed in immune serum from mouse #1160 against the native Sp8 polysaccharide (see FIG. 5).

Example 2-5

Generation of Monoclonal Antibodies

Monoclonal antibodies were prepared using BM-Condimed H1 (Roche, Penzberg, Germany) according to the manufacturer's instructions. Following fusion, single clones were generated using limited dilution and two subsequent rounds of subcloning. Antibody production was monitored by glycan array and ELISA. 33 clones were eventually isolated that produced mAbs recognizing both tetrasaccharide 19 and Sp8 native polysaccharide.

Figure 6:
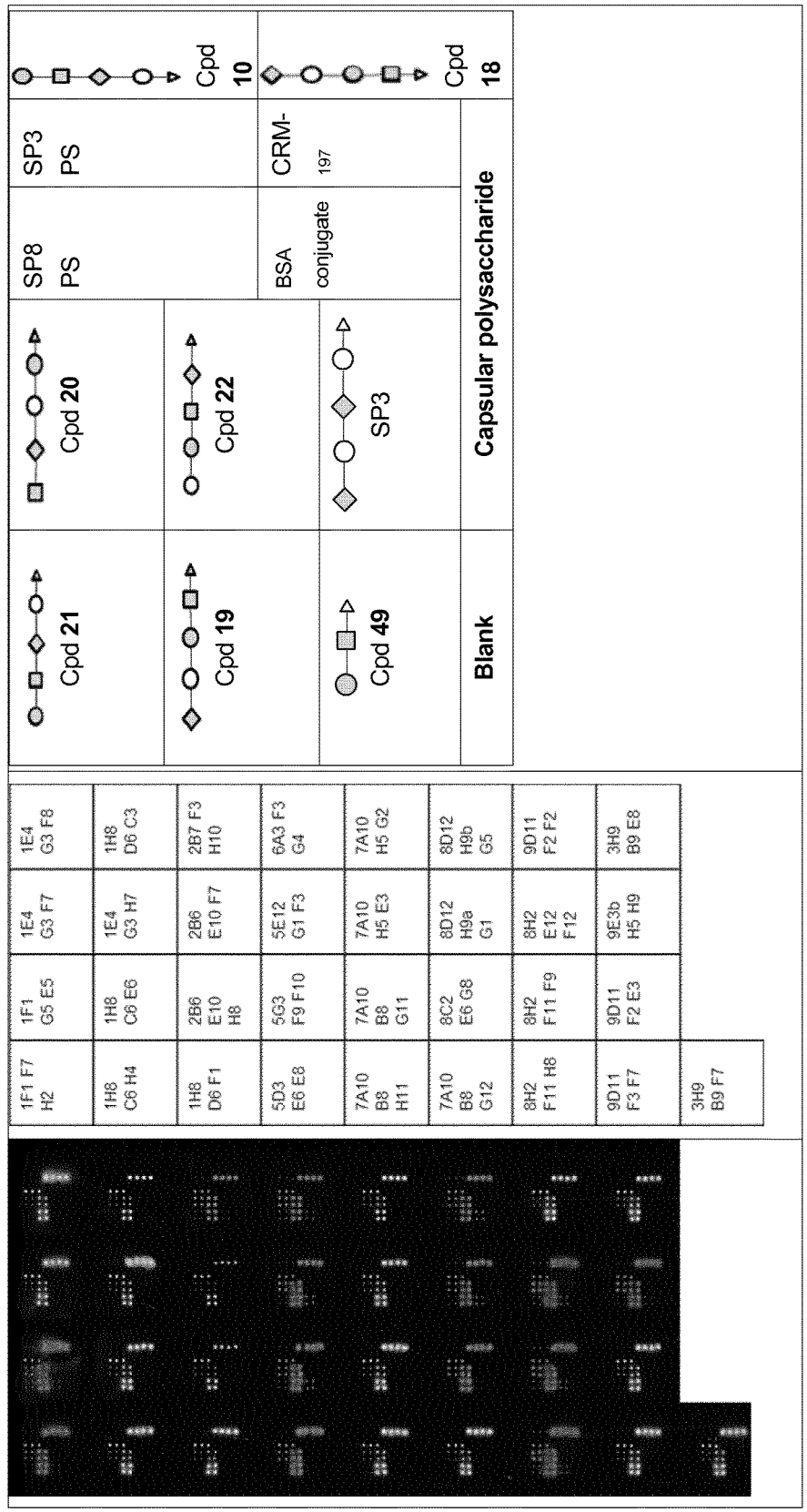
FIG. 6: Generation of anti SP-8 monoclonal antibodies: detection was performed using a fluorescently labelled anti-mouse secondary antibody (Alexa 635 goat anti-mouse IgG, Invitrogen A31574).

Clones 1H8 and 1F1 were expanded in serum-free medium. MAb 1H8 was purified from the cell culture supernatant using a Protein G Antibody Purification kit (Pro-Chem, Littleton, USA) (see FIG. 6). MAb 1F1 was purified by gel filtration chromatography using a HiLoad 16/60 Superdex column (GE Healthcare, Little Chalfont, UK) with PBS as buffer.

Example 2-6

Enzyme-linked Immunosorbent Assay (ELISA)

ELISA was performed using high-binding polystyrene 96-well plates (Corning, Corning, US). Plates were coated using native Sp8 polysaccharide (SSI Diagnostica, Kopenhagen) at a concentration of 10 μg/mL in PBS for 20 h at 4° C. Plates were blocked with 10% (v/v) fetal calve serum in PBS for 1 h at 37° C. and washed once with PBS containing 0.1%) (v/v) Tween 20 (PBS-T). Cell culture supernatants of anti-Sp8 mAbs (50 μL) were applied. Plates were incubated for 1 h at 37° C., washed with PBS-T three times and treated with a horseradish peroxidase (HRP)-labeled secondary antibody (goat anti-mouse IgG HRP conjugate, dianova, Hamburg, Germany). Plates were washed with PBS-T three times and HRP activity was measured with TMB substrate (BD Biosciences, San Jose, US) according to the manufacturer's instructions. Monoclonal antibodies generated from #1160 specifically recognized both synthetic saccharide 19 and the native Sp8 polysaccharide, as assessed by ELISA.

Example 2-7

Surface Plasmon Resonance

Figure 7:
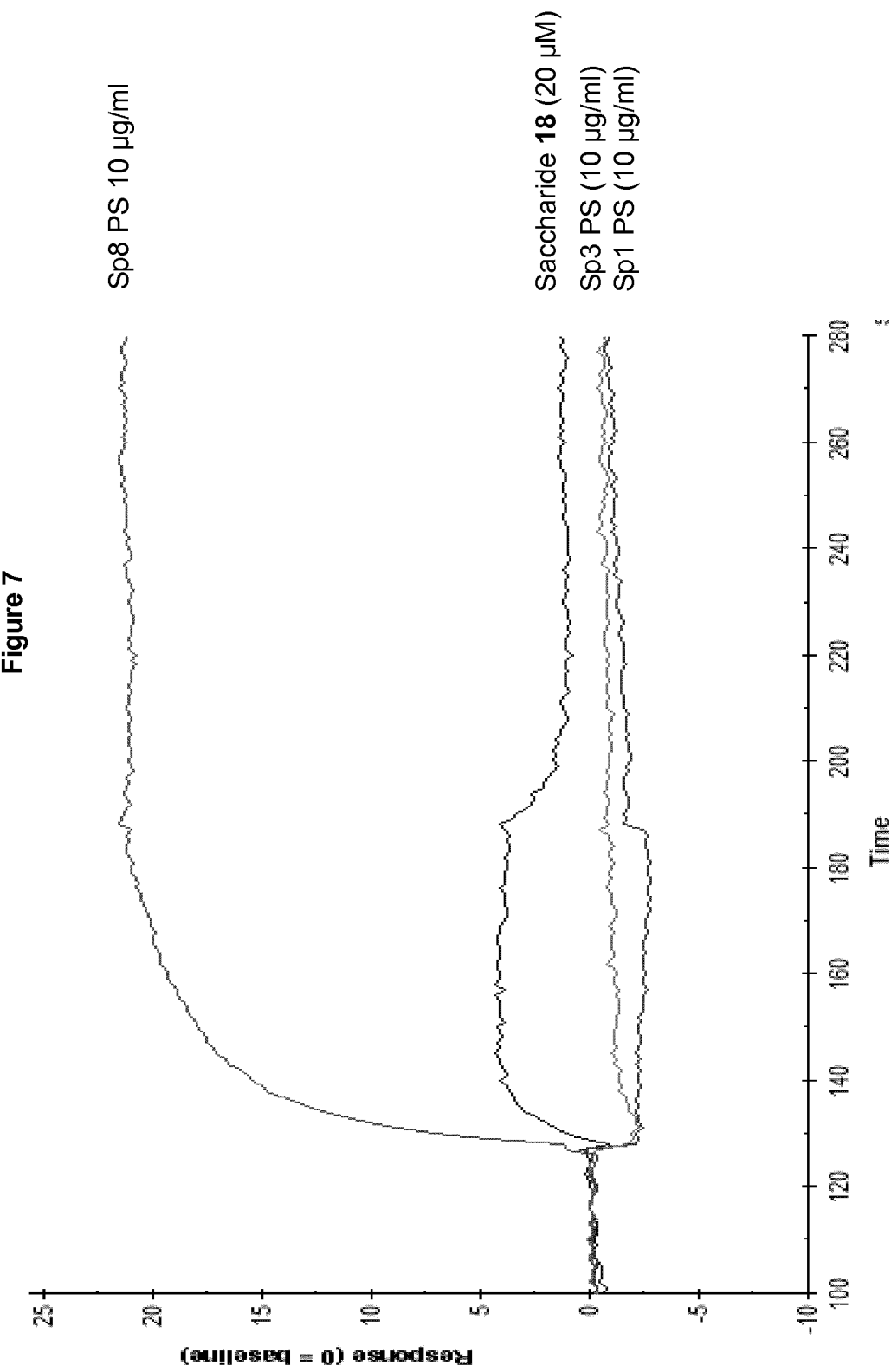
FIG. 7: Surface plasmon resonance: monoclonal antibody mAb 1H8 specifically recognizes both synthetic saccharide 18 and the native Sp8 polysaccharide.

Surface Plasmon Resonance was performed on a Biacore T100 instrument (GE Healthcare). Analysis was performed using the Mouse Antibody Capture Kit and Amine Coupling Kit (GE Healthcare) for immobilization. About 10000 response units (RU) of capture antibody were immobilized. A commercial mouse IgG (cat. no. 026502, Invitrogen, Carlsbad, US) was immobilized as a dummy in a reference cell (about 10000 RU). About 800 RU of mAb 1H8 were captured prior to every run using a mAb concentration of 50 μg/mL. Runs were performed using PBS as a running buffer and a flow rate of 30 μL/min with 60 s association and 120 s dissociation periods, respectively. Polysaccharides were used at a concentration of 10 μg/mL and saccharide 18 at 20 μM in PBS. Monoclonal antibody mAb 1H8 specifically recognizes both synthetic saccharide 18 and the native Sp8 polysaccharide (see FIG. 7).

Example 2-8

Immunofluorescence of UV-inactivated S. pneumoniae

Figure 8:
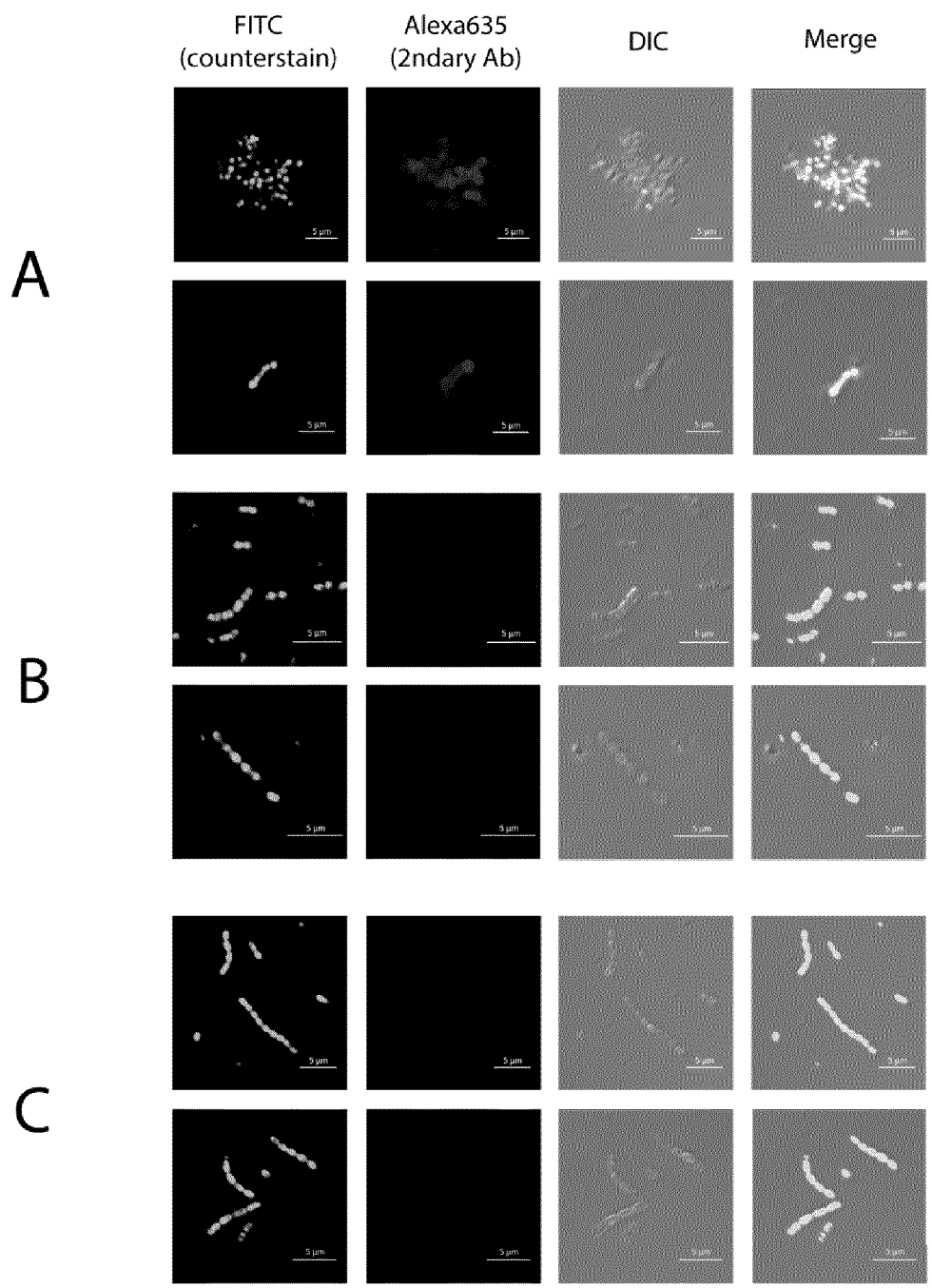
FIG. 8: Immunofluorescence staining results: immunization with conjugate 59 induces an immune response that recognizes the native SP-8 polysaccharide and ST8 bacteria. Bacteria were labeled with FITC and incubated with the indicated primary antibodies. Antibody binding was visualized after incubation with Alexa 635-labeled goat anti-mouse IgG secondary antibody (A31574, Invitrogen). (A) S. pneumoniae ST8, mAb 1H8; (B) S. pneumoniae ST8, mAb isotype control (anti Y. pestis LPS core); (C) S. pneumoniae ST1; mAb 1H8.

S. pneumoniae serotype 8 (ATCC 6308) or serotype 1 (ATCC 6301) (approx. $4 \times 10^8$ cfu/mL) were inactivated by irradiation with 254 nm for 10 min in PBS at room temperature. Cells were harvested by centrifugation, washed once with PBS and frozen in Todd Hewitt Broth containing 0.5% (w/v) yeast extract and 20% (v/v) glycerol. For immunofluorescence, bacteria ($8 \times 10^8$ cfu ST8 or $4 \times 10^8$ cfu ST1) were thawed, harvested by centrifugation (16800 g, 15 min, r.t.) and washed once in buffer A (50 mM $NaHCO_3$, 100 mM NaCl, pH 7.5). Cells were resuspended in buffer A (1 mL) and treated with a fluorescein isothiocyanate (FITC, Sigma-Aldrich) solution (10 mg/mL in DMSO) to a final concentration of 0.1 mg/mL. Bacteria were labeled in the dark for 1 h at 37° C., harvested by centrifugation and washed twice with 0.25% (w/v) BSA in PBS (1 mL). Labeling was monitored by fluorescence microscopy using an Axio Imager.M2 system equipped with a LSM 700 confocal laser scanning microscope (Carl Zeiss Microscopy GmbH, Jena, Germany). Cells were suspended in 1% (w/v) BSA in PBS (1 mL for ST8, 0.5 mL for ST1) and the suspension was distributed into two aliquots. The suspensions were treated with mAb 1H8 or mAb 1E12 (IgG1) against *Yersinia pestis* lipopolysaccharide core trisaccharide as an isotype control to a final mAb concentration of 10 μg/mL. Bacteria were incubated in the dark for 16 h at 4° C. under agitation and washed with 1% (w/v) BSA in PBS (0.5 mL). The cells were suspended in a solution of goat anti-mouse IgG-Alexa635 conjugate (1:100 dilution in 200 μL 1% (w/v) BSA in PBS, Invitrogen), incubated in the dark for 1.5 h at room temperature and washed with 1% (w/v) BSA in PBS and PBS (0.5 mL, respectively). Fluorescently labeled bacteria were visualized by fluorescence microscopy and images were processed with using Zen 2011 software (Carl Zeiss Microscopy GmbH). As shown in FIG. 8, immunization with conjugate 59 induces the formation of antibodies that recognize the native SP-8 polysaccharide and ST8 bacteria.

Example 2-9

Figure 9:
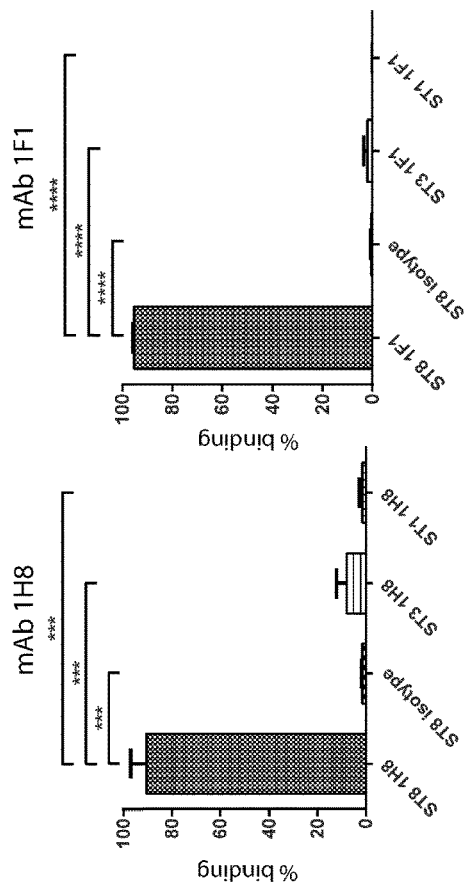
FIG. 9: Flow cytometry of fluorescently labelled pneumococci: (A) Representative flow cytometry result after labelling with mAb 1H8 or an isotype control; (B) Cumulated results of at least 3 independent labeling experiments using mAbs 1H8 or 1F1. Histograms show mean ±SD of positive binding. *P<0.001; **P<0.0001. Both monoclonal antibodies 1H8 and 1F1 bind to *S. pneumoniae* serotype 8, but do not bind to *S. pneumoniae* serotypes 1 or 3. Interactions between monoclonal antibodies and *S. pneumoniae* type 8 pneumococci are specific since no binding can be observed by antibody isotype controls or towards *S. pneumoniae* serotypes 1 or 3
Figure 9:
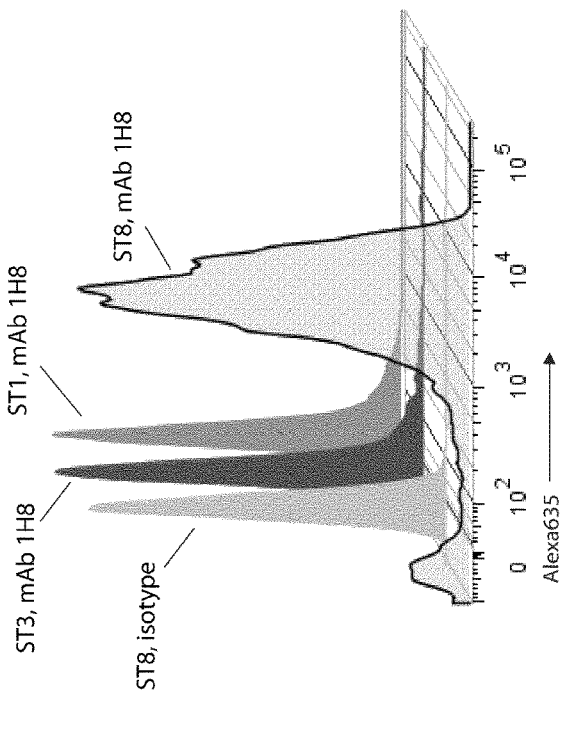

Assessment of the Binding of mAbs 1H8 and 1F1 to S. pneumoniae Serotype 8 Bacteria by Flow Cytometry S. pneumoniae serotype 8 (ATCC 6308), serotype 1 (ATCC 6301) or serotype 3 (PN36, NCTC7978) were UV-inactivated, FITC-labeled and treated with a fluorescent secondary antibody (anti-mouse IgG-Alexa635 conjugate or anti-mouse IgM-Alexa680 conjugate, Invitrogen) as described before (see Example 2.8). Flow cytometry was performed using a FACSCanto II flow cytometer (BD Pharmingen, Heidelberg, Germany) and analyzed using FlowJo software (Tree Star Inc., Ashland, Oreg., USA). Both monoclonal antibodies 1H8 and 1F1 bind to *S. pneumoniae* serotype 8, but do not bind to *S. pneumoniae* serotypes 1 or 3 (see FIG. 9). Interactions between monoclonal antibodies and ST8 pneumococci are specific since no binding can be observed by antibody isotype controls or towards *S. pneumoniae* serotypes 1 or 3.

Example 2-10

Opsonophagocytotic Killing Assay

A opsonophagocytotic killing assay was employed as described in Romero-Steiner et al., Clin. Diagn. Lab. Immunol., 1997, 4. Briefly, HL-60 cells were differentiated for one week with N,N-dimethylformamide as reported (Romero-Steiner et al., 1997), washed twice with OPKA buffer (Hanks' buffer with 0.1% (w/v) gelatin) and diluted to a density of $10^7$ cells/mL in the same buffer directly before use. Bacteria were grown in growth medium (Todd-Hewitt broth+0.5% (w/v) yeast extract) at 37° C/5% $CO_2$ to log phase (OD 0.2-0.3), diluted in freezing medium (growth medium with 15% (v/v) glycerol) to a density of approx. $10^6$ cells/mL and frozen in 0.5 mL aliquots at −80° C. Bacteria were diluted with OPKA buffer and aliquoted (1000 cells in 20 µL each) in a 96 well-plate. Bacterial suspensions were treated with appropriate antibody or antisera (1:4 dilutions) and incubated for 15 min at 37° C. Complement source (baby rabbit complement, CedarLane, 10 µL) and differentiated HL-60 cell suspension (40 µL, phagocyte/bacteria ratio 400:1) were added and the suspensions incubated for 45 min at 37° C. with shaking (220 rpm). Opsonophagocytosis was performed in triplicates. 10% of the contents of each well were plated on Columbia Agar plates and colonies were counted after 10-12 h incubation at 37° C./5% $CO_2$. Control wells lacked either antibody or complement sources.

Figure 10:
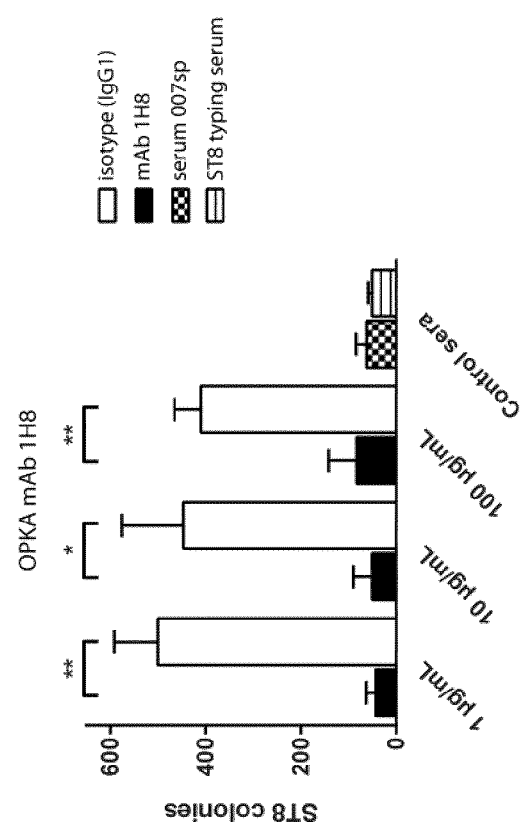
FIG. 10: Opsonophagocytotic killing of *S. pneumoniae* serotype 8 bacteria in the presence of mAb 1H8: mAb 1H8, but not an isotype antibody, opsonizes live bacteria for killing by phagocytes at all tested doses with a similar efficiency as pooled sera from Pneumovax23® vaccinated humans (007sp, 1:4 dilution) and rabbit ST8 typing serum (1:4 dilution).

Monoclonal antibody 1H8 raised against synthetic S. pneumoniae serotype 8 tetrasaccharide 18, but not an isotype control mAb, exhibited a similar opsonophagocytotic killing capacity in the presence of complement and differentiated HL-60 cells as control sera in all concentrations tested (rabbit S. pneumoniae type 8 typing serum (1:4 dilution) and human antiserum 007sp (1:4 dilution), respectively) (see FIG. 10).

Example 2-11

Glycan Array Analysis using the Monoclonal Antibodies mAbs 1H8 and 1F1

Binding experiments were performed by incubating microarray slides synthesized as shown in Example 2.1 in the presence or absence of SP8 capsular polysaccharide and including compounds 19, 49, 90, 60, 62, 55 and 57.

Figure 11:
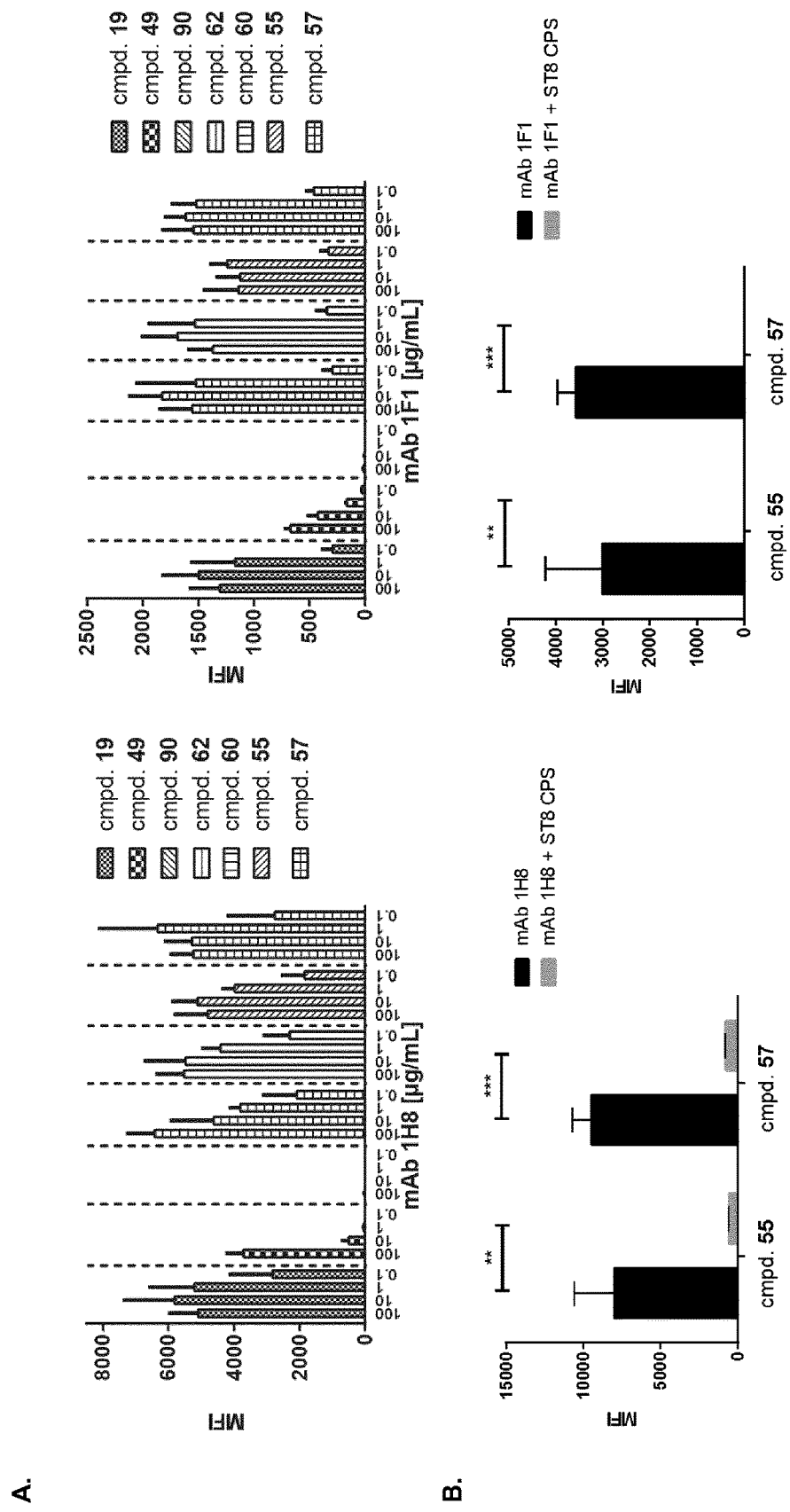
FIG. 11: (A) Microarray analysis of the binding of mAb 1H8 and 1F1 to saccharides 19, 49, 90, 60, 62, 55 and 57. Histograms show mean±SD of fluorescence intensities normalized to background of 4 spots. MFI, mean fluorescence intensity: trisaccharide 62, tetrasaccharide 19, tetrasaccharide 60, pentasaccharide 55 and hexasaccharide 57, but not the smaller structures 49 and 90, are recognized with similar intensities by mAbs 1H8 and 1F1.
Figure 11:
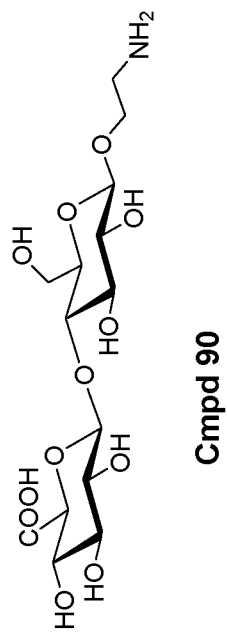

As shown by FIG. 11, trisaccharide 62, tetrasaccharide 19, teteasaccharide 60, pentasaccharide 55 and hexasaccharide 57, but not the smaller structures 49 and 90, are recognized with similar intensities by mAbs 1H8 and 1F1.

As shown in FIG. 11, binding of mAbs 1H8 and 1F1 to pentasaccharide 55 and hexasaccharide 57 was abrogated by inhibition with native SP8 polysaccharide, confirming that these saccharides harbor overlapping epitopes with the native polysaccharide.

Example 2-12

Assessment of the Binding of mAb 28H11 to the Saccharides of the Present Invention by Microarray Glycan arrays were fabricated as shown above (Example 2-1 and 2-2), except that a murine monoclonal antibody 28H11 (IgM) raised against native Sp8 polysaccharide (Yano and Pirofski (2011), *Clin. Vaccine Immunol.*, 18 (1), 59-66) was used for binding at different dilutions with or without addition of 10 µg/mL S. pneumoniae type 8 CPS. A Donkey anti-Mouse IgM Alexa Fluor® 594 conjugate (dianova, Hamburg, Germany) was used as a secondary antibody for detection.

MAb 28H11, a murine IgM that has been raised against native S. pneumoniae type 8 CPSs, is well-characterized and protects mice from infection with live S. pneumoniae type 8 pneumococci in various settings (Yano and Pirofski (2011), *Clin. Vaccine Immunol.*, 18 (1), 59-66). Glycan microarray analysis revealed a robust interaction of mAb 28H11 with saccharide 19 that was specific to S. pneumoniae type 8, as shown by the ablation of binding by native S. pneumoniae type 8 CPSs of up to 10 µg/mL (see FIG. 12).

Example 2-13

Conjugation of a Oligosaccharides to $CRM_{197}$ using bis(4-nitrophenyl)adipate To a stirred solution of the oligosaccharide (amount specified below; typically 0.2 pmol) in a 1:3 (v/v) mixture of anhydrous DMSO and anhydrous pyridine (100-200 µL) were added bis(4-nitrophenyl)adipate (12 equivalents relative to the amount of sugar; typically 2.4 µmol) and triethylamine (10 µL). The reaction was stirred for 2 h at room temperature under an Argon atmosphere. The mixture was shock-frozen and lyophilized. The residue was triturated with chloroform (4×0.5 mL) and dichloromethane (4×0.5 mL), transferred to a new reaction tube using DMSO as a solvent and lyophilized again. $CRM_{197}$ (3 mg, 52 nmol) was dialyzed twice against 0.1 M sodium phosphate buffer pH 8.0 using a centrifugal filter (10 kDa MWCO, Millipore, Darmstadt, Germany), concentrated to approx. 300 µL and added to the activated oligosaccharide. The mixture was stirred at room temperature for 16 h and dialyzed (see above) four times against water. An aliquot was taken for characterization and the mixture was dialyzed three times against phosphate-buffered saline. The glycoconjugates were characterized by MALDI-TOF MS (see FIG. 13), SDS-PAGE and Western Blot.

Exact Quantities of Oligosaccharides Used:

Tetrasaccharide 18: 2.6 µmol (1.9 mg)

Tetrasaccharide 60: 2.1 µmol (1.5 mg)

Hexasaccharide 57: 1.9 µmol (2.0 mg)

Conjugate $CRM_{197}$-18: ca. 65503 m/z (incorporation of 8.8 tetrasaccharide molecules on average);

Conjugate $CRM_{197}$-60: ca. 68281 m/z (incorporation of 12.9 tetrasaccharide molecules on average);

Conjugate $CRM_{197}$-57: ca. 63535 m/z (incorporation of 4.6 hexasaccharide molecules on average).

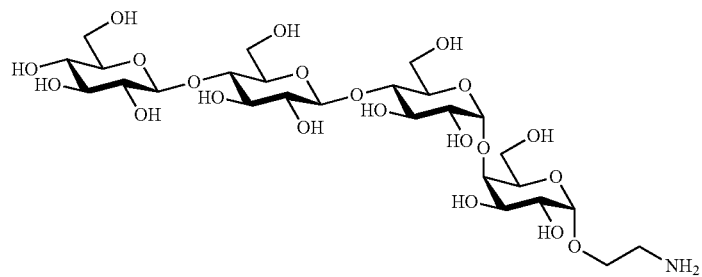
60
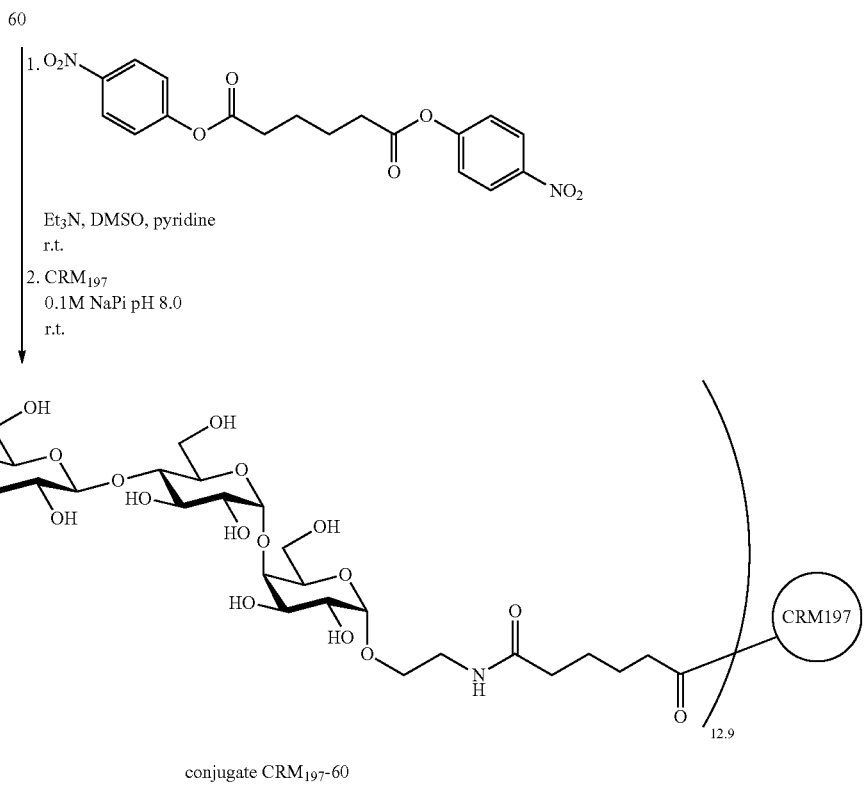
conjugate CRM₁₉₇-60
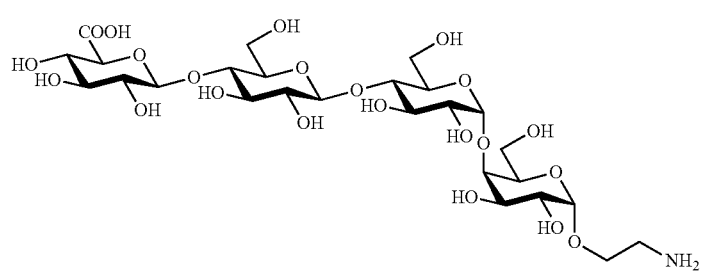
18
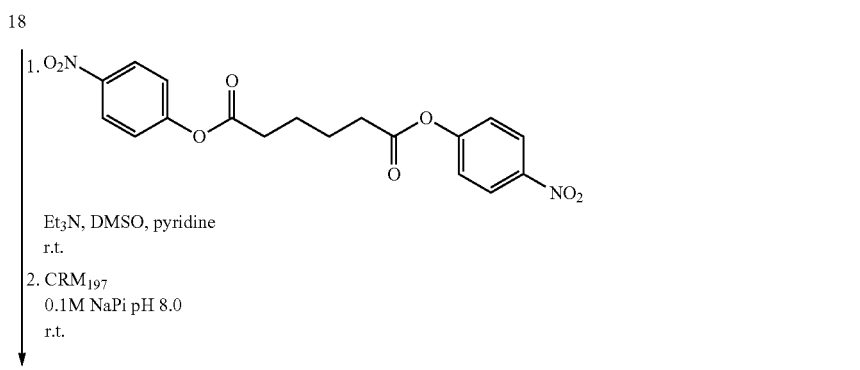

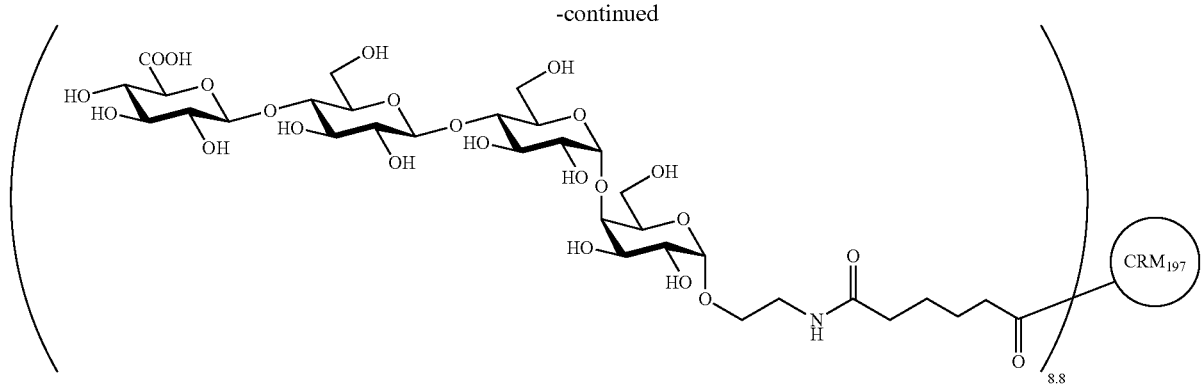
conjugate CRM₁₉₇-18
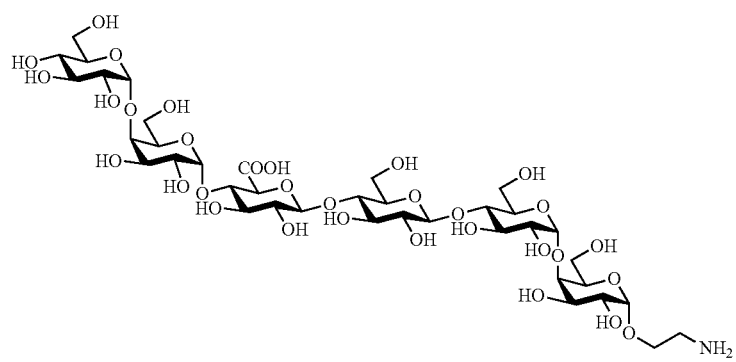
57
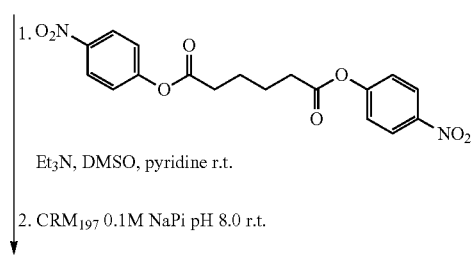
Et₃N, DMSO, pyridine r.t.
2. CRM₁₉₇ 0.1M NaPi pH 8.0 r.t.
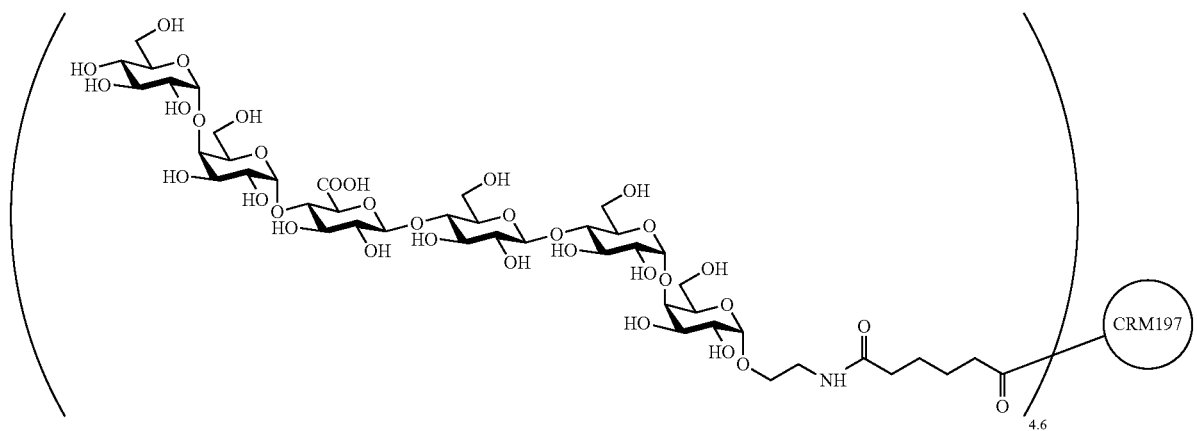
CRM₁₉₇-57

Example 2-14

Evaluation of the Immune Response Against the Conjugates of Example 2-13 in Rabbits Rabbits (n=3 per group) were immunized subcutaneously at multiple sites with glycoconjugates CRM197-18, CRM197-60 or CRM197-57 (10 μg glycan per dose) or $CRM_{197}$ (100 μg) at days 0 and 14. Serum was collected at days 0, 14 and 21. The results of the immunization studies are summarized by FIG. 15.

All rabbits immunized with conjugates show a marked immune response against *S. pneumoniae* type 8 CPS-related oligosaccharides and *S. pneumoniae* type 8 CPS. Hence, all conjugates induce immunity against *S. pneumoniae* bacteria in rabbits.

The invention claimed is:

1. A saccharide of general formula (I)

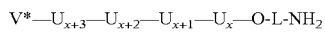

wherein
x is an integer selected from 1, 2, 3 and 4;

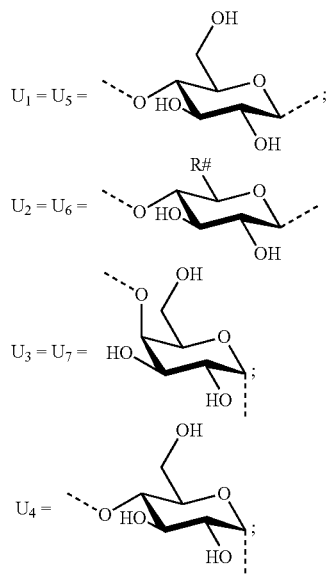

V*— represents H—, H—$U_x$— or H—$U_{x+1}$—$U_x$—;
$R^\#$ represents —COOH or —$CH_2OH$; and
L represents —$(CH_2)_o$—, with o being an integer from 1 to 10; or a pharmaceutically acceptable salt thereof.

2. The saccharide according to claim 1, wherein $R^\#$ represents —COOH.

3. The saccharide according to claim 1, wherein V*— represents H—$U_{x+1}$—$U_x$—.

4. The saccharide according to claim 1, wherein V*— represents H—$U_x$—.

5. The saccharide according to claim 1, wherein V*— represents H—.

6. The saccharide according to claim 1, wherein x represents 3.

7. The saccharide according to claim 1 selected from the group consisting of:
α-D-glucopyrano-(1→4)-α-D-galactopyranosyl-(1→4)-β-D-glucopyranosyl-uronic acid-(1→4)-β-D-glucopyranosyl-(1→1)-(2-amino)ethanol (10),
β-D-glucopyranosyluronic acid-(1→4)-β-D-glucopyranosyl-(1→4)-α-D-glucopyranosyl-(1→4)-α-D-galactopyranosyl-(1→1)-(2-amino)ethanol (18),
5-amino pentanyl β-D-glucopyranosyl uronic acid-(1→4)-β-D-glucopyranosyl-(1→4)-α-D-glucopyranosyl-(1→4)-α-D-galactopyranoside (19),
5-amino pentanyl β-D-glucopyranosyl-(1→4)-β-D-glucopyranosyl-(1→4)-α-D-glucopyranosyl-(1→4)-α-D-galactopyranoside (60),
5-amino pentanyl α-D-galactopyranosyl-(1→4)-β-D-glucopyranosyluronic acid-(1→4)-β-D-glucopyranosyl-(1→4)-α-D-glucopyranoside (20),
5-amino pentanyl α-D-glucopyranosyl-(1→4)-α-D-galactopyranosyl-(1→4)-β-D-glucopyranosyluronic acid-(1→4)-β-D-glucopyranoside (21),
5-amino pentanyl β-D-glucopyranosyl-(1→4)-α-D-glucopyranosyl-(1→4)-α-D-galactopyranosyl-(1→4)-β-D-glucopyranosyl uronic acid (22),
α-D-galactopyranosyl-(1→4)-β-D-glucopyranosyluronate-(1→4)-β-D-glucoyranosyl-α-D-glucopyranosyl-(1→4)-α-D-galactopyranosyl-(1→1)-(2-amino)ethanol (55),
α-D-glucopyranosyl-(1→4)-α-D-galactopyranosyl-(1→4)-β-D-glucopyranosyluronate-(1→4)-β-D-glucoyranosyl-(1→4)-α-D-glucopyranosyl-(1→4)-α-D-galactopyranosyl-(1→1)-(2-amino)ethanol (57),
5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranosyl-(1→4)-α-D-galactopyranoside (63);
5-amino pentanyl galactopyranosyl-(1→4)-α-D-glucopyranosyl-(1→4)-α-D-galactopyranosyl-(1→4)-β-D-glucopyranosyluronic acid-(1→4)-β-D-glucopyranosyl-(1→4)-α-D-glucopyranoside (64);
5-amino pentanyl β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid-(1→4)-β-D-glucopyranoside (65) ;
5-amino pentanyl α-D-galactopyranosyl-(1→4)-β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid (66);
5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranosyl-(1→4)-α-D-galactopyranoside (67);
5-amino pentanyl β-D-glucopyranosyl-(1→4)-α-D-glucopyranosyl-(1→4)-α-D-galactopyranosyl-(1→4)-β-D-glucopyranosyl-(1→4)-β-D-glucopyranosyl-(1→4)-α-D-glucopyranoside (68);
5-amino pentanyl β-D-glucopyranosyl-(1→4)-β-D-glucopyranosyl-(1→4)-α-D-glucopyranosyl-(1→4)-α-D-galactopyranosyl-(1→4)-β-D-glucopyranosyl-(1→4) β-D-glucopyranoside (69);
5-amino pentanyl α-D-galactopyranosyl-(1→4)-β-D-glucopyranosyl-(1→4)-β-D-glucopyranosyl-(1→4)-α-D-glucopyranosyl-(1→4)-α-D-galactopyranosyl-(1→4) β-D-glucopyranoside (70);
3-aminopropyl α-D-galactopyranosyl-(1→4)-β-D-glucopyranosyluronic acid-(1→4) -β-D-glucopyranosyl-(1→4)-α-D-glucopyranosyl-(1→4)-α-D-galactopyranoside (71);
5-amino pentanyl α-D-glucopyranosyl-(1→4)-α-D-galactopyranosyl-(1→4)-β-D-glucopyranosyluronic acid-(1→4)-β-D-glucopyranosyl-(1→4)-α-D-glucopyranoside (72);

3-aminopropyl β-D-glucopyranosyl-(1→4)-α-D-glucopyranosyl-(1→4)-α-D-galactopyranosyl-(1→4)-β-D-glucopyranosyluronic acid-(1→4)-β-D-glucopyranoside (73);

5-amino pentanyl β-D-glucopyranosyluronic acid-(1→4)-β-D-glucopyranosyl-(1→4)-α-D-glucopyranosyl-(1→4)-α-D-galactopyranosyl-(1→4)-β-D-glucopyranosyluronic acid (74);

4-aminobutyl α-D-galactopyranosyl-(1→4)-β-D-glucopyranosyl-(1→4)-β-D-glucopyranosyl-(1→4)-α-D-glucopyranosyl-(1→4)-α-D-galactopyranoside (75);

6-amino hexanyl α-D-glucopyranosyl-(1→4)-α-D-galactopyranosyl-(1→4)-β-D-glucopyranosyl-(1→4)-β-D-glucopyranosyl-(1→4)-α-D-glucopyranoside (76);

3-aminopropyl β-D-glucopyranosyl-(1→4)-α-D-glucopyranosyl-(1→4)-α-D-galactopyranosyl-(1→4)-β-D-glucopyranosyl-(1→4)-β-D-glucopyranoside (77);

5-amino pentanyl β-D-glucopyranosyl-(1→4)-β-D-glucopyranosyl-(1→4)-α-D-glucopyranosyl-(1→4)-α-D-galactopyranosyl-(1→4)-β-D-glucopyranoside (78);

4-aminobutyl α-D-galactopyranosyl-(1→4)-β-D-glucopyranosyl-(1→4)-β-D-glucopyranosyl-(1→4)-α-D-glucopyranoside (79);

3-aminopropyl α-D-glucopyranosyl-(1→4)-α-D-galactopyranosyl-(1→4)-β-D-glucopyranosyl-(1→4)-β-D-glucopyranoside (80); and 6-amino hexanyl β-D-glucopyranosyl-(1→4)-α-D-glucopyranosyl-(1→4)-α-D-galactopyranosyl-(1→4)-β-D-glucopyranoside (81).

8. A conjugate comprising a saccharide of general formula (I) according to claim 1 covalently linked to an immunogenic carrier through the nitrogen atom of the —O-L-NH$_2$ group.

9. The conjugate according to claim 8 of general formula (X)

$$[V^{*}13\ U_{x+3}-U_{x+2}-U_{x+1}-U_{x}-O-L-NH-W]_m-CRM_{197} \quad (X)$$

wherein m is between 2 and 18;
—W— is selected from:

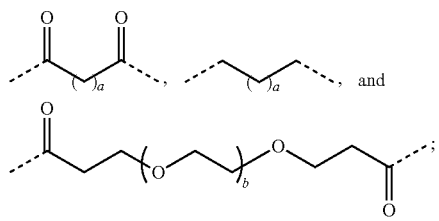

a represents an integer from 1 to 10;
b represents an integer from 1 to 4; and
V*— represents H—, H—U$_x$— or H—U$_{x+1}$—U$_x$—;

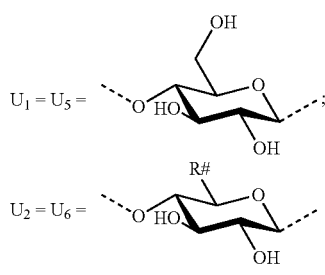

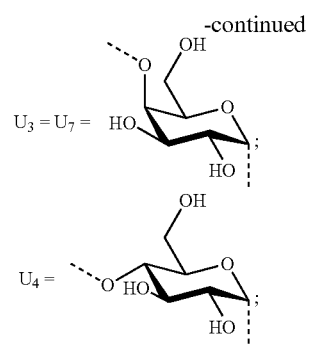

R$^\#$ represents —COOH or —CH$_2$OH;
x is an integer selected from 1, 2, 3 and 4; and
L represents —(CH$_2$)$_o$—, with o being an integer from 1 to 10; or a pharmaceutically acceptable salt thereof.

10. A method for raising a protective immune response in a human or animal host comprising administering to the human or animal host a saccharide according to claim 1.

11. A method for increasing immunogenicity against and/or treating a disease associated with bacteria containing in their capsular polysaccharide one of the following saccharide fragments:
α-D-Glcp-(1→4)-α-D-Galp-(1→4)-β-D-GlcAp-(1→4)-β-D-Glcp,
β-D-Glcp-(1→4)-α-D-Glcp-(1→4)-α-D-Galp-(1→4)-β-D-GlcAp,
β-D-GlcAp-(1→4)-β-D-Glcp-(1→4)-α-D-Glcp-(1→4)-α-D-Galp,
α-D-Galp-(1→4)-β-D-GlcAp-(1→4)-β-D-Glcp-(1→4)-α-D-Glcp,
comprising administering to a patient a saccharide according to claim 1.

12. The method according to claim 11, wherein the bacteria is *Streptococcus pneumoniae* serotype 8.

13. The method according to claim 11, wherein the disease associated with bacteria is selected from the group consisting of: pneumonia, meningitis, otitis media, bacteremia and acute exacerbation of chronic bronchitis, sinusitis, arthritis and conjunctivitis.

14. An immunogenic composition comprising the conjugate according to claim 8 together with at least one pharmaceutical acceptable adjuvant, cryoprotectant, lyoprotectant, excipient and/or diluent.

15. An immunological assay comprising a saccharide of claim 1 conjugated to a solid support, wherein the assay is configured for detection of antibodies against *Streptococcus pneumoniae* serotype 8.

16. A method for raising a protective immune response in a human or animal host comprising administering to the human or animal host a conjugate according to claim 8.

17. A method for raising a protective immune response in a human or animal host comprising administering to the human or animal host a conjugate according to claim 9.

18. A method for increasing immunogenicity against and/or treating a disease associated with bacteria containing in their capsular polysaccharide one of the following saccharide fragments:
α-D-Glcp-(1→4)-α-D-Galp-(1→4)-β-D-GlcAp-(1→4)-β-D-Glcp,
β-D-Glcp-(1→4)-α-D-Glcp-(1→4)-α-D-Galp-(1→4)-β-D-GlcAp,
β-D-GlcAp-(1→4)-β-D-Glcp-(1→4)-α-D-Glcp-(1→4)-α-D-Galp, α-D-Galp-(1→4)-β-D-GlcAp-(1→4)-β-D-Glcp-(1→4)-α-D-Glcp, comprising administering to a patient a conjugate according to claim 8.

19. The method according to claim 18, wherein the bacteria is *Streptococcus pneumoniae* serotype 8.

20. The method according to claim 18, wherein the disease associated with bacteria is selected from the group consisting of: pneumonia, meningitis, otitis media, bacteremia and acute exacerbation of chronic bronchitis, sinusitis, arthritis and conjunctivitis.

21. A method for increasing immunogenicity against and/or treating a disease associated with bacteria containing in their capsular polysaccharide one of the following saccharide fragments:

α-D-Glcp-(1→4)-α-D-Galp-(1→4)-β-D-GlcAp-(1→4)-β-D-Glcp,

β-D-Glcp-(1→4)-α-D-Glcp-(1→4)-α-D-Galp-(1→4)-β-D-GlcAp,

β-D-GlcAp-(1→4)-β-D-Glcp-(1→4)-α-D-Glcp-(1→4)-α-D-Galp,

α-D-Galp-(1→4)-β-D-GlcAp-(1→4)-β-D-Glcp-(1→4)-α-D-Glcp, comprising administering to a patient a conjugate according to claim 9.

22. The method according to claim 21, wherein the bacteria is *Streptococcus pneuimoniae* serotype 8.

23. The method according to claim 21, wherein the disease associated with bacteria is selected from the group consisting of: pneumonia, meningitis, otitis media, bacteremia and acute exacerbation of chronic bronchitis, sinusitis, arthritis and conjunctivitis.

24. The saccharide according to claim 1, wherein L represents —$(CH_2)_n$—, with n being an integer from 1 to 10.

25. The conjugate according to claim 9, wherein L represents (CH2)n—, with n being an integer from 1 to 10.

* * * * *